US006593327B2

(12) United States Patent
Bryant et al.

(10) Patent No.: US 6,593,327 B2
(45) Date of Patent: Jul. 15, 2003

(54) COMPOUNDS AND COMPOSITIONS AS PROTEASE INHIBITORS

(75) Inventors: Clifford M. Bryant, Millbrae, CA (US); James T. Palmer, Corte Madera, CA (US); Robert M. Rydzewski, Newark, CA (US); Eduardo L. Setti, San Mateo, CA (US); Zong-Qiang Tian, Fremont, CA (US); Shankar Venkatraman, Foster City, CA (US); Dan-Xiong Wang, Foster City, CA (US)

(73) Assignee: Axys Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 10/017,851

(22) Filed: Dec. 14, 2001

(65) Prior Publication Data
US 2002/0086996 A1 Jul. 4, 2002

Related U.S. Application Data

(62) Division of application No. 09/526,485, filed on Mar. 15, 2000.
(60) Provisional application No. 60/124,420, filed on Mar. 15, 1999.

(51) Int. Cl.$^7$ ............... A61K 31/4439; A61K 31/506; C07D 417/02; C07D 417/04
(52) U.S. Cl. ............... 514/235.8; 514/254.02; 514/326; 514/342; 544/121; 544/133; 544/360; 544/369; 544/372; 544/390; 546/209; 546/270.4; 546/270.7; 548/194
(58) Field of Search ............... 514/235.8, 254.02, 514/326, 342; 544/121, 33, 560, 369, 372, 390; 546/209, 270.4, 270.7; 548/194

(56) References Cited

U.S. PATENT DOCUMENTS

| 4,927,809 A | 5/1990 | Stuber | 514/20 |
|---|---|---|---|
| 6,456,502 B1 | 9/2002 | Bryant et al. | |

FOREIGN PATENT DOCUMENTS

| EP | 0 355 572 | 2/1990 |
|---|---|---|
| EP | 0 419 683 | 4/1991 |
| EP | 0 536 399 | 4/1993 |
| EP | 0 754 454 | 1/1997 |
| JP | S39-26878 | 5/1967 |
| JP | 63 301868 | 12/1988 |
| WO | WO 90 13561 | 11/1990 |
| WO | WO 95 13069 | 5/1995 |
| WO | WO 95 15309 | 6/1995 |
| WO | WO 95 24382 | 9/1995 |
| WO | WO 98 01133 | 1/1998 |
| WO | WO 98 08867 | 3/1998 |
| WO | WO 99 24460 | 5/1999 |
| WO | WO 00/48992 | 8/2000 |
| WO | WO 00/49007 | 8/2000 |
| WO | WO 00/49008 | 8/2000 |
| WO | WO 00 51998 | 9/2000 |
| WO | WO 00 55124 | 9/2000 |
| WO | WO 01/09110 | 2/2001 |
| WO | WO 01/19816 | 3/2001 |
| WO | WO 01/30772 | 5/2001 |
| WO | WO 01/55125 | 8/2001 |
| WO | WO 01/58886 | 8/2001 |

OTHER PUBLICATIONS

Ashworth, et al. "4–Cyanothiazolidides as very potent, stable inhibitors of dipeptidyl peptidase IV" Bioorganic & Medicinal Chemistry Letters,GB,Oxford, vol. 6, No. 22, Nov. 19, 1996, pp. 2745–2748.

Dufour et al. "Engineering nitrile hydratase activity into a cysteine protease by a single mutation" Biochemistry,US, American Chemical Society. Easton, PA, vol. 34, No. 50, 1995, pp. 16382–13688.

Gour–Salin et al. "Inhibition of papain by peptide nitriles: conversion of the nitrile group into other functionalities via the papain:nitrile thiomidate ester adduct" Canadian J. of Chemistry,CA,National Research Council. Ottawa, vol. 69, No. 8, pp. 1288–1297.

Hanzlik, et al. "Reversible covalent binding of peptide nitrile to papain," Biochim. Biophys. ACTA vol. 1035 No. 1 ppg. 62–70 (1990).

Jingrong, et al. "Aminoacylpyrrolidine–2–nitriles: Potent and stable inhibitors of dipeptidyl–peptidase IV (CD 26)," Archives of Biochemistry and Biophysics vol. 323, No. 1, pp. 148–154 (1995).

Katrinzky, et al. "Benzotriazole–assisted synthesis of aplha.–(acylamino) nitriles and a conceptually novel method for peptide elongation" J. Chem. Soc., Perkin Trans. 1 No. 7, 1990, pp. 1853–1857.

Lipshutz, et al. "Chiral induction in originally racemic amino acids via 5–acyl and 5–acyloxyaminooxazoles" Isr. J. Chem. (1986), 27(1), 49–55 (abstract).

Lipshutz, et al. "Heterocycles as masked diamide/dipeptide equivalents. Formation and reactions of substituted 5–(acylamino)oxazoles as intermediates en route to the cyclopeptide alkaloids" J. Am. Chem. Soc., vol. 105, No. 26, 1983, pp. 7703–7713.

Lipshutz, et al. "Oxazolophanes as masked cyclopeptide alkaloid equivalents: cyclic peptide chemistry without peptide couplings" J. Am. Chem. Soc., vol. 112, No. 19, 1990, pp. 7032–7041.

(List continued on next page.)

Primary Examiner—Fiona T. Powers
(74) Attorney, Agent, or Firm—Townsend and Townsend and Crew LLP

(57) ABSTRACT

The present invention relates to novel N-cyanomethyl amides which are cysteine protease inhibitors, the pharmaceutically acceptable salts and N-oxides thereof, their uses as therapeutic agents and the methods of their making.

13 Claims, No Drawings

OTHER PUBLICATIONS

Mcmath, et al. "Direct dialkylation of peptide nitriles. Application of the synthesis of 1-aminocyclopropane–1–carboxylic acid (Acc)–containing dipeptides," Bull. Soc. Chim. Fr. 134(1) pp. 105–110 (1997).

Moser et al. "130 Poly (dipeptamidinium)–Salze: definition und metoden zur praparativen herstellung. poly (dipeptamidinium) salts: definition and methods of preparation" Helvitica Chimica ACTA,CH,Verlag, Helvitica Chimica ACTA,CH, Basel vol. 69, 1986, pp. 1224–1262.

North et al. "Synthetic studies towards cyclic peptides. Concise synthesis of thiazoline and thiazole containing amino acids" Tetrahedron, vol. 46, No. 24, 1990, pp. 8267–8290.

Picken, et al. "Inhibition of bovine cathepsin B by amino acid–derived nitriles," Biochem. Soc. Trans., vol. 18, No. 2, p. 3016.

Suzue, et al. "Hepatic agents. I. synthesis of aminoacyl( and hydroxyacyl) aminocetonitriles," Chem. Pharm. Bull., Tokyo (1968).

Thompson et al. "Carboxyl–modified amino acids and peptides as protease inhibitors" J. Med. Chem., vol. 29, No. 1, 1986, pp. 104–111.

Vargha, Eugen: "Peptide derivatives. VI. N–protected di–and tripeptide nitriles" Stud. Univ. Babes–Bolyai, Ser. Chem. (1968), 13(2), 31–5 (English astract of article in Romanian).

Varughese "The structure and resonance Raman spectra—structure correlations for methyloxycarbonyl–L–phenylalanyl–L–alanine ethyl dithioester" Can. J. Chem., vol. 64, No. 8, 1986, pp. 1668–1673.

Yamada, et al. "Studies of unusual amino acids and their peptides. IX. The synthetic study of bottromycins B1 and B2" Bull. Chem. Soc. Jpn. (1978), 51(3), 878–83 (abstract).

Bergeman, Macro et al.: "Studies on the reactivity of .alpha.–cyano.alpha–isocyano alkanoates. Versitile synthons for the assembly of imidazoles" Helv. Chim. ACTA, vol. 82, No. 6, 1999, pp. 909–918, p. 912.

COMPOUNDS AND COMPOSITIONS AS PROTEASE INHIBITORS

This application is a divisional of application No. 09/526,485 filed Mar. 15, 2000, now pending which claims the benefit under 35 U.S.C. Sec. 119 (e)(1) of prior filed U.S. Provisional Application No. 60/124,420 filed Mar. 15, 1999.

THE INVENTION

This application relates to compounds and compositions for treating diseases associated with cysteine protease activity, particularly diseases associated with activity of cathepsins B, K, L or S.

DESCRIPTION OF THE FIELD

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increase expression or enhanced activation, however, may have pathological consequences. In this regard, certain cysteine proteases are associated with a number of disease states, including arthritis, muscular dystrophy, inflammation, tumor invasion, glomerulonephritis, malaria, peeiodontal disease, metachromatic leukodystrophy and others. For example, increased cathepsin B levels and redistribution of the enzyme are found in tumors; thus, suggesting a role for the enzyme in tumor invasion and metastasis. In addition, aberrant cathepsin B activity is implicated in such disease states as rheumatoid arthritis, osteo arthritis, pneumocystis carinii, acute pancreatitis, inflammatory airway disease and bone and joint disorders.

The prominent expression of cathepsin K in osteoclasts and osteoclast-related multinucleated cells and its high collagenolytic activity suggest that the enzyme is involved in ososteoclast-mediated bone resorption and, hence, in bone abnormalities such as occurs in osteoporosis. In addition, cathepsin K expression in the lung and its elastinolytic activity suggest that the enzyme plays a role in pulmonary disorders as well.

Cathepsin L is implicated in normal lysosomal proteolysis as well as several disease states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogeneic immune responses, including, but not limited to, rejection of organ transplants or tissue grafts.

In view of the number of diseases wherein it is recognized that an increase in cysteine protease activity contributes to the pathology and/or symptomatology of the disease, molecules which are shown to inhibit the activity of this class of enzymes, in particular molecules which are inhibitors of cathepsins B, K, L and/or S, will be useful as therapeutic agents.

SUMMARY OF THE INVENTION

This Application relates to compounds of Formula I:

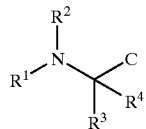

in which:
$R^1$ is a group of Formula (a) or (b):

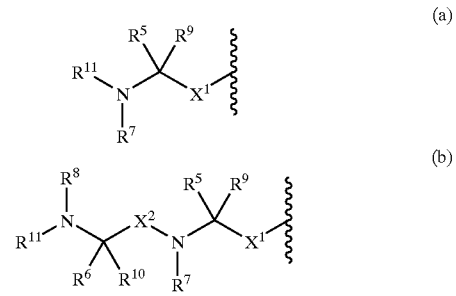

wherein:
$X^1$ and $X^2$ independently are —C(O)— or —CH$_2$S(O)$_2$—;
$R^5$ and $R^6$ independently are hydrogen, (C$_{1-6}$)alkyl or as defined below;
$R^7$ and $R^8$ independently are hydrogen or (C$_{1-6}$)alkyl or as defined below;
$R^9$ and $R^{10}$ independently are (i) (C$_{1-6}$)alkyl optionally substituted with cyano, halo, halo-substituted (C$_{1-3}$)alkyl, nitro, —NR$^{12}$R$^{12}$, —NR$^{12}$C(O)OR$^{12}$, —NR$^{12}$C(O)NR$^{12}$R$^{12}$, —NR$^{12}$C(NR$^{12}$)NR$^{12}$R$^{12}$, —OR$^{12}$, —SR$^{12}$, —C(O)OR$^{12}$, —OC(O)R$^{12}$, —C(O)NR$^{12}$R$^{12}$, —S(O)$_2$NR$^{12}$R$^{12}$, —P(O)(OR$^{12}$)OR$^{12}$, —OP(O)(OR$^{12}$)OR$^{12}$, —NR$^{12}$C(O)R$^{13}$, —S(O)R$^{13}$, —S(O)$_2$R$^{13}$, —C(O)R$^{13}$, —OR$^{14}$, —SR$^{14}$, —S(O)R$^{14}$, —S(O)$_2$R$^{14}$, —C(O)R$^{14}$, —C(O)OR$^{14}$, —OC(O)R$^{14}$, —NR$^{14}$R$^{15}$, —NR$^{15}$C(O)R$^{14}$, —NR$^{15}$C(O)OR$^{14}$, —C(O)NR$^{14}$R$^{15}$, —S(O)$_2$NR$^{14}$R$^{15}$, —NR$^{15}$C(O)NR$^{14}$R$^{15}$ or —NR$^{15}$C(NR$^{15}$)NR$^{14}$R$^{15}$, wherein R$^{12}$ at each occurrence independently is hydrogen, (C$_{1-6}$)alkyl or halo-substituted (C$_{1-3}$)alkyl, R$^{13}$ is (C$_{1-6}$)alkyl or halosubstituted (C$_{1-3}$)alkyl, R$^{14}$ is (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$)alkyl, hetero(C$_{5-12}$)aryl(C$_{0-6}$)alkyl, (C$_{9-12}$)polycycloaryl(C$_{0-6}$)alkyl or hetero(C$_{8-12}$)polycycloaryl(C$_{0-6}$)alkyl and R$^{15}$ is hydrogen or (C$_{1-6}$)alkyl, and wherein within R$^{14}$ said cycloalkyl, heterocycloalkyl, aryl, heteroary, polycycloaryl or heterpolycycloaryl ring optionally is substituted by a group selected from —R$^{16}$, —X$^3$OR$^{16}$, —X$^3$SR$^{16}$, —X$^3$S(O)R$^{16}$, —X$^3$S(O)$_2$R$^{16}$, —X$^3$C(O)R$^{16}$, —X$^3$C(O)OR$^{16}$, —X$^3$OC(O)R$^{16}$, —X$^3$NR$^{16}$R$^{17}$, —X$^3$C(O)NR$^{16}$R$^{17}$, —X$^3$NR$^{17}$C(O)R$^{16}$, —X$^3$NR$^{17}$C(O)OR$^{16}$, —X$^3$C(O)NR$^{16}$R$^{17}$, —X$^3$S(O)$_2$NR$^{16}$R$^{17}$, —X$^3$NR$^{17}$C(O)NR$^{16}$R$^{17}$ or —X$^3$NR$^{17}$C(NR$^{17}$)NR$^{16}$R$^{17}$, wherein $X^3$ is a bond or (C$_{1-6}$)alkylene, R$^{16}$ is hydrogen or (C$_{1-6}$)alkyl and R$^{17}$ is (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$)alkyl, hetero(C$_{5-12}$)aryl(C$_{0-6}$)alkyl, (C$_{9-12}$)polycycloaryl(C$_{0-6}$)alkyl or hetero(C$_{8-12}$)

polycycloaryl($C_{0-6}$)alkyl, or (ii) a group selected from ($C_{3-12}$)Cycloalkyl($C_{0-6}$)alky, hetero($C_{3-12}$)cycloalkyl($C_{0-6}$)alkyl, ($C_{6-12}$)aryl($C_{0-6}$)alkyl, hetero($C_{5-12}$)aryl($C_{0-6}$)alkyl, ($C_{9-12}$)polycycloaryl($C_{0-6}$)alkyl and hetero($C_{8-12}$)polycycloaryl($C_{0-6}$)alkyl, wherein said cycloalkyl, heterocycloalkyl, aryl, heteroaryl, polycycloaryl or heterpolycycloaryl ring optionally is substituted by a group selected from —$R^{16}$, —$X^3OR^{16}$, —$X^3SR^{16}$, —$X^3S(O)R^{16}$, —$X^3S(O)_2R^{16}$, —$X^3C(O)R^{16}$, —$X^3C(O)OR^{16}$, —$X^3OC(O)R^{16}$, —$X^3NR^{16}R^{17}$, $X^3NR^{17}C(O)R^{16}$, —$X^3NR^{17}C(O)OR^{16}$, —$X^3C(O)NR^{16}R^{17}$, —$X^3S(O)_2NR^{16}R^{17}$, —$X^3NR^{17}C(O)NR^{16}R^{17}$ or —$X^3NR^{17}C(NR^{17})NR^{16}R^{17}$, wherein $X^3$, $R^{16}$ and $R^{17}$ are as defined above; wherein within $R^9$ and/or $R^{10}$ any alicyclic or aromatic ring system present may be substituted further by 1 to 5 radicals independently selected from ($C_{1-6}$)alkyl, ($C_{1-6}$)alkylidene, cyano, halo, halo-substituted ($C_{1-4}$)alkyl, nitro, —$X^3NR^{12}R^{12}$, —$X^3NR^{12}C(O)R^{12}$, —$X^3NR^{12}C(O)NR^{12}R^{12}$, —$X^3NR^{12}C(NR^{12})NR^{12}R^{12}$, —$X^3OR^{12}$, —$X^3SR^{12}$, —$X^3C(O)OR^{12}$, —$X^3C(O)NR^{12}R^{12}$, —$X^3S(O)_2NR^{12}R^{12}$, —$X^3P(O)(OR^3)OR^{12}$, —$X^3OP(O)(OR^3)OR^{12}$, —$X^3NR^{12}C(O)R^{13}$, —$X^3S(O)R^{13}$, —$X^3S(O)_2R^{13}$ and —$X^3C(O)R^{13}$, wherein $X^3$, $R^{12}$ and $R^{13}$ are as defined above; or $R^9$ together with $R^7$ and/or $R^{10}$ together with $R^8$ form trimethylene, tetramethylene or phenylene-1,2-dimethylene, optionally substituted with hydroxy, oxo, ($C_{1-4}$)alkyl or methylene; or $R^9$ and $R^5$ together with the carbon atom to which both $R^9$ and $R^5$ are attached and/or $R^{10}$ and $R^6$ together with the carbon atom to which both $R^{10}$ and $R^6$ are attached form ($C_{3-8}$)cycloalkylene or ($C_{3-8}$)heterocycloalkylene; and $R^{11}$ is —$X^4X^5R^{18}$, wherein $X^4$ is —C(O)—, —C(O)C(O)— or —S(O)$_2$—, $X^5$ is a bond, —O— or —$NR^{19}$—, wherein $R^{19}$ is hydrogen or ($C_{1-6}$)alkyl, and $R^{18}$ is (i) ($C_{1-6}$)alkyl optionally substituted by cyano, halo, halo-substituted ($C_{1-3}$)alkyl, nitro, —$NR^{14}R^{14}$, —$NR^{14}C(O)OR^{14}$, —$NR^{14}C(O)NR^{14}R^{14}$, —$NR^{14}C(NR^{14})NR^{14}R^{14}$, —$OR^{14}$, —$SR^{14}$, —$C(O)OR^{14}$, —$C(O)NR^{14}R^{14}$, —$S(O)_2NR^{14}R^{14}$, —$P(O)(OR^{14})OR^{14}$, —$OP(O)(OR^{14})OR^{14}$, —$NR^{14}C(O)R^{15}$, —$S(O)R^{15}$, —$S(O)_2R^{15}$, —$C(O)R^{15}$, —$OR^{20}$, —$SR^{20}$, —$S(O)R^{20}$, —$S(O)_2R^{20}$, —$C(O)R^{20}$, —$C(O)OR^{20}$, —$C(O)NR^{20}R^{21}$, —$NR^{20}R^{21}$, —$NR^{21}C(O)R^{20}$, —$NR^{21}C(O)OR^{20}$, —$NR^{21}C(O)NR^{20}R^{21}$ or —$NR^{21}C(NR^{21})NR^{20}R^{21}$, wherein $R^{14}$ and $R^{15}$ are as defined above, $R^{20}$ is ($C_{3-12}$)cycloalkyl($C_{0-6}$)alkyl, hetero($C_{3-12}$)cycloalkyl($C_{0-6}$)alkyl, ($C_{6-12}$)aryl($C_{0-6}$)alkyl, hetero($C_{5-12}$)aryl($C_{0-6}$)alkyl, ($C_{9-12}$)polycycloaryl($C_{0-6}$)alkyl or hetero($C_{8-12}$)polycycloaryl($C_{0-6}$)alkyl and $R^{21}$ at each occurrence independently is hydrogen or ($C_{1-6}$)alkyl, or (ii) ($C_{3-12}$)cycloalky($C_{0-6}$)alkyl, hetero($C_{3-12}$)Cycloalkyl($C_{0-6}$)alkyl, ($C_{6-12}$)aryl($C_{0-6}$)alkyl, diphenyl($C_{0-6}$)alkyl, hetero($C_{5-12}$)aryl($C_{0-6}$)alkyl, dihetero($C_{5-6}$)aryl($C_{0-6}$)alkyl, ($C_{9-12}$)polycycloaryl($C_{0-6}$)alkyl or hetero($C_{8-6}$)polycycloaryl($C_{0-6}$)alkyl wherein said cycloalkyl, heterocycloalkyl, aryl, diphenyl, heteroaryl, diheteroaryl, polycycloaryl or heterpolycycloaryl ring may be substituted by —$R^{22}$, —$X^3OR^{22}$, —$X^3SR^{22}$, —$X^3S(O)R^{22}$, —$X^3S(O)_2R^{22}$, —$X^3C(O)R^{22}$, —$X^3C(O)OR^{22}$, —$X^3C(O)NR^{22}R^{23}$, —$X^3NR^{22}R^{23}$, —$X^3NR^{23}C(O)R^{22}$, —$X^3NR^{23}C(O)OR^{22}$, —$X^3NR^{23}S(O)_2R^{22}$, —$X^3NR^{23}C(O)NR^{22}R^{23}$ or —$X^3NR^{23}C(NR^{23})NR^{22}R^{23}$, wherein $X^3$ is as defined above, $R^{22}$ is ($C_{3-12}$)cycloalkyl($C_{0-6}$)alkyl, hetero($C_{3-12}$)cycloalkyl($C_{0-6}$)alkyl, ($C_{6-12}$)aryl($C_{0-6}$)alkyl, hetero($C_{5-12}$)aryl($C_{0-6}$)alkyl, ($C_{9-12}$)polycycloaryl($C_{0-6}$)alkyl or hetero($C_{8-12}$)polycycloaryl($C_{0-6}$)alkyl and $R^{23}$ at each occurrence independently is hydrogen or ($C_{1-6}$)alkyl; wherein within $R^{11}$ any alicyclic or aromatic ring system present may be substituted further by 1 to 5 radicals independently selected from ($C_{1-6}$)alkyl, ($C_{1-6}$)alkylidene, cyano, halo, halo-substituted ($C_{1-4}$)alkyl, nitro, —$X^3NR^{12}R^{12}$, —$X^3NR^{12}C(O)OR^{12}$, —$X^3NR^{12}C(O)NR^{12}R^{12}$, —$X^3NR^{12}C(NR^{12})NR^{12}R^{12}$, —$X^3OR^{12}$, —$X^3SR^{12}$, —$X^3C(O)OR^{12}$, —$X^3C(O)NR^{12}R^{12}$, —$X^3S(O)_2NR^{12}R^{12}$, —$X^3P(O)(OR^3)OR^{12}$, —$X^3OP(O)(OR^3)OR^{12}$, —$X^3NR^{12}C(O)R^{13}$, —$X^3S(O)R^{13}$, —$X^3S(O)_2R^{13}$ and —$X^3C(O)R^{13}$, wherein $X^3$, $R^{12}$ and $R^{13}$ are as defined above;

$R^2$ is hydrogen or ($C_{1-6}$)alkyl;

$R^3$ is hydrogen, ($C_{1-6}$)alkyl or as defined below;

$R^4$ is (i) cyano, —$C(O)OR^{12}$ or ($C_{1-6}$)alkyl, wherein said alkyl optionally is substituted with cyano, halo, halo-substituted ($C_{1-3}$)alkyl, nitro, —$NR^{12}R^{12}$, —$NR^{12}C(O)OR^{12}$, —$NR^{12}C(O)NR^{12}R^{12}$, —$NR^{12}C(NR^{12})NR^{12}R^{12}$, —$OR^{12}$, —$SR^{12}$, —$C(O)OR^{12}$, $OC(O)R^{12}$, —$C(O)NR^{12}R^{12}$, —$S(O)_2NR^{12}R^{12}$, —$P(O)(OR^{12})OR^{12}$, —$OP(O)(OR^{12})OR^{12}$, —$NR^{12}C(O)R^{13}$, —$S(O)R^{13}$, —$S(O)_2R^{13}$, —$C(O)R^{13}$, $OR^{14}$, —$SR^{14}$, —$S(O)R^{14}$, —$S(O)_2R^{14}$, —$C(O)R^{14}$, —$C(O)OR^{14}$, —$OC(O)R^{14}$, —$NR^{14}R^{15}$, —$NR^{15}C(O)R^{14}$, —$NR^{15}C(O)OR^{14}$, —$C(O)NR^{14}R^{15}$, —$S(O)_2NR^{14}R^{15}$, —$NR^{15}C(O)NR^{14}R^{15}$ or —$NR^{15}C(NR^{15})NR^{14}R^{15}$, wherein $R^{12}$, $R^{13}$ and $R^{14}$ are as defined above, or (ii) a group selected from ($C_{3-12}$)cycloalkyl($C_{0-6}$)alkyl, hetero($C_{3-12}$)Cycloalkyl($C_{0-6}$)alkyl, ($C_{6-12}$)aryl($C_{0-6}$)alkyl, hetero($C_{5-12}$)aryl($C_{0-6}$)alkyl, ($C_{9-12}$)polycycloaryl($C_{0-6}$)alkyl and hetero($C_{8-12}$)polycycloaryl($C_{0-6}$)alkyl, wherein said cycloalkyl, heterocycloalkyl, aryl, heteroaryl, polycycloaryl or heterpolycycloaryl ring optionally is substituted by a group selected from —$R^{16}$, —$X^3OR^{16}$, —$X^3SR^{16}$, —$X^3S(O)R^{16}$, —$X^3S(O)_2R^{16}$, —$X^3C(O)R^{16}$, —$X^3C(O)OR^{16}$, —$X^3OC(O)R^{16}$, $X^3NR^{16}R^{17}$, —$X^3NR^{17}C(O)R^{16}$, —$X^3NR^{17}C(O)OR^{16}$, —$X^3C(O)NR^{16}R^{17}$, —$X^3S(O)_2NR^{16}R^{17}$, —$X^3NR^{17}C(O)NR^{16}R^{17}$ or —$X^3NR^{17}C(NR^{17})NR^{16}R^{17}$, wherein $X^3$, $R^{16}$ and $R^{17}$ are as defined above; wherein within $R^4$ any alicyclic or aromatic ring system present may be substituted further by 1 to 5 radicals independently selected from ($C_{1-6}$)alkyl, ($C_{1-6}$)alkylidene, cyano, halo, halo-substituted ($C_{1-4}$)alkyl, nitro, —$X^3NR^{12}R^{12}$, —$X^3NR^{12}C(O)OR^{12}$, —$X^3NR^{12}C(O)NR^{12}R^{12}$, —$X^3NR^{12}C(NR^{12})NR^{12}R^{12}$, —$X^3OR^{12}$, —$X^3SR^{12}$, —$X^3C(O)NR^{12}R^{12}$, —$X^3S(O)_2NR^{12}R^{12}$, —$X^3P(O)(OR^3)OR^{12}$, —$X^3OP(O)(OR^3)OR^{12}$, —$X^3NR^{12}C(O)R^{13}$, —$X^3S(O)R^{13}$, —$X^3S(O)_2R^{13}$ and —$X^3C(O)R^{13}$, wherein $X^3$, $R^{12}$ and $R^{13}$ are as defined above; or $R^4$ taken together with $R^2$ forms trimethylene, tetramethylene or phenylene-1,2-dimethylene, optionally substituted with hydroxy, oxo, ($C_{1-4}$)alkyl or methylene; or $R^4$ and $R^3$ taken together with the carbon atom to which both $R^4$ and $R^3$ are attached form ($C_{3-8}$)cycloalkylene or ($C_{3-8}$)heterocycloalkylene, wherein said cycloalkylene or heterocycloalkylene is optionally substituted with 1 to 3 radicals independently selected from $(C_{1-6})$alkyl, $(C_{1-6})$alkylidene, cyano, halo, halo-substituted $(C_{1-4})$alkyl, nitro, —$X^3NR^{12}R^{12}$, —$X^3NR^{12}C(O)OR^{12}$, —$X^3NR^{12}C(O)NR^{12}R^{12}$, —$X^3NR^{12}C(NR^{12})NR^{12}R^{12}$, —$X^3OR^{12}$, —$X^3SR^{12}$, —$X^3C(O)OR^{12}$, —$X^3C(O)NR^{12}R^{12}$, —$X^3S(O)_2NR^{12}R^{12}$, —$X^3P(O)(OR^3)OR^{12}$, —$X^3OP(O)(OR^3)OR^{12}$, —$X^3NR^{12}C(O)R^{13}$, —$X^3S(O)R^{13}$, —$X^3S(O)_2R^{13}$ and —$X^3C(O)R^{13}$, wherein $X^3$, $R^{12}$ and $R^{13}$ are as defined above; and the N-oxide derivatives, prodrug derivatives, protected derivatives, individual isomers and mixtures of isomers; and the pharmaceutically acceptable salts thereof.

A second aspect of the invention relates to compounds of Formula II:

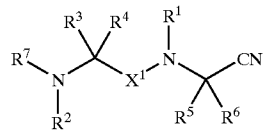

II in which:

$X^1$ is selected from —C(O)—, —S(O)—, —C(S), —S(O)$_2$— and —P(O)$_2$—;

$R^1$ and $R^2$ independently are hydrogen or $(C_{1-6})$alkyl;

$R^3$ and $R^4$ independently are hydrogen or $(C_{1-6})$alkyl or $R^3$ and $R^4$ taken together with the carbon atom to which both $R^3$ and $R^4$ are attached form $(C_{3-8})$cycloalkylene;

$R^5$ and $R^6$ independently are hydrogen or $(C_{1-6})$alkyl or $R^5$ and $R^6$ taken together with the carbon atom to which both $R^5$ and $R^6$ are attached form $(C_{3-8})$cycloalkylene or $(C_{3-8})$heterocycloalkylene; and $R^7$ is —$X^2X^3R^9$, wherein $X^2$ is —C(O)—, —S(O)—, —C(S)—, —S(O)$_2$— or —P(O)$_2$—, $X^3$ is a bond, —O— or —NR$^{10}$—, wherein $R^{10}$ is hydrogen or $(C_{1-6})$alkyl, and $R^9$ is $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alky), wherein within $R^9$ said cycloalkyl, heterocycloalkyl, phenyl or heteroaryl is substituted by —$R^{12}$, —$X^4NR^{11}R^{12}$, —$X^4NR^{11}C(O)R^{12}$, —$X^4NR^{11}C(O)OR^{12}$, —$X^4NR^{11}C(O)NR^{11}R^{12}$, —$X^4NR^{11}C(NR^{11})NR^{11}R^{12}$, —$X^4OR^{12}$, —$X^4SR^{12}$, —$X^4S(O)R^{12}$, —$X^4S(O)_2R^{12}$, —$X^4C(O)R^{12}$, —$X^4C(O)OR^{12}$, —$X^4OC(O)R^{12}$, —$X^4C(O)NR^{11}R^{12}$, —$X^4OC(O)NR^{11}R^{12}$, —$X^4S(O)_2NR^{11}R^{12}$, —$X^4P(O)(OR^{11})OR^{12}$ or —$X^4OP(O)(OR^{11})OR^{12}$, wherein $X^4$ is a bond or $(C_{1-6})$alkylene, $R^{11}$ at each occurrence is hydrogen or $(C_{1-6})$alkyl and $R^{12}$ is $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl, wherein within $R^{12}$ said cycloalkyl, heterocycloalkyl, phenyl or heteroaryl is substituted by —$R^{13}$, —$X^4NR^{11}R^{13}$, —$X^4NR^{11}C(O)R^{13}$, —$X^4NR^{11}C(O)OR^{13}$, —$X^4NR^{11}C(O)NR^{11}R^{13}$, —$X^4NR^{11}C(NR^{11})NR^{11}R^{13}$, —$X^4OR^{13}$, —$X^4SR^{13}$, —$X^4S(O)R^{13}$, —$X^4S(O)_2R^{13}$, —$X^4C(O)R^{13}$, —$X^4C(O)OR^{13}$, —$X^4OC(O)R^{13}$, —$X^4C(O)NR^{11}R^{13}$, —$X^4OC(O)NR^{11}R^{13}$, —$X^4S(O)_2NR^{11}R^{13}$, —$X^4P(O)(OR^{11})OR^{13}$ or —$X^4OP(O)(OR^{11})OR^{13}$, wherein $X^4$ and $R^{11}$ are as defined above and $R^{13}$ is $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl, wherein within $R^7$ any alicyclic and aromatic rings present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^5NR^{14}R^{14}$, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^5)OR^{14}$, —$X^5OP(O)(OR^5)OR^{14}$, —$X^5NR^{14}C(O)R^{15}$, —$X^5S(O)R^{15}$, —$X^5S(O)_2R^{15}$ and —$X^5C(O)R^{15}$, wherein $X^5$ is a bond or $(C_{1-6})$alkylene, $R^{14}$ at each occurrence independently is hydrogen, $(C_{1-6})$alkyl or halo-substituted $(C_{1-3})$alkyl and $R^{15}$ is $(C_{1-6})$alkyl or halo-substituted $(C_{1-3})$alkyl; and the N-oxide derivatives, prodrug derivatives, protected derivatives, individual isomers and mixtures of isomers; and the pharmaceutically acceptable salts thereof.

A third aspect of the invention is a pharmaceutical composition which contains a compound of Formula I or a N-oxide derivative, prodrug derivative, individual isomer or mixture of isomers or a pharmaceutically acceptable salt thereof in admixture with one or more suitable excipients.

A fourth aspect of the invention is a method of treating a disease in an animal in which inhibition of a cysteine protease can prevent, inhibit or ameliorate the pathology and/or symptomatology of the disease, which method comprises administering to the animal a therapeutically effective amount of compound of Formula I or a N-oxide derivative, prodrug derivative, individual isomer or mixture of isomers or a pharmaceutically acceptable salt thereof.

A fifth aspect of the invention is the processes for preparing compounds of Formula I and the N-oxide derivatives, prodrug derivative, protected derivatives, individual isomers and mixtures of isomers, and the pharmaceutically acceptable salts thereof as set forth in "Detailed Description of the Invention".

DETAILED DESCRIPTION OF THE INVENTION

Definitions

Unless otherwise stated, the following terms used in the specification and claims are defined for the purposes of this Application and have the meanings given this Section:

"Alicyclic" means a moiety characterized by arrangement of the carbon atoms in closed non-aromatic ring structures having properties resembling those of aliphatics and may be saturated or partially unsaturated with two or more double or triple bonds.

"Aliphatic" means a moiety characterized by straight or branched chain arrangement of the constituent carbon atoms and may be saturated or partially unsaturated with two or more double or triple bonds.

"Alkyl" indicated alone means a straight or branched, saturated or unsaturated aliphatic radical having the number of carbon atoms indicated (e.g., $(C_{1-6})$alkyl includes methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl indicated as part of a larger radical (e.g., as in arylalkyl) means a straight or branched, saturated or unsaturated aliphatic divalent radical having the number of atoms indicated or when 0 atoms are indicated means a bond (e.g., $(C_{0-3})$alkyl of $(C_{3-12})$Cycloalkyl$(C_{0-3})$alkyl means a bond, methylene, ethylene, trimethylene, 1-methylethylene, or the like).

"Alkylene", unless indicated otherwise, means a straight or branched, saturated or unsaturated, aliphatic, divalent radical having the number of carbon atoms indicated (e.g. $(C_{1-6})$alkylene includes methylene (—CH$_2$—), ethylene (—CH$_2$CH$_2$—), trimethylene (—CH$_2$CH$_2$CH$_2$—), 2-methyltrimethylene (—CH$_2$CH(CH$_3$)CH$_2$—), tetramethylene (—CH$_2$CH$_2$CH$_2$CH$_2$—), 2-butenylene (—CH$_2$CH=CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like). For example, the instance wherein R$^5$ is hydrogen and R$^9$ taken together with R$^7$ forms optionally substituted trimethylene is illustrated by the following:

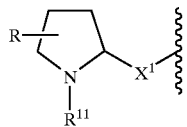

in which R is an optional hydroxy or oxo group and X$^1$ and R$^{11}$ are as defined in the Summary of the Invention.

"Alkylidene" means a straight or branched saturated or unsaturated, aliphatic, divalent radical having the number of carbon atoms indicated (e.g. (C$_{1-6}$)alkylidene includes methylene (=CH$_2$), ethylidene (=CHCH$_3$), isopropylidene (=C(CH$_3$)$_2$), propylidene (=CHCH$_2$CH$_3$), allylidene (=CHCH=CH$_2$), and the like).

"Amino" means the radical —NH$_2$. Unless indicated otherwise, the compounds of the invention containing amino moieties include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, etc.) and non-mammals (e.g., birds, etc.).

"Aryl" means a monocyclic or bicyclic ring assembly (fused or linked by a single bond) containing the total number of ring carbon atoms indicated, wherein each ring is comprised of 6 ring carbon atoms and is aromatic or when fused with a second ring forms an aromatic ring assembly. For example,(C$_{6-12}$)aryl includes phenyl, naphthyl and biphenylyl.

"Aromatic" means a moiety wherein the constituent atoms make up an unsaturated ring system, all atoms in the ring system are sp2 hybridized and the total number of pi electrons is equal to 4n+2.

"Carbamoyl" means the radical —C(O)NH$_2$. Unless indicated otherwise, the compounds of the invention containing carbamoyl moieties include protected derivatives thereof. Suitable protecting groups for carbamoyl moieties include acetyl, tert-butoxycarbonyl, benzyloxycarbonyl, and the like and both the unprotected and protected derivatives fall within the scope of the invention.

"Carboxy" means the radical —C(O)OH. Unless indicated otherwise, the compounds of the invention containing carboxy moieties include protected derivatives thereof. Suitable protecting groups for carboxy moieties include benzyl, tert-butyl, and the like.

"Cycloalkyl" means a saturated or partially unsaturated, monocyclic ring, bicyclic ring assembly (directly linked by a single bond or fused) or bridged polycyclic ring assembly containing the number of annular carbon atoms indicated, and any carbocyclic ketone, thioketone or iminoketone derivative thereof (e.g., (C$_{3-12}$)cycloalkyl includes cyclopropyl, cyclobutyl, cyclopentyl, cyclohexyl, cyclohexenyl, 2,5-cyclohexadienyl, bicyclohexylyl, cyclopentylcyclohexyl, bicyclo[2.2.2]octyl, adamantan-1-yl, decahydronaphthalenyl, oxocyclohexyl, dioxocyclohexyl, thiocyclohexyl, 2-oxobicyclo[2.2.1]hept-1-yl, etc.).

"Cycloalkylene" means a saturated or partially unsaturated, monocyclic ring or bridged polycyclic ring assembly containing the number of annular carbon atoms indicated, and any carbocyclic ketone, thioketone or iminoketone derivative thereof. For example, the instance wherein R$^9$ and R$^5$ together with the carbon atom to which both R$^9$ and R$^5$ are attached form (C$_{3-8}$)cycloalkylene" includes, but is not limited to, the following:

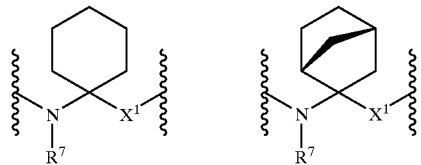

in which X$^1$ and R$^7$ are as defined in the Summary of the Invention.

"Disease" specifically includes any unhealthy condition of an animal or part thereof and includes an unhealthy condition which may be caused by, or incident to, medical or veterinary therapy applied to that animal, i.e., the "side effects" of such therapy.

"Guanidino" means the radical —NHC(NH)NH$_2$. Unless indicated otherwise, the compounds of the invention containing guanidino moieties include protected derivatives thereof. Suitable protecting groups for amino moieties include acetyl, tert-butoxycarbonyl, benzyloxycarbonyl, and the like.

"Halo" means fluoro, chloro, bromo or iodo.

"Halo-substituted alkyl", as a group or part of a group, means "alkyl" substituted by one or more "halo" atoms, as such terms are defined in this Application. Halo-substituted alkyl includes haloalkyl, dihaloalkyl, trihaloalkyl, perhaloalkyl and the like (e.g. halo-substituted (C$_{1-3}$)alkyl includes chloromethyl, dicloromethyl, difluoromethyl, trifluromethyl, 2,2,2-trifluoroethyl, perfluoroethyl, 2,2,2-trifluoro-1,1-dichloroethyl, and the like).

"Heteroaryl" means aryl, as defined in this Application, provided that one or more of the ring member carbon atoms indicated, is replaced by heteroatom moiety selected from —N=, —NR—, —O— or —S—, wherein R is hydrogen, (C$_{1-6}$)alkyl or a protecting group, and each ring contained therein is comprised of 5 to 6 ring member atoms. For example, hetero(C$_{5-12}$)aryl as used in this Application includes benzofuryl, benzooxazolyl, benzothiazolyl, [2,4'] bipyridinylyl, carbazolyl, carbolinyl, chromenyl, cinnolinyl, furazanyl, furyl, imidazolyl, indazolyl, indolyl, indolizinyl, isobenzofuryl, isochromenyl, isooxazolyl, isoquinolyl, isothiazolyl, naphthyridinyl, oxazolyl, perimidinyl, 2-phenylpyridyl, phthalazinyl, pteridinyl, purinyl, pyrazinyl, pyradazinyl, pyrazolyl, pyridyl, pyrimidinyl, pyrrolizinyl, pyrrolidinyl, pyrrolyl, pyranyl, quinazolinyl, quinolizinyl, quinolyl, quinoxalinyl, tetrazolyl, thiazolyl, 4-thiazol4-ylphenyl, thienyl, xanthenyl, and the like. Suitable protecting groups include tert-butoxycarbonyl, benzyloxycarbonyl, benzyl, 4-methoxybenzyl, 2-nitrobenzyl, and the like.

"Heterocycloalkyl" means cycloalkyl, as defined herein, provided that one or more of the ring member carbon atoms indicated is replaced by heteroatom moiety selected from —N=, —NR—, —O—, —S— or —S(O)$_2$, wherein R is hydrogen, (C$_{1-6}$)alkyl or a protecting group, and any carbocyclic ketone, thioketone or iminoketone derivative thereof (e.g. the term heterocyclo(C$_{5-12}$)alkyl includes [1,4'] bipiperidinylyl, dihydrooxazolyl, morpholinyl, 1-morpholin-4-ylpiperidinyl, piperazinyl, piperidyl, pirazolidinyl, pirazolinyl, pyrrolinyl, pyrrolidinyl, quinuclidinyl, and the like). Suitable protecting groups include tert-butoxycarbonyl, benzyloxycarbonyl, benzyl, 4-methoxybenzyl, 2-nitrobenzyl, and the like. For example, a compound of Formula I wherein $R^1$ is piperidin-4-ylcarbonyl may exist as either the unprotected or a protected derivative, e.g. wherein $R^1$ is 1-tert-butoxycarbonylpiperidin-4-ylcarbonyl, and both the unprotected and protected derivatives fall within the scope of the invention.

"Heterocycloalkylene" means cycloalkylene, as defined in this Application, provided that one or more of the ring member carbon atoms indicated, is replaced by heteroatom moiety selected from —N=, —NR—, —O—, —S— or —S(O)$_2$—, wherein R is hydrogen or (C$_{1-6}$)alkyl. For example, the instance wherein $R^3$ and $R^4$ together with the carbon atom to which both $R^3$ and $R^4$ are attached form hetero(C$_{3-8}$)Cycloalkylene" includes, but is not limited to, the following:

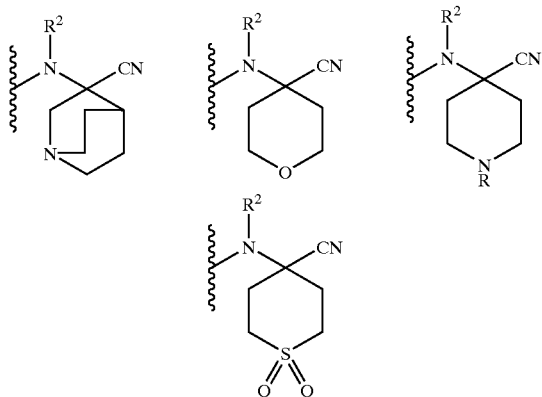

in which R is hydrogen, (C$_{1-6}$)alkyl or a protecting group and $R^2$ is as defined in the Summary of the invention.

"Heteropolycycloaryl" means polycycloaryl, as defined herein, except one or more of the annular carbon atoms indicated are replaced by a heteroatom moiety selected from —N=, —NR—, —O—, —S— or —S(O)$_2$—, wherein R is hydrogen, (C$_{1-6}$)alkyl or a protecting group, and any carbocyclic ketone, thioketone or iminoketone derivative thereof (e.g., hetero(C$_{8-12}$)polycycloaryl includes 3,4-dihydro-2H-quinolinyl, 5,6,7,8-tetrahydroquinolinyl, 3,4-dihydro-2H-[1,8]naphthyridinyl, morpholinylpyridyl, piperidinylphenyl, 1,2,3,4,5,6-hexahydro-[2,2']bipyridinylyl, 2,4oxo-3,4-dihydro-2H-quinazolinyl, 3-oxo-2,3-dihydrobenzo[1,4]oxazinyl, etc.).

"Heteroatom moiety" includes —N=, —NR—, —O—, —S— or —S(O)$_2$—, wherein R is hydrogen, (C$_{1-6}$)alkyl or a protecting group.

"Hydroxy" means the radical —OH. Unless indicated otherwise, the compounds of the invention containing hydroxy radicals include protected derivatives thereof. Suitable protecting groups for hydroxy moieties include benzyl and the like. For example, a compound of Formula I wherein the $R^9$ contains a hydroxy moiety exist as either the unprotected or a protected derivative, e.g., wherein $R^6$ is benzyloxybenzyl, and both the unprotected and protected derivatives fall within the scope of the invention.

"Iminoketone derivative" means a derivative containing the moiety —C(NR)—, wherein R is hydrogen or (C$_{1-6}$) alkyl.

"Isomers" mean compounds of Formula I having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomers or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 3rd edition, March, Jerry, John Wiley & Sons, New York, 1985). It is understood that the names and illustration used in this Application to describe compounds of Formula I are meant to be encompassed all possible stereoisomers. Thus, for example, the name 1-(1-cyano-1-methylethylcarbamoyl)-3-methylbutylcarbamate is meant to include 1S-(1-cyano-1-methylethylcarbamoyl)-3-methylbutylcarbamate and 1R-(1-cyano-1-methylethylcarbamoyl)-3-methylbutylcarbamate and any mixture, racemic or otherwise, thereof.

"Ketone derivative" means a derivative containing the moiety —C(O)—.

"Methylene" means the divalent radical —CH$_2$— or CH$_2$=, wherein its free valances can be attached to different atoms or the same atom. For example, the instance wherein $R^9$ together with $R^7$ forms trimethylene substituted methylene includes the following:

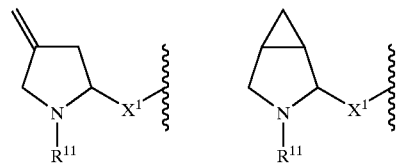

in which $X^1$ and $R^{11}$ are as defined in the Summary of the invention, and may be referred to as 2,2-methylene and 1,2-methylene, respectively.

"Nitro" means the radical —NO$_2$.

"Optional" or "optionally" means that the subsequently described event or circumstance may or may not occur, and that the description includes instances where the event or circumstance occurs and instances in which it does not. For example, the phrase "any 1 to 3 annular atoms of any aromatic ring with available valences comprising $R^6$ optionally independently is substituted" means that the aromatic ring referred to may or may not be substituted in order to fall within the scope of the invention.

"N-oxide derivatives" means a derivatives of compound of Formula I in which nitrogens are in an oxidized state (i.e., O←N) and which possess the desired pharmacological activity.

"Oxo" means the radical =O.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula I which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, ammonium hydroxide, aluminum hydroxide and calcium hydroxide. Acceptable organic bases include ethanolamine, diethanolamine, triethanolamine, tromethamine, N-methylglucamine and the like.

"Phenylene-1,2-dimethylene" means the divalent radical —CH$_2$C$_6$H$_4$CH$_2$—, wherein the methylene moieties are attached at the 1- and 2-positions of the phenylene moiety. For example, a group of Formula (a), wherein R$^9$ together with R$^7$ form optionally substituted phenylene-1,2-dimethylene is illustrated by the following formula:

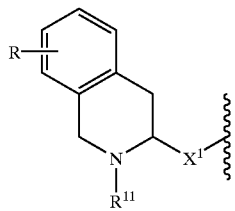

in which R is an optional hydroxy or (C$_{1-4}$)alkyl group and X$^1$ and R$^{11}$ are as defined in the Summary of the Invention.

"Polycycloaryl" means a bicyclic ring assembly (directly linked by a single bond or fused) containing the number of ring member carbon atoms indicated, wherein at least one, but not all, of the fused rings comprising the radical is aromatic, and any carbocyclic ketone, thioketone or iminoketone derivative thereof (e.g., (C$_{9-12}$)polycycloaryl includes indanyl, indenyl, 1,2,3,4-tetrahydronaphthalenyl, 1,2-dihydronaphthalenyl, cyclohexylphenyl, phenylcyclohexyl, 2,4-dioxo-1,2,3,4-tetrahydronaphthalenyl, and the like).

"Prodrug derivatives" means derivatives of compounds of Formula I which are converted in vivo to the corresponding non-derivatized form of a compound of Formula I.

"Protected derivatives" means derivatives of compounds of Formula I in which a reactive site or sites are blocked with protecting groups. Protected derivatives of compounds of Formula I are useful in the preparation of compounds of Formula I or in themselves may be active cysteine protease inhibitors. A comprehensive list of suitable protecting groups can be found in T. W. Greene, *Protecting Groups in Organic Synthesis,* John Wiley & Sons, Inc. 1981.

"Therapeutically effective amount" means that amount which, when administered to an animal for treating a disease, is sufficient to effect such treatment for the disease.

"Thioketone derivative" means a derivative containing the moiety —C(S)—.

"Treatment" or "treating" means any administration of a compound of the present invention and includes:
(1) preventing the disease from occurring in an animal which may be predisposed to the disease but does not yet experience or display the pathology or symptomatology of the disease,
(2) inhibiting the disease in an animal that is experiencing or displaying the pathology or symptomatology of the diseased (i.e., arresting further development of the pathology and/or symptomatology), or
(3) ameliorating the disease in an animal that is experiencing or displaying the pathology or symptomatology of the diseased (i.e., reversing the pathology and/or symptomatology).

"Ureido" means the radical —NHC(O)NH$_2$. Unless indicated otherwise, the compounds of the invention containing ureido moieties include protected derivatives thereof. Suitable protecting groups for ureido moieties include acetyl, tert-butoxycarbonyl, benzyloxycarbonyl, and the like. For example, a compound of Formula I wherein the R$^9$ contains an ureido moiety may exist as either the unprotected or a protected derivative and the like, and both the unprotected and protected derivatives fall within the scope of the invention.

Specific Embodiments

While the broadest definition of the invention is set forth in the Summary of the Invention, certain aspects of the invention are preferred. A preferred aspect of the invention are the compounds of Formula I in which:

R$^1$ is a group Formula (a), wherein within Formula (a):
  X$^1$ is —C(O)—;
  R$^5$ is hydrogen, (C$_{1-4}$)alkyl or as defined together with R$^9$;
  R$^7$ is hydrogen, (C$_{1-6}$)alkyl or as defined together with R$^9$;
  R$^9$ is (i) (C$_{1-6}$)alkyl optionally substituted with halo-substituted (C$_{1-3}$)alkyl, —OR$^{12}$, or —NR$^{12}$C(NR$^{12}$)NR$^{12}$R$^{12}$, wherein R$^{12}$ at each occurrence independently is hydrogen, (C$_{1-6}$)alkyl or halo-substituted (C$_{1-3}$)alkyl, or (ii) (C$_{6-12}$)aryl(C$_{0-6}$)alkyl, or
  R$^9$ taken together with R$^7$ forms trimethylene optionally substituted oxo, (C$_{1-4}$)alkyl or methylene, or
  R$^9$ and R$^5$ together with the carbon atom to which both R$^9$ and R$^5$ are attached form (C$_{3-8}$)Cycloalkylene or (C$_{3-8}$)heterocycloalkylene; and
  R$^{11}$ is —X$^4$X$^5$R$^{18}$, wherein X$^4$ is —C(O)—, X$^5$ is a bond, —O— or —S(O)$_2$— and R$^{18}$ is (i) (C$_{1-6}$)alkyl optionally substituted by —C(O)NR$^{20}$R$^{21}$ or —NR$^{21}$C(O)R$^{20}$, wherein R$^{20}$ is (C$_{6-12}$)aryl(C$_{0-6}$)alkyl and R$^{21}$ at each occurrence independently is hydrogen or (C$_{1-6}$)alkyl, or (ii) (C$_{3-12}$)cycloalkyl (C$_{0-6}$)alkyl, hetero(C$_{3-12}$)cycloalkyl(C$_{0-6}$)alkyl, (C$_{6-12}$)aryl(C$_{0-6}$)alkyl, hetero(C$_{5-12}$)aryl(C$_{0-6}$)alkyl or hetero(C$_{8-12}$)polycycloaryl(C$_{0-6}$)alkyl, wherein said heterocycloalkyl, aryl, heteroaryl or heteropolycycloaryl ring may be substituted by —$R^{22}$, —$X^3OR^{22}$, —$X^3NR^{22}R^{23}$, —$X^3NR^{17}C(O)R^{16}$, —$X^3NR^{23}C(O)OR^{22}$, —$X^3NR^{23}S(O)_2R^{22}$, —$X^3S(O)_2R^{22}$, —$X^3C(O)R^{22}$ or —$X^3NR^{23}C(O)NR^{22}R^{23}$, wherein $X^3$ is a bond or $(C_{1-6})$alkylene, $R^{22}$ is hetero$(C_{3-12})$cycloalkyl$(C_{0-6})$alkyl and $R^{23}$ at each occurrence independently is hydrogen or $(C_{1-6})$alkyl; wherein within $R^{11}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^3NR^{12}R^{12}$, —$X^3NR^{12}C(O)OR^{12}$, —$X^3NR^{12}C(O)NR^{12}R^{12}$, —$X^3NR^{12}C(NR^{12})NR^{12}R^{12}$, —$X^3OR^{12}$, —$X^3SR^{12}$, —$X^3C(O)OR^{12}$, —$X^3C(O)NR^{12}R^{12}$, —$X^3S(O)_2NR^{12}R^{12}$, —$X^3P(O)(OR^3)OR^{12}$, —$X^3OP(O)(OR^3)OR^{12}$, —$X^3NR^{12}C(O)R^{13}$, —$X^3S(O)R^{13}$, —$X^3S(O)_2R^{13}$ and —$X^3C(O)R^{13}$, wherein $X^3$ is a bond or $(C_{1-6})$alkylene, $R^{12}$ at each occurrence independently is hydrogen, $(C_{1-6})$alkyl or halo-substituted $(C_{1-3})$alkyl and $R^{13}$ is $(C_{1-6})$alkyl or halo-substituted $(C_{1-3})$alkyl;

$R^3$ is hydrogen, $(C_{1-6})$alkyl or as defined together with $R^4$; and $R^4$ is (i) hydrogen, cyano, —$C(O)OR^{12}$ or $(C_{1-6})$alkyl wherein said alkyl optionally is substituted with —$C(O)OR^{12}$, —$OC(O)R^{12}$, wherein $R^{12}$ at each occurrence independently is hydrogen, $(C_{1-6})$alkyl or halo-substituted $(C_{1-3})$alkyl, or (ii) $(C_{6-10})$aryl$(C_{0-3})$alkyl or $R^4$ taken together with $R^2$ forms trimethylene or $R^4$ and $R^3$ taken together with the carbon atom to which both $R^4$ and $R^3$ are attached form $(C_{3-8})$cycloalkylene or $(C_{3-8})$heterocycloalkylene, wherein said $(C_{3-8})$cycloalkylene or $(C_{3-8})$heterocycloalkylene optionally is substituted with $(C_{1-6})$alkyl.

A preferred aspect of the invention are the compounds of Formula I in which:

$R^1$ is a group Formula (a), wherein within Formula (a):
$X^1$ is —C(O)—;
$R^5$ is hydrogen or as defined together with $R^9$;
$R^7$ is hydrogen;
$R^9$ is (i) $(C_{1-6})$alkyl or
$R^9$ and $R^5$ together with the carbon atom to which both $R^9$ and $R^5$ are attached form $(C_{3-8})$cycloalkylene or $(C_{3-8})$heterocycloalkylene; and
$R^{11}$ is —$X^4X^5R^{18}$, wherein $X^4$ is —C(O)— and $R^{18}$ is $(C_{6-12})$aryl$(C_{0-6})$alkyl or hetero$(C_{5-12})$aryl$(C_{0-6})$alkyl, wherein said aryl or heteroaryl ring may be substituted by —$R^{22}$, —$X^3OR^{22}$, —$X^3NR^{22}R^{23}$, —$X^3NR^{17}C(O)R^{16}$, —$X^3NR^{23}C(O)OR^{22}$, —$X^3NR^{23}S(O)_2R^{22}$, —$X^3S(O)_2R^{22}$, —$X^3C(O)R^{22}$ or —$X^3NR^{23}C(O)NR^{22}R^{23}$, wherein $X^3$ is a bond or $(C_{1-6})$alkylene, $R^{22}$ is hetero$(C_{3-12})$cycloalkyl$(C_{0-6})$alkyl and $R^{23}$ at each occurrence independently is hydrogen or $(C_{1-6})$alkyl; wherein within $R^{11}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^3NR^{12}R^{12}$, —$X^3NR^{12}C(O)OR^{12}$, —$X^3NR^{12}C(O)NR^{12}R^{12}$, —$X^3NR^{12}C(NR^{12})NR^{12}R^{12}$, —$X^3OR^{12}$, —$X^3SR^{12}$, —$X^3C(O)OR^{12}$, —$X^3C(O)NR^{12}R^{12}$, —$X^3S(O)_2NR^{12}R^{12}$, —$X^3P(O)(OR^3)OR^{12}$, —$X^3OP(O)(OR^3)OR^{12}$, —$X^3NR^{12}C(O)R^{13}$, —$X^3S(O)R^{13}$, —$X^3S(O)_2R^{13}$ and —$X^3C(O)R^{13}$, wherein $X^3$ is a bond or $(C_{1-6})$alkylene, $R^{12}$ at each occurrence independently is hydrogen, $(C_{1-6})$alkyl or halo-substituted $(C_{1-3})$alkyl and $R^{13}$ is $(C_{1-6})$alkyl or halo-substituted $(C_{1-3})$alkyl;

$R^3$ is hydrogen or as defined together with $R^4$; and $R^4$ is (i) hydrogen or $R^4$ and $R^3$ taken together with the carbon atom to which both $R^4$ and $R^3$ are attached form $(C_{3-8})$cycloalkylene or $(C_{3-8})$heterocycloalkylene, wherein said $(C_{3-8})$cycloalkylene or $(C_{3-8})$heterocycloalkylene optionally is substituted with $(C_{1-6})$alkyl.

A preferred aspect of the invention are the compounds of Formula I in which:

$R^1$ is a group Formula (a), wherein within Formula (a):
$X^1$ is —C(O)—;
$R^5$ is hydrogen or as defined together with $R^9$;
$R^7$ is hydrogen;
$R^9$ is (i) $(C_{1-6})$alkyl or
$R^9$ and $R^5$ together with the carbon atom to which both $R^9$ and $R^5$ are attached form $(C_{3-8})$cycloalkylene or $(C_{3-8})$heterocycloalkylene; and
$R^{11}$ is —$X^4X^5R^{18}$, wherein $X^4$ is —C(O)— and $R^{18}$ is phenyl, wherein said phenyl ring may be substituted by —$R^{22}$, —$X^3OR^{22}$, —$X^3NR^{22}R^{23}$, —$X^3NR^{17}C(O)R^{16}$, —$X^3NR^{23}C(O)OR^{22}$, —$X^3NR^{23}S(O)_2R^{22}$, —$X^3S(O)_2R^{22}$, —$X^3C(O)R^{22}$ or —$X^3NR^{23}C(O)NR^{22}R^{23}$, wherein $X^3$ is a bond or $(C_{1-6})$alkylene, $R^{22}$ is hetero$(C_{3-12})$cycloalkyl$(C_{0-6})$alkyl and $R^{23}$ at each occurrence independently is hydrogen or $(C_{1-6})$alkyl; wherein within $R^{11}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^3NR^{12}R^{12}$, —$X^3NR^{12}C(O)OR^{12}$, —$X^3NR^{12}C(O)NR^{12}R^{12}$, —$X^3NR^{12}C(NR^{12})NR^{12}R^{12}$, —$X^3OR^{12}$, —$X^3SR^{12}$, —$X^3C(O)OR^{12}$, —$X^3C(O)NR^{12}R^{12}$, —$X^3S(O)_2NR^{12}R^{12}$, —$X^3P(O)(OR^3)OR^{12}$, —$X^3OP(O)(OR^3)OR^{12}$, —$X^3NR^{12}C(O)R^{13}$, —$X^3S(O)R^{13}$, —$X^3S(O)_2R^{13}$ and —$X^3C(O)R^{13}$, wherein $X^3$ is a bond or $(C_{1-6})$alkylene, $R^{12}$ at each occurrence independently is hydrogen, $(C_{1-6})$alkyl or halo-substituted $(C_{1-3})$alkyl and $R^{13}$ is $(C_{1-6})$alkyl or halo-substituted $(C_{1-3})$alkyl;

$R^3$ is hydrogen or as defined together with $R^4$; and $R^4$ is (i) hydrogen or $R^4$ and $R^3$ taken together with the carbon atom to which both $R^4$ and $R^3$ are attached form $(C_{3-8})$cycloalkylene or $(C_{3-8})$heterocycloalkylene, wherein said $(C_{3-8})$cycloalkylene or $(C_{3-8})$heterocycloalkylene optionally is substituted with $(C_{1-6})$alkyl.

Reference to the preferred embodiments set forth above is meant to include all combinations of particular and preferred groups.

Further preferred are compounds of Formula I selected from a group consisting of:

N-[1-(cyanomethyl-carbamoyl)-3-methyl-butyl]-3-[3-(3-morpholin-4-yl-propyl)-ureido]-benzamide; and N-[1-(cyanomethyl-carbamoyl)-3-methyl-butyl]-3-(3-pyridin-2-yl-ureido)-benzamide;

N-[1S-(cyanomethyl-carbamoyl)-3-methyl-butyl]4-(3-pyridin4-ylmethyl-ureido)-benzamide;

N-[1-(cyanomethyl-carbamoyl)-3-methyl-butyl]4-(3-piperidin-4-yl-ureido)-benzamide;

N-[1-S-(dicyanomethyl-carbamoyl)-3-methyl-butyl]-4-morpholin-4-yl-benzamide;

4-dimethylamino-piperidine-1-carboxylic acid {4-[1-(cyanomethyl-carbamoyl)3-methyl-butylcarbamoyl]-phenyl}-amide;
N-[1S-cyanomethylcarbamoyl-3-methylbutyl)-4-(4-methylpiperazin-1-yl)benzamide;
N-[1-cyanomethylcarbamoyl-3-methylbutyl-4-(2-guanidinothiazol-4-yl)]benzamide;
{4-[1-S-(cyanomethyl-carbamoyl)-3-methyl-butylcarbamoyl]-phenyl}-carbamic acid 3-pyridin-4-yl-propyl ester; and
N-[1-(cyanomethyl-carbamoyl)-3-methyl-butyl]-{-4-3-[2-(3H-imidazol-4-yl)-ethyl]-ureido}-benzamide.

A preferred aspect of the invention are the compounds of Formula II in which:

$X^1$ is selected from —C(O)—;

$R^1$ and $R^2$ both are hydrogen;

$R^3$ is isobutyl and $R^4$ is hydrogen or $R^3$ and $R^4$ taken together with the carbon atom to which both $R^3$ and $R^4$ are attached form cyclopropylene or cyclohexylene;

$R^5$ and $R^6$ both are hydrogen or $R^5$ and $R^6$ taken together with the carbon atom to which both $R^5$ and $R^6$ are attached form cyclohexylene or $(C_6)$ heterocycloalkylene; and $R^7$ is —$X^2X^3R^9$, wherein $X^2$ is —C(O)—, $X^3$ is a bond and $R^9$ is phenyl, wherein within $R^9$ said phenyl is substituted by —$R^{12}$, —$X^4NR^{11}R^{12}$, —$X^4NR^{11}C(O)R^{12}$, —$X^4NR^{11}C(O)OR^{12}$, —$X^4NR^{11}C(O)NR^{11}R^{12}$, —$X^4NR^{11}C(NR^{11})NR^{11}R^{12}$, —$X^4OR^{12}$, —$X^4SR^{12}$, —$X^4S(O)R^{12}$, —$X^4S(O)_2R^{12}$, —$X^4C(O)R^{12}$, —$X^4C(O)OR^{12}$, —$X^4OC(O)R^{12}$, —$X^4C(O)NR^{11}R^{12}$, —$X^4OC(O)NR^{11}R^{12}$, —$X^4S(O)_2NR^{11}R^{12}$, —$X^4P(O)(OR^{11})OR^{12}$ or —$X^4OP(O)(OR^{11})OR^{12}$, wherein $X^4$ is a bond or $(C_{1-6})$alkylene, $R^{11}$ at each occurrence is hydrogen or $(C_{1-6})$alkyl and $R^{12}$ is hetero$(C_{3-6})$cycloalkyl$(C_{0-6})$alkyl, phenyl$(C_{0-6})$alkyl or hetero$(C_{5-6})$aryl$(C_{0-6})$alkyl, wherein within $R^{12}$ said heterocycloalkyl, phenyl or heteroaryl is substituted by —$R^{13}$, —$X^4NR^{11}R^{13}$, —$X^4NR^{11}C(O)R^{13}$, —$X^4NR^{11}C(O)OR^{13}$, —$X^4NR^{11}C(O)NR^{11}R^{13}$, —$X^4NR^{11}C(NR^{11})NR^{11}R^{13}$, —$X^4OR^{13}$, —$X^4SR^{13}$, —$X^4S(O)R^{13}$, —$X^4S(O)_2R^{13}$, —$X^4C(O)R^{13}$, —$X^4C(O)OR^{13}$, —$X^4OC(O)R^{13}$, —$X^4C(O)NR^{11}R^{13}$, —$X^4OC(O)NR^{11}R^{13}$, —$X^4S(O)_2NR^{11}R^{13}$, —$X^4P(O)(OR^{11})OR^{13}$ or —$X^4OP(O)(OR^{11})OR^{13}$, wherein $X^4$ and $R^{11}$ are as defined above and $R^{13}$ is $(C_{3-6})$cycloalkyl$(C_{0-6})$alkyl, hetero$(C_{3-6})$cycloalkyl$(C_{0-6})$alkyl, phenyl$(CO_6)$alkyl or hetero$(C_{5-6})$aryl$(C_{0-6})$alkyl, wherein within $R^7$ any alicyclic and aromatic rings present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^5NR^{14}R^{14}$, —$X^5NR^{14}C(O)OR^{14}$, —$X^5NR^{14}C(O)NR^{14}R^{14}$, —$X^5NR^{14}C(NR^{14})NR^{14}R^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^5)OR^{14}$, —$X^5OP(O)(OR^5)OR^{14}$, —$X^5NR^{14}C(O)R^{15}$, —$X^5S(O)R^{15}$, —$X^5S(O)_2R^{15}$ and —$X^5C(O)R^{15}$, wherein $X^5$ is a bond or $(C_{1-6})$alkylene, $R^{14}$ at each occurrence independently is hydrogen, $(C_{1-6})$alkyl or halo-substituted $(C_{1-3})$alkyl and $R^{15}$ is $(C_{1-6})$alkyl or halo-substituted $(C_{1-3})$alkyl.

Further preferred are compounds of Formula II selected from a group consisting of:

N-(1S-cyanomethylcarbamoyl-3-methylbutyl)-4-(2-pyrid-4-ylamino)thiazol-4-ylbenzamide;

4-[3-(1-benzylpiperidin-4-yl)ureido]-N-(1S-cyanomethylcarbamoyl-3-methylbutyl)benzamide;
N-(1S-cyanomethylcarbamoyl-3-methylbutyl)-4-[4-(2-morpholin-4-ylethyl)piperazin-1-yl]benzamide;
N-(1S-cyanomethylcarbamoyl-3-methylbutyl)-4-(2-pyrid-4-ylthiazol-4-yl)benzamide;
4-[3-(1-benzylpyrrolidin-3S-yl)-3-methylureido]-N-(1S-cyanomethylcarbamoyl-3-methylbutyl)benzamide;
N-(1S-cyanomethylcarbamoyl-3-methylbutyl)-4-(4-pyrid4-ylpiperazin-1-yl)benzamide;
N-(1S-cyanomethylcarbamoyl-3-methylbutyl)-4-[2-(1-methylpyridin-4-ylamino)thiazol4-yl]benzamide;
N-(1S-cyanomethylcarbamoyl-3-methylbutyl)-4-[2-(1-methylpyridin-4-yl)thiazol-4-yl]benzamide;
N-[(S)-1-(Cyanomethyl-carbamoyl)-3-methyl-but-3-enyl]-4-[2-(pyridin-4-ylamino)-thiazol-4-yl]-benzamide;
N-(1S-cyanomethylcarbamoyl-3-methylbutyl)-4-[2-(1-allylpyrid-4-yl)thiazol-4-yl]benzamide;
N-(1S-Cyanomethylcarbamoyl-3-methylbutyl)-4-(2-piperidin-4ylaminothiazol-4-yl)benzamide;
N-(1S-cyanomethylcarbamoyl-3-methylbutyl)-4-(2-piperazin-1-ylthiazol4-yl)benzamide;
N-(1S-cyanomethylcarbamoyl-3-methylbutyl)-4-[2-(4-methylpiperazin-1-yl)thiazol4-yl]benzamide;
N-[1S-(1-cyanocyclopropylcarbamoyl)-3-methylbutyl]-4-(2-piperazin-1-yl-thiazol-4-yl)benzamide;
N-[1S-(1-cyanocyclopropylcarbamoyl)-3-methylbutyl]-4-[2-(4-methylpiperazin-1-yl)thiazol-4-yl]benzamide;
N-[1S-(1-cyanocyclopropylcarbamoyl)-3-methylbutyl]-4-(2-piperidin-4-ylaminothiazol4-yl)benzamide;
N-(1-cyanomethylcarbamoylcyclohexyl)-4-(2-piperazin-1-ylthiazol4-yl)benzamide;
N-[1-(Cyanomethyl-carbamoyl)cyclohexyl]-4-[2-(piperidin-4-ylamino)-thiazol-4-yl]-benzamide;
N-(1R-cyanomethylcarbamoyl-3-methylbutyl)-4-(2-molpholin-4-ylthiazol4-yl)benzamide;
N-(1-Cyanomethylcarbamoylcyclohexyl)-4-[2-(4-methylpiperazin-1-yl)thiazol-4-yl]benzamide;
N-[1-(4-cyanotetrahydropyran-4-ylcarbamoyl)cyclohexyl]-4-[2-(4-methylpiperazin-1-yl)thiazol-4-yl]benzamide;
N-(1-cyanomethylcarbamoylcyclohexyl)-4-(2-morpholin-4-ylthiazol-4-yl)benzamide;
N-(1-cyanomethylcarbamoylcyclohexyl)-4-(2-piperazin-1-ylmethylthiazol-4-yl)benzamide;
tert-butyl 4-(4-{4-[1S-(1-cyanocyclopropylcarbamoyl)-3-methylbutylcarbamoyl]phenyl}thiazol-2-ylmethyl)piperazine-1-carboxylate;
N-[(S)-1-(1-Cyano-cyclopropylcarbamoyl)-3-methyl-butyl]-4-(2-piperazin-1-ylmethyl-thiazol-4-yl)-benzamide; and
N-(1S-cyanomethylcarbamoyl-3-methylbutyl)-4-(4-morpholin-4-ylmethylthiazol-2-ylamino)benzamide.

Pharmacology and Utility

The compounds of the invention are cysteine protease inhibitors, in particular the compounds of the invention inhibit the activity of cathepsins B, L, K and/or S and, as such, are useful for treating diseases in which cathepsin B, L, K and/or S activity contributes to the pathology and/or symptomatology of the disease. For example, the compounds of the invention are useful in treating tumor invasion and metastasis, in particular as anti-angiogenic agents, rheumatoid arthritis, osteo arthritis, pneumocystis carinii, acute pancreatitis, inflammatory airway disease and bone and joint disorders. Furthermore, the compounds of the invention are useful in treating bone resorption disorders, e.g., osteoporosis. The compounds of the invention also are useful in treating autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis, allergic disorders, including, but not limited to asthma, and allogeneic immune responses, including, but not limited to, organ transplants or tissue grafts.

The cysteine protease inhibitory activities of the compounds of the invention can be determined by methods known to those of ordinary skill in the art. Suitable in vitro assays for measuring protease activity and the inhibition thereof by test compounds are known. Typically, the assay measures protease induced hydrolysis of a peptide based substrate. Details of assays for measuring protease inhibitory activity are set forth in Examples 10, 11, 12 and 13, infra.

Nomenclature

The compounds of Formula I and the intermediates and starting materials used in their preparation. The compounds of Formula I and the intermediates and starting materials used in their preparation are named in accordance with IUPAC rules of nomenclature in which the characteristic groups have decreasing priority for citation as the principle group as follows: acids, esters, amides, etc.. Alternatively, the compounds are named by AutoNom 4.0 (Beilstein Information Systems, Inc.). For example, a compound of Formula I in which $R^1$ is benzyloxycarbonylaminobutyryl and $R^2$, $R^3$ and $R^4$ are each hydrogen; that is, a compound having the following structure:

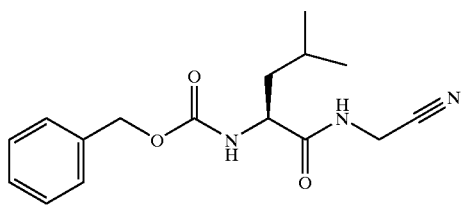

is named benzyl (S)-1-cyanomethylcarbamoyl-3-methylbutylcarbamate or [(S)-1-(cyanomethyl-carbamoyl)-3-methyl-butyl]-carbamic acid benzyl ester; and a compound of Formula I in which $R^1$ is 4-(2-meth-4-ylthiazolyl)benzoylaminobutyryl and $R^2$, $R^3$ and $R^4$ are each hydrogen; that is, a compound having the following structure:

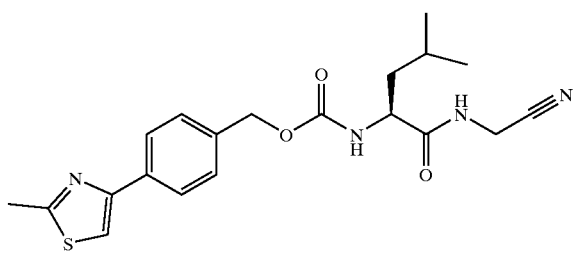

is named N-(1-cyanomethylcarbamoyl-3-methylbutyl)-4-(2-methylthiazol-4-yl)benzamide or N-[(S)-1-(cyanomethyl-carbamoyl)-3-methyl-butyl]-4-(2-methyl-thiazol-4-yl)-benzamide; and a compound of Formula I in which $R^1$ is 4-(2-meth-4-ylthiazolyl)benzoylaminobutyryl and $R^2$, $R^3$ and $R^4$ are each hydrogen; that is, a compound having the following structure:

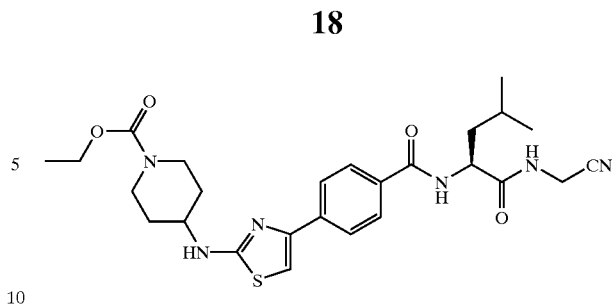

is named ethyl 4-{4-[4-(1S-cyanomethylcarbamoyl-3-methylbutylcarbamoyl)phenyl]thiazol-2-ylamino}piperidine-1-carboxylate or 4-(4-{4-[(S)-1-(cyanomethyl-carbamoyl)-3-methyl-butylcarbamoyl]-phenyl}-thiazol-2-ylamino)-piperidine-1-carboxylic acid ethyl ester.

Administration and Pharmaceutical Compositions

In general, compounds of Formula I will be administered in therapeutically effective to amounts via any of the usual and acceptable modes known in the art, either singly or in combination with another therapeutic agent. A therapeutically effective amount may vary widely depending on the severity of the disease, the age and relative health of the subject, the potency of the compound used and other factors. For example, therapeutically effective amounts of a compound of Formula I may range from 0.1 micrograms per kilogram body weight (µg/kg) per day to 10 milligram per kilogram body weight (mglkg) per day, typically 1 µg/kg/day to 1 mg/kg/day. Therefore, a therapeutically effective amount for a 80 kg human patient may range from 10 µg/day to 100 mg/day, typically 0.1 mg/day to 10 mg/day. In general, one of ordinary skill in the art, acting in reliance upon personal knowledge and the disclosure of this Application, will be able to ascertain a therapeutically effective amount of a compound of Formula I for treating a given disease.

The compounds of Formula I can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, etc.). Preferred liquid carriers, particularly for injectable solutions, include water, saline, aqueous dextrose and glycols.

The amount of a compound of Formula I in the composition may vary widely depending upon the type of formulation, size of a unit dosage, kind of excipients and other factors known to those of skill in the art of pharmaceutical sciences. In general, a composition of a compound of Formula I for treating a given disease will comprise from 0.01% w to 10% w, preferably 0.3% w to 1% w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula I are described in Example 17.

The compounds of Formula I can be administered alone or in combination with other compounds of Formula I or in combination with one or more other active ingredient(s). For example, the compounds of Formula I can be administered in combination with a therapeutically active amount of a bisphosphonic acid or acid ester derivative or any pharmaceutically acceptable salt thereof. Suitable bisphosphonic acids and acid ester derivatives include compounds corresponding to the following formula:

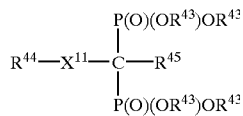

wherein $X^{11}$ is a bond or $(C_{1-7})$alkylene, each $R^{43}$ independently is hydrogen or $(C_{1-30})$alkyl, $R^{44}$ and $R^{45}$ are selected independently from a group consisting of hydrogen, halo, optionally substituted $(C_{1-30})$alkyl, $(C_{3-30})$cycloalkyl, hetero$(C_{5-30})$cycloalkyl, optionally substituted $(C_{6-10})$aryl, hetero$(C_{6-10})$aryl, $-NR^{46}R^{46}$, $-OR^{46}$, $-SR^{46}$, wherein each $R^{46}$ independently is hydrogen, $(C_{1-10})$alkyl, $(C_{3-10})$cycloalkyl, optionally substituted $(C_{6-10})$aryl, provided that both $R^{44}$ and $R^{45}$ are not selected from hydrogen or hydroxy when $X^{11}$ is a bond; or $R^{44}$ and $R^{45}$ taken together form $(C_{2-9})$alkylene; wherein $(C_{3-10})$cycloalkyl includes adamantyl and the like, hetero$(C_{5-10})$cycloalkyl includes pyrrolidinyl and the like, $(C_{6-10})$aryl includes phenyl and naphthyl, and hetero$(C_{6-10})$aryl includes quinolyl, isoquinolyl, pyridyl, furyl, imidazolyl, imidazopyridyl and the like.

Instances wherein $R^{44}$ and/or $R^{45}$ are substituted $(C_{1-30})$alkyl may include, but are not limited to, $(C_{1-30})$alkyl substituted by hetero$(C_{5-10})$cycloalkyl, $(C_{6-10})$aryl, hetero$(C_{6-10})$aryl, $-NR^{47}R^{47}$, $-OR^{47}$ and $-SR^{47}$, wherein each $R^{47}$ is independently hydrogen or $(C_{1-10})$alkyl; wherein hetero$(C_{5-10})$cycloalkyl includes pyrrolidinyl and the like, $(C_{6-10})$aryl includes phenyl and naphthyl, and hetero$(C_{6-10})$aryl includes quinolyl, isoquinolyl, pyridyl, furyl, imidazolyl, imidazopylidyl and the like. Suitable optionally substituted aryl groups include, but are not limited to, halo-substituted phenyl.

A non-limiting class of bisphosphonic acids and acid ester derivatives thereof suitable for administration in combination with compounds of Formula I include those in which $R^{44}$ is selected from the group consisting of hydrogen, hydroxy or halo, and $R^{45}$ is selected from the group consisting of optionally substituted $(C_{1-30})$alkyl, halo and $-SR^{46}$, wherein $R^{46}$ is $(C_{1-10})$alkyl or phenyl.

A non-limiting subclass of bisphosphonic acids and acid ester derivatives thereof suitable for administration in combination with compounds of Formula I include those in which $R^{44}$ is selected from the group consisting of hydrogen, hydroxy and chloro and $R^{45}$ is selected from the group consisting of optionally substituted $(C_{1-30})$alkyl, chloro and chlorophenylthio.

A non-limiting example of a bisphosphonic acid suitable for administration in combination with compounds of Formula I include that in which $X^{11}$ is a bond, each $R^{43}$ is hydrogen, $R^{44}$ is hydroxy and $R^{45}$ is 3-aminopropyl, namely 4-amino-1-hydroxybutylidene-1,1-bisphosphonic acid (aka alendronic acid), or the monosodium trihydrate salt thereof, namely 4-amino-1-hydroxybutylidene-1,1-bisphosphonate monosodium trihydrate (aka alendronate monosodium trihydrate), described in U.S. Pat. No. 4,922,007, to Kieczykowski et al., issued May 1, 1990; U.S. Pat. No. 5,019,651, to Kieczykowski et al., issued May 28, 1991; U.S. Pat. Nos. 5,510,517, to Dauer et al., issued Apr. 23, 1996; U.S. Pat. No. 5,648,491, to Dauer et al., issued Jul. 15, 1997, all of which patents are incorporated by reference herein in their entirety.

Further nonlimiting examples of bisphosphonic acids suitable for administration in combination with compounds of Formula I include the following:

cycloheptylaminomethylene-1,1-bisphosphonic acid (aka cimadronic acid), described in U.S. Pat. No. 4,970,335, to Isomura et al., issued Nov. 13, 1990;

1,1-dichloromethylene-1,1diphosphonic acid (aka clodronic acid) and the disodium salt thereof, namely clodronate disodium, described in Belgium Patent 672,205 (1966) and *J. Org. Chem* 32, 4111 (1967);

1-hydroxy-3-pyrrolidin-1-ylpropylidene-1,1-bisphosphonic acid (aka EB-1053);

1-hydroxyethylidene-1,1-diphosphonic acid (aka etidronic acid);

1-hydroxy-3-(N-methyl-N-pentylamino)propylidene-1,1-bisphosphonic acid (aka ibandronic acid), described in U.S. Pat. No. 4,927,814, issued May 22, 1990;

6-amino-1-hydroxyhexylidene-1,1-bisphosphonic acid (aka zolendronic acid);

3-(dimethylamino)-1-hydroxypropylidene-1,1-bisphosphonic acid (aka olpadronic acid);

3-amino-1-hydroxypropylidene-1,1-bisphosphonic acid (aka pamidronic acid);

2-pyrid-2-ylethylidene-1,1-bisphosphonic acid (aka piridronic acid), described in U.S. Pat. No. 4,761,406;

1-hydroxy-2-pyrid-3-ylethylidene-1,1-bisphosphonic acid (aka risedronic acid);

4-chlorophenylthiomethylenebisphosphonic acid (aka tiludronic acid), described in U.S. Pat. No. 4,876,248, to Breliere et al., Oct. 24, 1989; and 1-hydroxy-2-(1H-imidazol-1-yl)ethylidene-1,1-bisphosphonic acid (aka zoledronic acid); all of which patents and other documents referred to above are incorporated by reference herein in their entirety.

A non-limiting subclass of bisphosphonic acids suitable for administration in combination with compounds of Formula I include those selected from the group consisting of alendronic acid, cimadronic acid, clodronic acid, tiludronic acid, etidronic acid, ibandronic acid, risedronic acid, piridronic acid, pamidronic acid, zolendronic acid, pharmaceutically acceptable salts thereof, and mixtures thereof. A further example of a bisphosphonic acid suitable for administration in combination with compounds of Formula I is alendronic acid or a pharmaceutically acceptable salt thereof, and mixtures thereof. A further non-limiting example is alendronate monosodium trihydrate.

Compounds of Formula I can be administered in combination with a therapeutically active amount of an estrogen receptor agonist. Non-limiting examples of estrogen receptor agonists suitable for administration in combination with the compounds of Formula I include naturally occurring estrogens such as estradiol, estrone and estroil, or synthetic estrogen receptor agonists such as [6-hydroxy-2-(4- hydroxyphenyl)benzo[b]thien-3-yl][4-(2-piperidin-1-ylethoxy)phenyl]methanone (aka raloxifene) and {2-[4-(1,2-diphenylbut-1-enyl)phenoxy]ethyl}dimethylamine (aka tamoxifen). A non-limiting subclass of estrogen receptor agonists suitable for administration in combination with the compounds of Formula I include estrogen receptor partial agonists (i.e., estrogen receptor agonists with mixed agonist/antagonist properties), sometimes referred to as estrogen receptor modulators. Estrogen receptor partial agonists can exert tissue-selective estrogen agonist effects. Tamoxifen, for example, selectively exerts an estrogen agonist effect on the bone, in humans. Additional suitable estrogen receptor partial agonists are described in Tissue-Selective Actions Of Estrogen Analogs, Bone Vol. 17, No. 4, October 1995, 181S–190S. Certain 3-[4-(2-phenylindol-1-ylmethyl)phenyl]acrylamides, described in U.S. Pat. No. 5,985,910 to Miller et al., Nov. 16, 1999; benzothiphene compounds, described in U.S. Pat. No. 5,985,897 to Meuhl et al., Nov. 16, 1999; naphthyl compounds, described in U.S. Pat. No. 5,952,350 to Cullinan et al., Sep. 14, 1999; substituted benzothiophene compounds, described in U.S. Pat. No. 5,962,475 to Schmid et al., Oct. 4, 1999, are suitable estrogen receptor partial agonists for administration with the compounds of Formula I; all of which patents and other documents referred to above are incorporated by reference herein in their entirety.

More particularly a pharmaceutical composition of this invention may comprise a therapeutically effect amount of a compound of Formula I in combination with one or more active ingredient(s) selected from the group consisting of (i) a therapeutically effect amount of a bisphosphonic acid or acid ester thereof or a pharmaceutically acceptable salt thereof and (ii) a therapeutically effect amount of an estrogen receptor agonist or a pharmaceutically acceptable salt thereof; and one or more pharmaceutically acceptable excipient(s). Non-limiting examples of such bisphosphonic acids include 1,1-dichloromethylene-1,1-diphosphonic acid, 1-hydroxy-3-pyrrolidin-1-ylpropylidene-1,1-bisphosphonic acid, 1-hydroxyethylidene-1,1-diphosphonic acid, 1-hydroxy-3-(N-methyl-N-pentylamino)propylidene-1,1-bisphosphonic acid, 6-amino-1-hydroxyhexylidene-1,1-bisphosphonic acid, 3-(dimethylamino)-1-hydroxypropylidene-1,1-bisphosphonic acid, 3-amino-1-hydroxypropylidene-1,1-bisphosphonic acid, 2-pyrid-2-ylethylidene-1,1-bisphosphonic acid, 1-hydroxy-2-pyrid-3-ylethylidene-1,1-bisphosphonic acid, 4-chlorophenylthiomethylenebisphosphonic acid and 1-hydroxy-2-(1H-imidazol-1-yl)ethylidene-1,1-bisphosphonic acid or acid ester thereof or a pharmaceutically acceptable salt thereof; particularly 1,1-dichloromethylene-1,1-diphosphonic acid or a pharmaceutically acceptable salt thereof and preferably 1,1-dichloromethylene-1,1-diphosphonate monosodium trihydrate.

Chemistry

Processes for Making Compounds of Formula I

Compounds of Formula I can be prepared by proceeding as in the following Scheme 1:

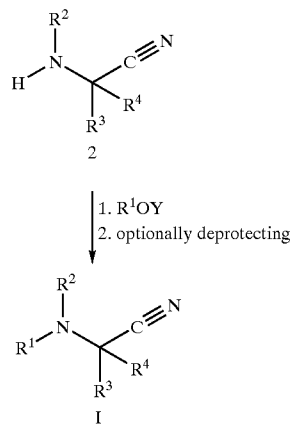

Scheme 1 in which Y is hydrogen or an activating group (e.g., 2,5-dioxopyrrolidin-1-yl (NBS), and the like) and each $R^1$, $R^2$, $R^3$ and $R^4$ are as defined in the Summary of the Invention.

Compounds of Formula I can be prepared by reacting a compound of Formula 2, or a protected derivative thereof, with a compound of the formula $R^1OY$, or a protected derivative thereof, and then optionally deprotecting. The reaction is carried out in the presence of a suitable acylation catalyst (e.g., triethylamine) and in a suitable solvent (e.g., acetonitrile, N,N-dimethyformamide (DMF), methylene chloride, or any suitable combination thereof) at 10 to 30° C., preferably at about 25° C., and requires 24 to 30 hours to complete. When Y is hydrogen the reaction can be effected in the presence of a suitable coupling agent (e.g., benzotriazole-1-yloxytrispyrrolidinophosphonium hexafluorophosphate (PyBOP®), 1-(3-dimethylaminopropyl)-3-ethylcarbodiimide hydrochloride (EDC), O-benzotriazol-1-yl-N,N,N',N'-tetramethyluronium hexafluorophosphate (HBTU), 1,3-dicyclohexylcarbodiimide (DCC), or the like) and base (e.g., N,N-diisopropylethylamine, triethylamine, or the like) and requires 2 to 15 hours to complete. Alternatively, when Y is hydrogen the reaction can be carried out by treating the compound of formula $R^1OH$ with N-methylmorpholine and isobutyl chloroformate in a suitable solvent (e.g., TBF, or the like) at between 0 and 5° C. for 30 minutes to an hour and then introducing the compound of Formula 2 to the reaction mixture and allowing the reaction to proceed for 12 to 15 hours.

Deprotection can be effected by any means which removes the protecting group and gives the desired product in reasonable yield. A detailed description of the techniques applicable to the creation of protecting groups and their removal can be found in T. W. Greene, *Protecting Groups in Organic Synthesis*, John Wiley & Sons, Inc. 1981. A detailed description of the preparation of a compound of Formula I according to Scheme 1 is set forth in Examples 4, 5, 6 and 8, infra.

Alternatively, compounds of Formula I can be prepared by reacting a compound of Formula 2 with a compound of the formula $R^1$-SS, wherein SS is a suitable solid support (e.g., thiophenol resin, or the like). The reaction can be carried out in the presence of a suitable acylation catalyst (e.g., 4-dimethylaminopyridine, or the like) and in a suitable solvent (e.g., dry pyrimidine, or the like) and requires 60 to 70 hours to complete. A detailed description of the preparation of a compound of Formula I according to the above-described procedures is set forth in Example 9 infra.

Compounds of Formula I can be prepared by proceeding as in the following reaction Scheme 2:

Scheme 2

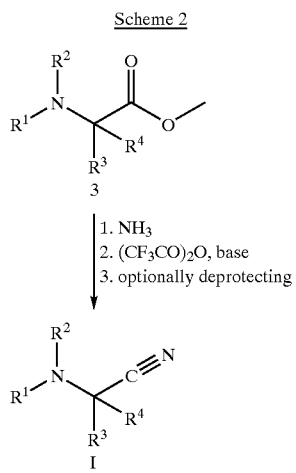

in which each $R^1$, $R^2$, $R^3$ and $R^4$ are as defined in the Summary of the Invention.

Compounds of Formula I can be prepared by treating a compound of Formula 3, or a protected derivative thereof, with ammonia to provide a corresponding amide, then reacting the amide with a suitable dehydrating agent (e.g., trifluoroacetic anhydride, cyanuric chloride, thionyl chloride, phosphonyl chloride, and the like) and optionally deprotecting. The reaction with the ammonia is carried out in a suitable solvent (e.g., methanol) at between 0 and 5° C. and requires 6 to 10 days to complete. The reaction with the dehydrating agent is carried out in the presence of a suitable base (e.g, triethylamine) and in a suitable solvent (e.g., tetrahydrofuran (THF), and the like) at between 0 and 50° C. and requires 1 to 2 hours to complete. A detailed description of the preparation of a compound of Formula I according to Scheme 2 is set forth in Examples 7 and 8, infra.

Additional Processes for Preparing Compounds of Formula I

A compound of Formula I can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula I can be prepared by reacting the free acid form of the compound with a pharmaceutically acceptable inorganic or organic base. Inorganic and organic acids and bases suitable for the preparation of the pharmaceutically acceptable salts of compounds of Formula I are set forth in the definitions section of this application. Alternatively, the salt forms of the compounds of Formula I can be prepared using salts of the starting materials or intermediates.

The free acid or free base forms of the compounds of Formula I can be prepared from the corresponding base addition salt or acid addition salt form. For example, a compound of Formula I in an acid addition salt form can be converted to the corresponding free base by treating with a suitable base (e.g., ammonium hydroxide solution, sodium hydroxide, etc.). A compound of Formula I in a base addition salt form can be converted to the corresponding free acid by treating with a suitable acid (e.g., hydrochloric acid, etc).

The N-oxides of compounds of Formula I can be prepared by methods known to those of ordinary skill in the art. For example, N-oxides can be prepared by treating an unoxidized form of a compound of Formula I with an oxidizing agent (e.g., trifluoroperacetic acid, permaleic acid, perbenzoic acid, peracetic acid, meta-chloroperoxybenzoic acid, etc.) in a suitable inert organic solvent (e.g., a halogenated hydrocarbon such as methylene chloride) at approximately 0° C. Alternatively, the N-oxides of the compounds of Formula I can be prepared from the N-oxide of an appropriate starting material.

Compounds of Formula I in unoxidized form can be prepared from N-oxides of compounds of Formula I by treating with a reducing agent (e.g., sulfur, sulfur dioxide, triphenyl phosphine, lithium borohydride, sodium borohydride, phosphorus trichloride, tribromide, etc.) in an suitable inert organic solvent (e.g., acetonitrile, ethanol, aqueous dioxane, etc.) at 0 to 80° C.

Prodrug derivatives of the compounds of Formula I can be prepared by methods known to those of ordinary skill in the art (e.g., for further details see Saulnier et al.(1994), *Bioorganic and Medicinal Chemistry Letters.* 4:1985). For example, appropriate prodrugs can be prepared by reacting a non-derivatized compound of Formula I with a suitable carbamylating agent (e.g., 1,1-acyloxyalkylcarbonochloridate, para-nitrophenyl carbonate, etc.).

Protected derivatives of the compounds of Formula I can be made by means known to those of ordinary skill in the art. A detailed description of the techniques applicable to the creation of protecting groups and their removal can be found in T. W. Greene, *Protecting Groups in Organic Synthesis*, John Wiley & Sons, Inc. 1981.

Compounds of Formula I can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diasteromeric derivatives of compounds of Formula I, dissociable complexes are preferred (e.g., crystalline diastereoisomeric salts). Diastereomers have distinct physical properties (e.g., melting points, boiling points, solubilities, reactivity, etc.) and can be readily separated by taking advantage of these disimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, Honh Wiley & Sons, Inc. (1981).

In summary, an aspect of the invention is a process for preparing a compound of Formula I, which process comprises:

(A) reacting a compound of Formula 2:

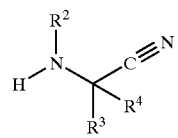

or a protected derivative thereof with a compound of the formula $R^1OY$, or a protected derivative thereof, in which Y is hydrogen or an activating group and each $R^1$, $R^2$, $R^3$ and $R^4$ are as defined in the Summary of the Invention; or (B) reacting a compound of Formula 3:

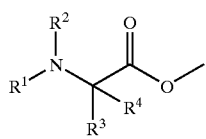

3 with ammonia to provide a corresponding amide and then reacting the amide with trifluoroacetic anhydride, in which each $R^1$, $R^2$, $R^3$ and $R^4$ are as defined in the Summary of the Invention (C) optionally deprotecting a protected derivative of a compound of Formula I to provide a corresponding unprotected derivative;

(D) optionally converting a compound of Formula I into a pharmaceutically acceptable salt;

(E) optionally converting a salt form of a compound of Formula I to non-salt form;

(F) optionally converting an unoxidized form of a compound of Formula I into a pharmaceutically acceptable N-oxide;

(G) optionally converting an N-oxide form of a compound of Formula I its unoxidized form;

(H) optionally converting a non-derivatized compound of Formula I into a pharmaceutically prodrug derivative; and (I) optionally converting a prodrug derivative of a compound of Formula I to its non-derivatized form.

Processes for Preparing Intermediates

Compounds of Formula 2 can be prepared by reacting a compound of Formula 4:

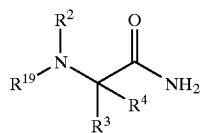

4 in which $R^{19}$ is an amino protecting group and each $R^2$, $R^3$ and $R^4$ are as defined in the Summary of the Invention, with thionyl chloride and then deprotecting. The reaction with the thionyl chloride is carried out in the presence of a suitable base (e.g, triethylamine) and in a suitable solvent (e.g, DMF) at between 0 and 5° C. and requires 30 minutes to an hour to complete. Alternatively, compounds of Formula 2 can be prepared by reacting a compound of Formula 4 with trifluoroacetic anhydride. The deprotection can be effected by any means which removes the protecting group and gives the desired product in reasonable yield. A detailed description of the preparation of a compound of Formula 2 according to above-described procedure is set forth in Example 1, infra.

Compounds of Formula 4 can be prepared by treating a corresponding alkanoyl halide with ammonia. The treatment is carried out in a suitable solvent (e.g., dichloromethane, 5% aqueous sodium carbonate, and the like, or any suitable combination thereof) at 10 to 30° C. and requires 30 minutes to an hour to complete. The alkanoyl halide intermediates can be prepared from the corresponding alkanoic acid by treating with thionyl chloride in a suitable solvent (e.g., dichloromethane) under nitrogen for 30 minutes to an hour. A detailed description of the preparation of a compound of Formula 2 according to the above-described procedures is set forth in Example 1, infra.

Compounds of the formula $R^1$-SS can be prepared by reacting a compound of Formula 5(a) or 5(b):

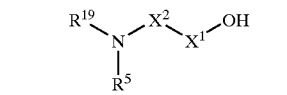

5(a)

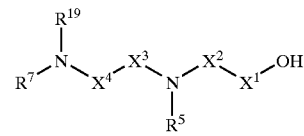

5(b)

in which $R^{19}$ is an amino protecting group (e.g., tert-butoxycarbonyl, fluoren-9-ylmethoxycarbonyl, or the like) and each $X^1$, $X^2$, $X^3$, $R^5$ and $R^7$ are as defined for Formula I in the Summary of the Invention, with a suitable solid support resin (e.g, Wang (4-benzyloxybenzyl alcohol) resin, thiophenol resin, or the like), deprotecting to provide, respectively, a compound of Formula 6(a) or 6(b):

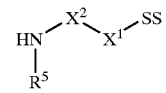

6(a)

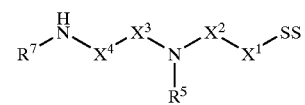

6(b)

in which SS is a solid support and then reacting the compound of Formula 6(a) or 6(b) with a compound of the formula $R^6OH$ (e.g., benzoic acid, indole-5-carboxylic acid, methanesulfonic acid, or the like).

The reaction between the compound of Formula 5(a) or 5(b) and the resin is carried out in the presence of a suitable coupling agent (e.g., benzotriazole-1-yloxytrispyrrolidinophosphonium hexafluorophosphate (e.g., diisopropylcarbodiimide (DIC), PyBOP®, EDC, HBTU, DCC, or the like) and acylation catalyst (e.g., N,N-diisopropylethylamine, triethylamine, 4-dimethylaminopyridine, 1-hydroxybenzotriazole hydrate, or the like) in a suitable solvent (e.g., methylene chloride, DMF, or the like) and requires approximately 3 to 20 hours to complete. Deprotection can be effected by any means which removes the protecting group and gives the desired product in reasonable yield. The reaction between the compound of Formula 6(a) or 6(b) is carried out with a suitable coupling agent and acylation catalyst. A detailed description of the preparation of a compound of the formula $R^1$-SS according to the above-described procedures is set forth in Examples 2(A–C) and 4(A–C), infra.

Compounds of the formula $R^1OH$ can be prepared by treating a compound of formula $R^1$-SS with a suitable acid (e.g., trifluoroacetic acid, or the like) in a suitable solvent (e.g, methylene chloride, or the like). Alternatively, compounds of the formula $R^1OH$ in which $X^1$ is —C(O)—and $X^2$ is —CHR$^9$— can be prepared by alkylating an organometallic compound of Formula 7(a) or 7(b):

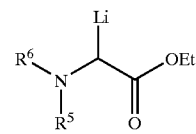

7(a)

-continued

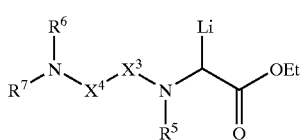

7(b)

with a compound of the formula R⁹L, in which L is a leaving group and each $X^3$, $X^4$, $R^5$, $R^6$, $R^7$ and $R^9$ are as defined for Formula I in the Summary of the Invention, and then converting the resulting ethyl ester to the corresponding acid. The alkylation is carried out in a suitable solvent (e.g., THF) at −78° C. to 0° C. and requires 1 to 2 hours to complete. Conversion the acid can be effected by treating the ester with lithium hydroxide for approximately 15 hours. The organometallic compound is generated by treating a corresponding organo compound with an appropriate base (e.g., N,N-diisopropylethylamine, triethylamine, and the like) and n-butyllithium or tert-butyllithium at −80 to −70° C., preferably at about −78° C., for approximately 30 minutes to an hour. A detailed description of the preparation of a compound of the formula $R^1OH$ according to the above-described procedures is set forth in Example 3, infra.

EXAMPLES
Compounds of Formula 2

Reference 1

2S-Amino-4-phenylbutyronitrile

A mixture comprised of 2S-flouren-9-ylmethoxycarbonylamino-3-phenylpropionic acid (2 g, 5 mmol), thionyl chloride (4 mL) and dichlormethane (10 mL) was refluxed under nitrogen for 30 minutes and then concentrated. The residue was suspended in 50% diethyl ether/hexane. The solids were collected by filtration, rinsed with water and dried (phosphorus pentoxide) in a vacuum desiccator to provide 2S-flouren-9-ylmethoxycarbonylamino-3-phenylpropionyl chloride (1.83 g, 4.35 mmol) as a white solid, m.p. 120–122° C. Proton NMR (300 MHz, CDCl₃): δ7.78 (d, J=7 Hz, 2H), δ7.59 (d, J=7 Hz, 2H), δ7.17–7.45(m, 9 H), δ5.21 (bd, J=7 Hz, 1H), δ4.52 (m, 3H), δ4.26 (t, J=7 Hz, 1H), δ2.73 (m, 2H), δ2.37 (m, 1H), δ2.09 (m, 1H).

A mixture comprised of 2S-flouren-9-ylmethoxycarbonylamino-3-phenylpropionyl chloride (0.484 g, 1.15 mol), dichloromethane (10 mL), 5% aqueous sodium carbonate solution (10 mL) and concentrated aqueous ammonia (84 μL, 1.27 mmol) was stirred vigorously until a white precipitate had formed. The precipitate was collected by filtration, rinsed with water and dried (phosphorus pentoxide) in a vacuum desiccator to provide 2S-flouren-9-ylmethoxycarbonylamino-3-phenylpropionamide (0.375 g, 0.93 mmol) as a white solid, m.p. 159–161° C. (decomp.). Proton NMR (300 MHz, DMSO-d₆): δ7.85 (d, J=7.5 Hz, 2H), δ7.71 (m, 2H), δ7.50 (d, J=8 Hz, 1H), δ6.99–7.40 (m, 10H), δ4.24 (m, 3H), δ3.88 (m, 1H), δ2.46–2.65 (m, 2H), δ1.70–1.94 (m, 2H).

2S-Flouren-9-ylmethoxycarbonylamino-3-phenylpropionamide (0.235 g, 0.59 mmol) was dissolved in cold DMF (5 mL, 0 to 5° C.) and then triethylamine (0.33 mL, 2.35 mmol) and thionyl chloride (0.59 mL, 1.17 mmol) were added to the solution. The mixture was cooled at between 0 and 5° C. for 30 minutes and then methanol (10 drops) was added. The mixture was concentrated in vacuo and the residue was triturated with 50% ethyl acetate/hexanes. The solids were collected by filtration and product was purified by silica gel to chromatography using 20% ethyl acetate/hexanes to provide flouren-9-ylmethyl 1S-cyano-3-phenylpropylcarbamate (94 mg, 0.25 mmol) as a yellow powder, m.p. 110–113° C. Proton NMR (300 MHz, DMSO-d₆): δ8.21 (d, J=7 Hz, 1H), δ7.85 (d, J=7.5 Hz, 2H), δ7.66 (d, J=7.5 Hz, 2H), δ7.14–7.41 (m,9H), δ4.39 (d, J=6 Hz, 3H), δ4.22 (t, J=6 Hz, 1H), δ2.62 (t, J=7.5 Hz, 2H), δ2.00 (apparent q, J=7.5 Hz, 2H). MS (electrospray): mH⁺ 383.

A mixture comprised of flouren-9-ylmethyl 1S-cyano-3-phenylpropylcarbamate (89 mg, 0.23 mmol), piperidine (0.2 mL) and anhydrous DMF (1 mL) was stirred at room temperature for 30 minutes and then concentrated. Product was purified from the residue by silica gel chromatography using 2.5% methanol/dichloromethane to provide 2S-amino-4-phenylbutyronitrile (27 mg, 0.17 mmol) as an oil. Proton NMR (300 MHz, CDCl₃): δ7.25 (m, 5H), δ3.62 (t, J=6 Hz, 1H), δ2.83 (m, 2H), δ2.08 (m, 2H). MS (electrospray): mH⁺ 161 (100%).

Reference 2

2-Benzoylamino-3-(2,6-dichlorophenyl)propionic Acid

A solution comprised of N,N-diisopropylamine (3.97 mL, 22.8 mmol) in dry THF (57 mL) was cooled to −78° C. under nitrogen and then solutions of n-butyl lithium in hexanes (14.25 mL, 22.8 mmol) and ethyl benzoylaminoacetate (2.37 g, 11.4 mmol) in dry THF (23 mL) were added dropwise sequentially. The mixture was stirred for 1 hour and then a solution comprised of 2,6-dichlorobenzyl bromide (1.87 g, 11.4 mmol) in dry TMF (2 mL) was added dropwise. The mixture was stirred for 1 hour at −78° C. and then for 30 minutes while allowing to warm. The mixture then was quenched with water (8 mL) and extracted with ethyl acetate (2×54 mL). The combined extracts were washed with 1M hydrochloric acid (1×27 mL) and saturated sodium chloride solution (1×27 mL), dried (Na₂SO₄) and concentrated on a rotary evaporator. Product was purified from the residue by flash column (silica gel, 10:90 to 50:50 v/v EtOAc-hexane) to provide crude ethyl 2-benzoylamino-3-(2,6-dichlorophenyl)propionate. The propionate ester was treated with lithium hydroxide (118.8 mg, 4.96 mmol) in ethanol (12 mL) and water (50 mL) for 15 hours. The mixture was then diluted with 1M hydrochloric acid (12 mL) and ethyl acetate (24 mL). The aqueous layer was separated and extracted with ethyl acetate (2×4 mL). The combined organic layers were washed with saturated sodium chloride solution (25 mL), dried (Na₂SO₄), filtered and concentrated on a rotary evaporator to provide 2-benzoylamino-3-(2,6-dichlorophenyl)propionic acid.

Reference 3

2S-Benzoylamino-3-(4-benzyloxyphenyl)propionyl-SS

Wang resin (200–400 mesh, 300 mg) was washed twice with dry DMF and then combined with a solution comprised of 3-(4-benzyloxyphenyl)-2-(9H-fluoren-9-ylmethoxycarbonylamino)propionic acid (0.51 g 1.03 mmol, dissolved in a minimal amount of dry DMF), PyBOP® (0.54 g, 1.03 mmol) and N,N-diisopropylethylamine (0.18 mL, 1.03 mmol). The mixture was shaken and then allowed to sit for 3 hours. The resin was separated from the solution phase and washed twice with DMF to provide 3-(4-benzyloxyphenyl)-2-(9H-fluoren-9-ylmethoxycarbonylamino)propionyl-SS.

The 3-(4-benzyloxyphenyl)-2-(9H-fluoren-9-ylmethoxycarbonylamino)propionyl-SS was treated with 20% (v/v) piperidine in DMF in three portions for 3, 7 and 20 minutes while shaking the mixture and removing the solution phase after each treatment. The resin then was washed thrice with DMF and once each with methanol, DMF and methanol and then thrice again with DMF to provide 2-amino-3-(4-benzyloxyphenyl)propionyl-SS.

A mixture comprised of 2-amino-3-(4-benzyloxyphenyl) propionyl-SS was combined with benzoic acid (125.8 mg, 1.03 mmol, dissolved in a minimal amount of dry DMF), PyBOP® (0.54 g, 1.03 mmol) and N,N-diisopropylethylamine (0.18 mL, 1.03 mmol) was shaken and then allowed to sit for 3 hours. The resin was separated, washed twice each with DMF, methanol and methylene chloride to provide 2S-benzoylamino-3-(4-benzyloxyphenyl)propionyl-SS.

Reference 4

4-[2-(4-aminobenzoylamino)-4-methylvaleryloxy]-SS

A solution comprised of 2-tert-butoxycarbonylamino-4-methylvaleric acid monohydrate (7 g, 28 mmol) in toluene (50 mL) was concentrated. The residue was dissolved in methylene chloride and then DIC (4.4 mL, 28 mmol) was added. The mixture was combined with a suspension of thiophenol resin (5 g, 1.4 mmol/g loading) in methylene chloride (50 mL) and then 4dimethylaminopyridine (0.34 g, 2.8 mmol) was added to the mixture. The mixture was shaken for 14 hours and filtered. The resin was washed with twice each with methylene chloride, 15% trimethylamine in methylene chloride and methanol and dried to provide 4-tert-butoxycarbonyl-4-methylvaleryl-SS (6.4 g, 1 mmol/g loading) as a yellow solid.

4-[tert-Butoxycarbonyl-4methylvaleryl-SS (6.6 g) was treated with 50:48:2 (v/v) trifluoroacetic acid/methylene chloride/anisole (50 mL) for one hour. The resin was isolated and washed twice each with methylene chloride, 15% trimethylamine in methylene chloride and methanol and dried to provide 4-[4-methylvaleryloxy]-SS (5.8 g, 1.38 mmol/g loading).

A mixture comprising 4-tert-butoxycarbonylaminomethylbenzoic acid (0.38 g, 1.5 mmol), 1-hydroxybenzotriazole hydrate (0.2 g), HBTU (0.57 g, 1.5 mmol), 4-[4-methylvaleryloxy]-SS (0.4 g, 0.55 mmol), diisopropylethylamine (0.26 mL, 1.5 mmol) and dimethylformamide (10 mL) was sealed in a glass vial, shaken for 16 hours. The resin was isolated by filtering the mixture and washed twice each with dimethylformamide, methylene chloride, methanol and 1,4-dioxane to provide 4-[2-(4-tert-butoxycarbonylaminobenzoylamino)-4-methylvaleryloxy]-SS.

The 4-[2-(4-tert-butoxycarbonylaminobenzoylamino)4-methylvaleryloxy]-SS was treated with 50:48:2 (v/v) trifluoroacetic acid/methylene chloride/anisole to provide 4-[2-(4-aminobenzoylamino)-4-methylvaleryloxy]-SS.

Proceeding as in REFERENCE 4 provided the following compounds:

4-[2-(3-dimethylaminopyrid-4-ylcarbonylamino) valeryloxy]-SS;
4-{2-[6-(1H-imidazol-1-yl)pyrid-3-ylcarbonylamino] valeryloxy}-SS;
4-[2-(6-dimethylaminopyrid-3-ylcarbonylamino) valeryloxy]-SS;
4-{2-[6-(4-methylpiperazin-1-yl)pyrid-3-ylcarbonylamino] valeryloxy}-SS;
4-[2-(2-pyrrolidin-1-ylpyrid-4-ylcarbonylamino) valeryloxy]-SS;
4-[2-(6-morpholin-4-ylpyrid-3-ylcarbonylamino) valeryloxy]-SS;
4-[2-(6-piperidin-1-ylpyrid-3-ylcarbonylamino) valeryloxy]-SS;
4-[2-(6-pyrrolidin-1-ylpyrid-3-ylcarbonylamino) valeryloxy]-SS;
4-[2-(2-piperidin-1-ylpyrid-4-ylcarbonylamino) valeryloxy]-SS;
4-[2-(2-morpholin-4-ylpyrid-4-ylcarbonylamino) valeryloxy]-SS;
4-{2-[2-(1H-imidazol-1-ylpyrid-4-ylcarbonylamino] valeryloxy}-SS;
4-{2-[2-(4-methylpiperazin-1-yl)pyrid-4-ylcarbonylamino] valeryloxy}-SS;
4-[2-(3-dimethylaminomethylbenzoylamino)valeryloxy]-SS;
4-[2-(3-piperidin-1-ylmethylbenzoylamino)valeryloxy]-SS;
4-[2-(4-hydroxy-3-morpholin-4-ylmethylbenzoylamino) valeryloxy]-SS; and
4-[2-(4-tert-butoxycarbonylaminomethylbenzoylamino) valeryloxy]-SS; wherein SS is Wang resin.

Reference 5

2S-Benzoylamino-3-(4-benzyloxyphenyl)propionic Acid 2S-benzoylamino-3-(4-benzyloxyphenyl)propionyl-SS prepared as in Example 3 was treated with 90:10 (v/v) trifluoroacetic acid/methylene chloride for 1 hour. The mixture was filtered and the resin was combined with methylene chloride. The mixture was shaken, allowed to sit 10 minutes and then filtered. The combined filtrates were concentrated on a rotary evaporator to provide crude 2S-benzoylamino-3-(4-benzyloxyphenyl)propionic acid which was used without purification.

Reference 6

2-Amino-N-cyanomethyl-4-methylpentanamide

A solution comprised of 2-tert-butoxycarbonylamino-4-methylvaleric acid (5 g, 30 mmol) in DMF (20 mL) was cooled in an ice bath and then aminoacetonitrile hydrochloride (3 g, 30 mmol), PyBOP® (11.25 g, 21 mmol) and triethylamine (6 mL, 60 mmol) were added sequentially to the solution. The mixture was stirred for 2 hours and then concentrated under vacuum. The residue was partitioned between ethyl acetate (50 mL) and saturated sodium bicarbonate (40 mL). The organic layer was separated, washed with water, 1M hydrochloric acid (20 mL), water and brine, dried (MgSO$_4$) and concentrated under reduced pressure. Product was purified from the residue using a plug of silica with ethyl acetate as the eluant to provide tert-butyl 1-cyanomethylcarbamoyl-3-methylbutylcarbamate.

A mixture comprised of the tert-butyl 1-cyanomethylcarbamoyl-3-methylbutylcarbamate and anhydrous p-toluenesulfonic acid (3 eq.) in methylene chloride (20 mL) was stirred for approximately 12 hours. The mixture was filtered and the solid material collected was triturated several times with ether to remove excess acid and then dried under vacuum to provide 2-amino-N-cyanomethyl-4-methylpentanamide p-toluenesulfonic acid salt.

Example 1

Benzyl (S)-1-cyanomethylcarbamoyl-3-methylbutylcarbamate (Compound 1)

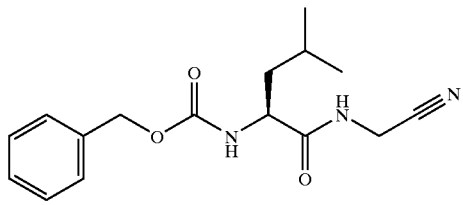

A mixture comprised of 2,5dioxopyrrolidin-1-yl 2-benzyloxycarbonylamino-4-methylvalerate (39.6 g, 0.109 mol), aminoacetonitrile hydrochloride (10.1 g, 0.109 mol), triethylamine (61 mL, 0.436 mol), DMF (40 mL) and acetonitrile (360 mL) was stirred at room temperature for 27 hours. The mixture was filtered, concentrated to a volume of 100 mL and poured into ice water (1000 mL). The mixture was stirred until a precipitate had formed. The precipitate was collected, washed with water and dried. The dry product was recrystallized from 55% ethanol/water (80 mL). The crystals were collected and recrystallized from 65% ethanol/water (70 mL). The crystals were collected and dried to provide benzyl (S)-1-cyanomethylcarbamoyl-3-methylbutylcarbamate (21.1 g, 0.067 mol) as white needles, m.p. 120–121° C. Proton NMR (300 MHz, DMSO-$d_6$): $\delta$8.68 (t, J=6 Hz, 1H), $\delta$7.54 (d, J=8 Hz, 1H), $\delta$7.33 (m, 5H), $\delta$5.00 (Abq, 2H), $\delta$4.09 (d, J=6 Hz, 2H), 4.03 (m, 1H), $\delta$1.24–1.64 (m, 3H), $\delta$0.84 (apparent t, J=7 Hz, 6H). MS (electrospray): mH+303.9 (100%). Calcd. for $C_{16}H_{21}N_3O_3$: C, 63.35; H, 6.98; N, 13.85. Found: C, 63.55; H, 7.01; N, 13.74.

Proceeding as in Example 1 provided the following compounds of Formula I:

benzyl 1S-cyanomethylcarbamoyl-2-methylbutylcarbamate (Compound 2); Proton NMR (300 MHz, DMSO-$d_6$): $\delta$8.72 (bt, 1H), $\delta$7.50 (d, J=8 Hz, 1H), $\delta$7.35 (s, 5H), $\delta$5.02 (s, 2H), $\delta$4.13 (m, 2H), $\delta$3.85 (apparent t, 1H), $\delta$1.75 (m, 1H), $\delta$1.42 (m, 1H), $\delta$1.14 (m, 1H), $\delta$0.80 (m, 6H).

Example 2

2-cyanomethylcarbamoylpiperidine-2-carboxylate (Compound 3)

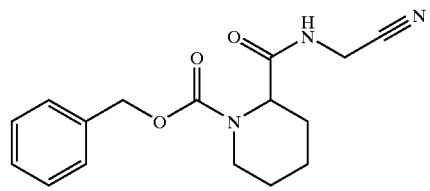

A mixture comprised of 1-benzyloxycarbonylpiperidine-2carboxylic acid (0.425 g, 1.61 mmol), aminoacetonitrile hydrochloride (0.149 g, 1.61 mmol), PyBOP® (0.838 g, 1.61 mmol), N,N-diisopropylethylamine (0.84 mL, 4.83 mmol) and DMF (10 mL) was stirred at room temperature for 2.5 hours. The mixture was concentrated and the residue was taken up into dichloromethane. The dichloromethane mixture was washed with 1N hydrochloric acid, water and aqueous sodium bicarbonate, dried (MgSO$_4$), filtered and concentrated. Product was purified from the residue by silica gel chromatography using 5% methanol in dichloromethane to provide 2-cyanomethylcarbamoylpiperidine-2-carboxylate (435 mg, 1.53 mmol) as an oil. Proton NMR (300 MHz, DMSO-$d_6$): $\delta$8.65 (bs, 1H), 7.34 (bs, 5H), $\delta$5.05 (bs, 2H), $\delta$4.64 (d, J=4 Hz, 1H), $\delta$4.11 (d, J=5.4 Hz, 2H), $\delta$3.87 (apparent d, J=12 Hz, 1H), $\delta$3.02 (m, 1H), $\delta$2.03 (m, 1H), 1.55 (apparent d, J=8 Hz, 3H), $\delta$1.06–1.20 (m, 2H); MS (electrospray): mH+301.9.

Proceeding as in Example 2 provided the following compounds of Formula I:

N-(1-cyanomethylcarbamoyl-3-methylbutyl)-3-(2-guanidinothiazol-4-yl)benzamide (Compound 4); Proton NMR (300 MHz, DMSO-$d_6$): $\delta$8.77 (bt, 1H), $\delta$8.71 (d, J=7 Hz, 1H), $\delta$8.36 (bs, 1H), $\delta$8.11 (d, J=7 Hz, 1H), $\delta$7.88 (m, 2H), $\delta$7.54 (t, J=7 Hz, 1H), $\delta$4.52 (m, 1H), $\delta$4.12 (d, J=6 Hz, 2H), $\delta$1.50–1.78 (m, 3H), $\delta$0.88 (dd, 6H); MS (electrospray): mH+ 414 (100%);

benzyl (S)-1-(N-cyanomethyl)-N-methylcarbamoyl-3-methylbutylcarbamate (Compound 5); Proton NMR (300 Mhz,CD$_3$OD): $\delta$7.70 (d, J=7 Hz, 1H), $\delta$7.41 (m, 5H), $\delta$5.02 (s, 2H), $\delta$4.43 (m, 3H), $\delta$3.14 (s, 3H), $\delta$1.24–1.68 (m, 3H), $\delta$0.88 (dd, 6H); MS (PCI): mH+ 318;

N-(1S-cyanomethylcarbamoyl-3-methylbutyl)piperidine-4-carboxamide Compound 6); Proton NMR (300 MHz, CD$_3$OD): $\delta$8.72 (bt, 1H), $\delta$8.57 (bs, 2H), $\delta$8.19 (d, J=7 Hz, 1H), $\delta$4.32 (m, 1H), $\delta$4.11 (d, J=6 Hz, 2H), $\delta$2.80–3.18 (m, 3H), $\delta$1.36–1.80 (m, 9H), $\delta$0.86 (dd, 6H); $^{13}$C NMR (67.9 MHz, CDCl$_3$): $\delta$173.8, 173.5, 118.1, 51.1, 42.9, 42.8, 39.2, 27.6, 25.9, 25.1, 24.8, 23.5, 21.8; MS (electrospray): mH+ 281 (100%);

benzyl 1S-cyanomethylcarbamoylpentylcarbamate (Compound 7); Proton NMR (300 MHz, DMSO-$d_6$): $\delta$8.65 (bt, 1H), $\delta$7.55 (d, J=7 Hz, 1H), $\delta$7.41 (bs, 5H), $\delta$5.00 (Abq, 2H), $\delta$4.08 (d, J=6 Hz, 2H), $\delta$3.97 (m, 1H), $\delta$1.52 (m, 2H), $\delta$1.24 (m, 4H), $\delta$0.81 (bs, 3H);

benzyl 1S-cyanomethylcarbamoyl-2-naphth-2-ylethylcarbamate (Compound 8); Proton NMR (300 MHz, DMSO-$d_6$): $\delta$8.81 (bt, 1H), $\delta$7.84 (m, 4H), $\delta$7.48 (m, 3H), $\delta$7.21 (m, 5H), $\delta$4.95 (Abq, 2H), $\delta$4.40 (m, 1H), $\delta$4.12 (d, J=7 Hz, 2H), $\delta$3.08 (m, 2H);

N-(1S-cyanomethylcarbamoylmethylbutylindole)-4-carboxamide (Compound 9); Proton NMR (300 MHz, DMSO-$d_6$): $\delta$11.34 (s, 1H), $\delta$8.67 (bt, 1H), $\delta$8.30 (d, J=7 Hz, 1H), $\delta$7.54 (t, J=6 Hz, 2H), $\delta$7.46 (s, 1H), $\delta$7.17 (t, J=6 Hz, 1H), $\delta$6.88 (s, 1H), $\delta$4.56 (m, 1H), $\delta$4.12 (d, J=5 Hz, 2H), $\delta$1.60 (m, 3H), $\delta$0.90 (apparent t, 6H);

N-(1S-cyanomethylcarbamoylmethylbutylindole)-6-carboxamide (Compound 10); Proton NMR (300 MHz, DMSO-$d_6$): $\delta$11.45 (s, 1H), $\delta$8.70 (bt, 1H), $\delta$8.48 (d, J=5 Hz, 1H), $\delta$8.01 (s, 1H), $\delta$7.57 (s, 2H), $\delta$7.49 (s, 1H), $\delta$6.48 (s, 1H), $\delta$4.53 (m, 1H), $\delta$4.12 (d, J=5 Hz, 2H), $\delta$1.47–1.80 (m, 3H), $\delta$0.89 (m, 6H);

N-(1-cyanomethylcarbamoyl-3-methylbutyl)-3-(methylpiperazin-1-ylmethyl)benzamide (Compound 11); and N-[3(1-cyanomethylcarbamoyl-3-methylbutylcarbamoyl)phenyl]-4-methylpiperazine-1-carboxamide (Compound 12).

Example 3

Benzyl 2S-cyanomethylcarbonyl-4-methylpyrrolidine-1-carboxylate (Compound 13)

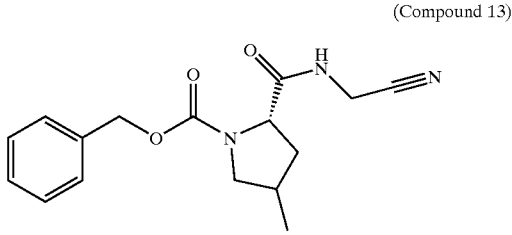

A solution comprised of I-benzyloxycarbonylpyrrolidine-2S-carboxylic acid (183 mg, 0.70 mmol) in THF (10 mL) was cooled to between 0 and 5° C. and then N-methylmorpholine (70 mg, 0.70 mmol) and isobutyl chloroformate (105 mg, 0.77 mmol) were added. The mixture was stirred at low temperature for 30 minutes and then aminoacetonitrile hydrochloride (71 mg, 0.77 mmol). and N-methylmorpholine (140 mg, 1.4 mmol) were added. The reaction was allowed to proceed for an additional 12 hours and then the reaction mixture was filtered. The filtrate was concentrated and the residue was partitioned between dichloromethane and 1N aqueous hydrochloric acid. The organic phase was separated, washed with saturated sodium bicarbonate and saturated sodium chloride, dried ($MgSO_4$), filtered and concentrated. Product was purified from the residue by silica chromatography using 5% methanol in dichloromethane to provide benzyl 2S-cyanomethylcarbonyl-4-methylpyrrolidine-1-carboxylate (42.0 mg, 0.14 mmol) as a colorless oil. Proton NMR (300 MHz, DMSO-d6): δ8.71 (m, 1H), δ7.42 (m, 5H), δ5.07 (m, 2H), δ4.12 (m, 3H), δ3.74 (m, 1H), δ2.93 (apparent q, 1H), δ2.08–2.50 (m, 3H), δ1.45 (m, 1H), δ0.95 (2d, 3H). $^{13}C$ NMR (67.9 MHz, $CD_3OD$): δ173.4, 173.0, 155.0, 154.1, 137.4, 137.3, 129.0, 128.9, 127.7, 118.0, 66.6, 60.9, 60.5, 54.6, 54.2, 39.5, 33.1, 32.4, 27.6, 27.5, 17.4, 17.3.

Proceeding as in Example 3 provided the following compounds of Formula I:

benzyl 2S-cyanomethylcarbamoyl-3-azabicyclo[3.1.0]hexane-3-carboxylate (Compound 14); Proton NMR (300 MHz, DMSO-d6): δ8.92 (m, 1H), δ7.40 (m, 5H), δ5.02 (m, 2H), δ4.18 (dd, J=5, 14 Hz, 2H), δ3.58 (m, 2H), δ1.60 (m, 2H), δ0.85 (m, 1H); and N-(1S-cyanomethylcarbamoylmethybutyl)benzamide (Compound 15); Proton NMR (300 MHz, DMSO-d6): δ8.74 (bt, 1H), δ8.53 (d, J=7 Hz, 1H), δ7.94 (d, J=6 Hz, 2H), δ7.49 (m, 3H), δ4.48 (m, 1H), δ4.11 (d, J=6 Hz, 2H), δ1.45–1.75 (m, 3H), δ0.88 (dd, 6H);

Example 4

4-Aminomethyl-N-(1-cyanomethylcarbamoyl-3-methylbutyl)benzamide (Compound 16)

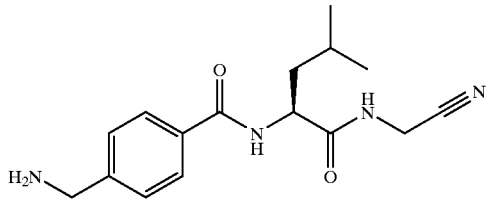

A suspension comprised of 4-[2-(4-aminobenzoylamino)-4-methylvaleryloxy]-SS, prepared as in Example 4, aminoacetonitrile hydrochloride (3 mg, 3.2 mmol) and 4-dimethylaminopyridine (20 mg, mmol) in dry pyrimidine (8 mL) was sealed in a polyethylene tube and shaken for 60 hours. The mixture was filtered and the resin was washed with pyridine and methanol. The combined filtrate was concentrated in vacuo and the residue was dissolved in 50:50 (v/v) water/acetonitrile. The solution was filtered and product was purified from the solution by RP-HPLC to provide 4aminomethyl-N-(1-cyanomethylcarbamoyl-3-methylbuty)benzamide (71 mg, 0.23 mmol) as a white solid.

$^1H$ NMR (270 MHz, DMSO-$d_6$): δ0.86 (d, 3, J=6.2 Hz), δ0.90 (d, 3, J=5.9 Hz), δ1.48–1.77 (m, 3), δ4.10–4.14 (m, 4), δ4.50 (m, 1), δ7.53 (d, 2, J=7.9 Hz), δ7.95 (d, 2, J=8.2 Hz), δ8.25 (2, br), δ8.61 (d, 1, J=7.9 Hz), δ8.77 (t, 1, J=5.4 Hz). ESI-MS m/z 303 (M+1).

Proceeding as in Example 4 provided the following compounds of Formula I:

N-(1S-cyanomethylcarbamoyl-3-methylbutyl)-2-dimethylaminoisonicotinamide (Compound 17); $^1H$ NMR (270 MHz, DMSO-$d_6$): δ0.86 (d, 3, J=5.2 Hz), δ0.90 (d, 3, J=4.7 Hz), δ1.52–1.74(m, 3), δ3.15 (s, 6), δ4.14 (d, 2, J=4.9 Hz), δ4.51 (m, 1), δ7.08 (d, 1, J=5.7 Hz), δ7.26 (s, 1), δ8.12 (d, 1 J=5.9 Hz), δ8.81 (t, 1, J=5.0 Hz), δ8.89 (d, 1, J=7.7 Hz); ESI-MS m/z 318 (M+1);

N-(1S-cyanomethylcarbamoyl-3-methylbutyl)-6-imidazol-1-ylnicotinamide (Compound 18); $^1H$ NMR (270 MHz, DMSO-$d_6$): δ0.88 (d, 3, J=4.9 Hz), δ0.92 (d, 3, J=5.1 Hz), δ1.55–1.74 (m, 3), δ4.14 (d, 2, J=5.4 Hz), δ4.54 (m, 1), δ7.61 (s, 1), δ8.07 (d, 1, J=8.7 Hz), δ8.33 (s, 1), δ8.54 (d, 1, J=8.3 Hz), δ8.81 (t, 1, J=5.3 Hz), δ8.92 (d, 1, J=7.3 Hz), δ9.02 (s, 1), δ9.42 (s, 1); ESI-MS m/z 341 (M+1);

N-(1S-cyanomethylcarbamoyl-3-methylbutyl)-6-dimethylaminonicotinamide (Compound 19); $^1H$ NMR (270 MHz, DMSO-$d_6$): δ0.85 (d, 3, J=5.2 Hz), δ0.89 (d, 3, J=5.2 Hz), δ1.52–1.67 (m, 3), δ3.15 (s, 6), δ4.12 (d, 2, J=4.9 Hz), δ4.48 (m, 1), δ6.91 (d, 1, J=8.9 Hz), δ8.12 (d, 1, J=9.3 Hz), δ8.48 (d, 1, J=7.1 Hz), δ8.55 (s, 1), δ8.72 (t, 1, J=5.0 Hz); ESI-MS m/z 318 (M+1);

N-(1S-cyanomethylcarbamoyl-3-methylbutyl)-6-(4-methylpiperazin-1-yl)nicotinamide (Compound 20); $^1H$ NMR (270 MHz, DMSO-$d_6$): δ0.84 (d, 3, J=5.9 Hz), δ0.89 (d, 3, J=5.9 Hz), δ1.50–1.73 (m, 3), δ2.84 (s, 3), δ3.02–3.23 (m, 4), δ3.51 (d, 2, J=10.8 Hz), δ4.12 (d, 2, J=5.5 Hz), δ4.46–4.56 (m, 3), δ7.00 (d, 1, J=9.1 Hz), δ8.10 (dd, 1, J=2.4, 8.9 Hz), δ8.42 (d, 1, J=7.9 Hz), δ8.70 (d, 1, J=2.2 Hz), δ8.73 (t, 1, J=5.8 Hz), δ9.88 (br. s, $NH^+$); ESI-MS m/z 373 (M+1);

N-(1S-cyanomethylcarbamoyl-3-methylbutyl)-2-pyrrolidin-1-ylisonicotinamide (Compound 21); $^1H$ NMR (270 MHz, DMSO-d$_6$): δ0.86 (d, 3, J=5.4 Hz), δ0.90 (d, 3, J=5.6 Hz), δ1.53–1.69 (m, 3), δ2.02 (br. s, 4), δ3.55 (br. s, 4), δ4.14 (d, 2, J=5.2 Hz), δ4.52 (m, 1), δ7.13 (d, 1, J=6.4 Hz), δ7.32 (s, 1), δ8.08 (d, 1, J=6.4 Hz), δ8.87 (t, 1, J=5.4 Hz), δ9.04 (d, 1, J=7.9 Hz); ESI-MS m/z 344 (M+1);

N-(1S-cyanomethylcarbamoyl-3-methylbutyl)-6-morpholin-4-ylnicotinamide (Compound 22); $^1$H NMR (270 MHz, DMSO-d$_6$): δ0.84 (d, 3, J=5.7 Hz), δ0.89 (d, 3, J=5.9 Hz), δ1.50–1.72 (m, 3), δ3.56(t, 4, J=4.5 Hz), δ3.68 (t, 4, J=4.5 Hz), δ4.11 (d, 2, J=5.2 Hz), δ4.47 (m, 1), δ6.89 (d, 1, J=9.1 Hz), δ8.06 (dd, 1, J=2.2, 8.9 Hz), δ8.38 (d, 1, J=8.1 Hz), δ8.65–8.69 (m, 2); ESI-MS m/z 360 (M+1);

N-[1S-cyanomethylcarbamoyl-3-methylbutyl]-3,4,5,6-tetrahydro-2H-[1,2']bipyridinyl-5'-carboxamide (Compound 23); $^1$H NMR (270 MHz, DMSO-d$_6$): δ0.84 (d, 3, J=3.3 Hz), δ0.89 (d, 3, J=5.9 Hz), δ1.49–1.72 (m, 9), δ3.65 (br. s, 4), δ4.11 (d, 2, J=5.4 Hz), δ4.48 (m, 1), δ7.03 (d, 1, J=8.9 Hz), δ8.09 (d, 1, J=9.7 Hz), δ8.44 (d, 2, J=7.6 Hz), δ8.56 (s, 1), δ8.70 (t, 1, J=5.4 Hz); ESI-MS m/z 358 (M+1);

N-1S-cyanomethylcarbamoyl-3-methylbutyl]-6-pyrrolidin-1-ylnicotinamide (Compound 24); $^1$H NMR (270 MHz, DMSO-d$_6$): δ0.85 (d, 3, J=5.7 Hz), δ0.89 (d, 3, J=5.9 Hz), δ1.50–1.71 (m, 3), δ2.00 (m, 4), δ3.50 (m, 4), δ4.12 (d, 2, J=5.4 Hz), δ4.48 (m, 1), δ6.84 (br. s, 1), δ8.16 (d, 1, J=10.1 Hz), δ8.51 (m, 2), δ8.75 (t, 1, J=5.9 Hz); ESI-MS m/z 344 (M+1);

N-[1S-cyanomethylcarbamoyl-3-methylbutyl]-3,4,5,6-tetrahydro-2H-[1,2']bipyrdinyl-4'-carboxamide (Compound 25); $^1$H NMR (270 MHz, DMSO-d$_6$): δ0.85 (d, 3, J=5.7 Hz), δ0.90(d,3, J=5.7 Hz), δ1.55–1.73 (m, 9), δ3.64(br. s, 4), δ4.13 (d, 2, J=5.4 Hz), δ4.51 (m, 1), δ7.08 (d, 1, J=5.9 Hz), δ7.45 (s, 1), δ8.11 (d, 1, J=5.9 Hz), δ8.83 (t, 1, J=6.2 Hz), δ8.92 (d, 1, J=7.9 Hz); ESI-MS m/z 358 (M+1);

N-[1S-cyanomethylcarbamoyl-3-methylbutyl-2-morpholin-4-yl]isonicotinamide (Compound 26); $^1$H NMR (270 MHz, DMSO-d$_6$): δ0.85 (d, 3, J=5.7 Hz), δ0.90 (d, 3, J=5.7 Hz), δ1.52–1.73 (m, 3), δ3.52 (t, 4, J=4.6 Hz), δ3.73 (t, 4, J=4.6 Hz), δ4.13 (d, 2, J=5.4 Hz), δ4.51 (m, 1), δ7.12 (d, 1, J=5.4 Hz), δ7.31 (s, 1), δ8.21 (d, 1, J=5.4 Hz), δ8.78 (m, 2); ESI-MS m/z 360 (M+1);

N-[1S-cyanomethylcarbamoyl-3-methylbutyl-2-imidazol-1-yl]isonicotinamide (Compound 27); $^1$H NMR (270 MHz, DMSO-d$_6$): δ0.88 (d, 3, J=5.9 Hz), δ0.92 (d, 3, J=5.9 Hz), δ1.55–1.72 (m, 3), δ4.16 (d, 2, J=5.7 Hz), δ4.56 (m, 1), δ7.71 (s, 1), δ7.96 (d, 1, J=5.2 Hz), δ8.33 (s, 1), 8.37 (s, 1), δ8.76 (d, 1, J=5.1 Hz), δ8.90 (t, 1, J=5.4 Hz), δ9.04 (d, 1, J=7.9 Hz), δ9.58 (s, 1); ESI-MS m/z 341 (M+1);

N-[1S-cyanomethylcarbamoyl-3-methylbutyl-2-(4-methylpiperazin-1-yl)]isonicotinamide (Compound 28); $^1$H NMR (270 MHz, DMSO-d$_6$): δ0.86 (d, 3, J=5.9 Hz), δ0.91 (d, 3, J=5.9 Hz), δ1.54–1.74 (m, 3), δ2.85 (s, 3), δ3.05–3.24 (m, 4), δ3.53 (d, 2, J=10.9 Hz), δ4.14 (d, 2, J=5.4 Hz), δ4.43–4.56 (m, 3), δ7.18 (d, 1, J=5.2 Hz), δ7.33 (s, 1), δ8.27 (d, 1, J=4.9 Hz), δ8.75 (d, 1, J=7.9 Hz), δ8.81 (t, 1, J=5.1 Hz), δ9.9 (br. s, NH$^+$); ESI-MS m/z 373 (M+1);

N-[1S-cyanomethylcarbamoyl-3-methylbutyl-3-dimethylaminomethyl]benzamide (Compound 29); $^1$H NMR (270 Mz, DMSO-d$_6$): δ0.86 (d, 3, J=6.2 Hz), δ0.91 (d, 3, J=6.2 Hz), δ1.52–1.71 (m, 3), δ2.74 (s, 6), δ4.13 (d, 2, J=5.7 Hz), δ4.33 (d, 2, J=4.7 Hz), δ4.53 (m, 1), δ7.58 (t, 1, J=7.6 Hz), δ7.65 (d, 1, J=7.7 Hz), δ8.00 (s, 1), 8.02 (d, 1, J=9.1 Hz), δ8.65 (d, 1, J=7.0 Hz), δ8.80 (t, 1,J=5.4 Hz), δ9.68 (br. s, NH$^+$).ESI-MS m/z 331 (M+1);

N-[1S-cyanomethylcarbamoyl-3-methylbutl-3-piperidin-1-ylmethyl]benzamide (Compound 30); $^1$H NMR (270 MHz, DMSO-d6): δ0.86 (d, 3, J=6.2 Hz), δ0.91 (d, 3, J=6.2 Hz), δ1.32–1.84 (m, 9), δ2.90 (m, 2), δ3.31 (m, 2), 4.13 (d, 2, J=5.7 Hz), δ4.34 (s, 2), δ4.53 (m, 1), δ7.58 (t, 1, J=7.7 Hz), δ7.65 (d, 1, J=6.9 Hz), δ8.01 (s, 1) 8.03 (d, 1, J=9.1 Hz), δ8.65 (d, 1, J=7.7 Hz), δ8.79 (t, 1, J=5.4 Hz), δ9.38 (br. s, NH$^+$); ESI-MS m/z 371 (M+1);

N-[1S-cyanomethylcarbamoyl-3-methylbutyl]-4-hydroxy-3-morpholin-4-ylmethylbenzamide (Compound 31); $^1$H NMR (270 MHz, DMSO-d$_6$): δ0.85 (d, 3, J=6.2 Hz), δ0.90 (d, 3, J=6.2 Hz), δ1.48–1.75 (m, 3), δ3.1 B 3.3 (m, 4), δ3.60 B 3.68 (m, 2), δ3.89 B 3.97 (m, 2), δ4.12 (d, 2, J=5.4 Hz), δ4.30 (s, 2), δ4.50 (m, 1), δ6.97 (d, 1, J=8.4 Hz), δ7.92 (d, 1, J=8.7 Hz), δ7.97 (s, 1), δ8.36 (d, 1, J=7.9 Hz), δ8.75 (t, 1, J=5.2 Hz), δ9.7 (br. s, NH$^+$), δ10.9 (br. s, OH); ESI–MS m/z 389 (M+1); and tert-butyl ester 4-[1S-cyanomethylcarbamoyl-3-methylbutylcarbamoylbenzyl]carbamate (Compound 32); $^1$H NMR (270 MHz, DMSO-d$_6$): δ0.85 (d, 3, J=6.0 Hz), δ0.89 (d, 3, J=6.2 Hz), δ1.39 (s, 9), δ1.50–1.75 (m, 3), δ4.11 (d, 2, J=5.6 Hz), δ4.15 (s, 2), 4.48 (m, 1), δ7.30 (d, 2, J=7.9 Hz), δ7.47 (t, NH, J=5.9 Hz), δ7.85 (d, 2, J=7.9 Hz), δ8.50 (d, 1, J=7.8 Hz), δ8.69 (t, 1, J=5.7 Hz); ESI-MS m/z 403 (M+1).

Example 5

N-(1S-Cyanomethylcarbamoyl-3-methylbutyl)-4-(2-methylthiazol-4-yl)benzamide (Compound 33)

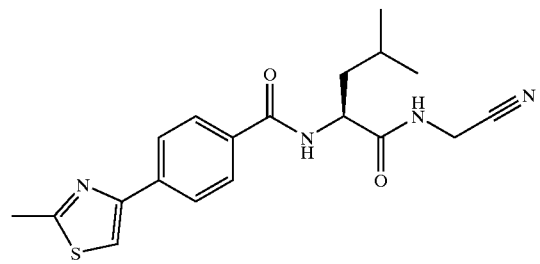

A mixture comprised of 2-amino-N-cyanomethyl-4methylpentanamide p-toluenesulfonic acid salt (0.75 g, 2.3 mmol), 4-(2-methylthiazol-4-yl)benzoic acid (0.5 g, 2.3 mmol), PyBOP® (1.2 g, 2.3 mmol) and triethylamine (1 ml, 5 mmol) in 10 mL of DMF was stirred for 1 hour. The mixture was concentrated under reduced pressure and the residue was partitioned between ethyl acetate (20 mL) and saturated sodium bicarbonate solution (20 mL). The organic layer was separated, washed with water and brine, dried (MgSO$_4$) and concentrated under reduced pressure. Product was purified from the residue by flash chromatography on a silica gel using 66% ethyl acetate in hexane to provide N-(1S-cyanomethylcarbamoyl-3-methylbutyl)-4-(2-methylthiazol-4-yl)benzamide (0.5 g, 1.4 mmol). $^1$H NMR (DMSO-d$_6$, ppm): δ0.81 (m, 6 H), δ1.55 (m, 3 H), δ2.81 (s, 3 H), δ4.01 (m, 2 H), 4.17 (m, 1 H), 8.01 (m, 5 H), δ8.41 (d, 1 H), δ9.01 (m, 1 H); ES-MS: 371.1 (M+H$^+$).

Proceeding as in Example 5 provided the following compounds of Formula I:

N-(1-cyanomethylcarbamoyl-3-methylbutyl-1H-benzoimidazole-5-carboxamide (Compound 34); $^1$H NMR (DMSO-d$_6$, ppm): δ0.86 (d, 6 H), δ1.42 (m, 3 H), δ4.21 (s, 2 H), δ4.81 (m, 1 H), δ7.6 (d, 1 H), δ8.01 (d, 1H), δ8.23 (s, 1 H), δ8.81 (s, 1 H), δ9.2 (s, 1 H); ES-Ms: 314.1 (M+H$^+$);

N-(1-cyanomethylcarbamoyl-3-methylbutyl)pyrazine-2-carboxamide (Compound 35); $^1$H NMR (DMSO-d$_6$, ppm):

δ0.91 (d, 6 H), δ1.41 (m, 3 H), δ4.21 (s, 2 H), δ4.61 (m, 1 H), δ8.81 (m, 4 H), δ9.2 (s, 1 H); ES-Ms: 276.1 (M+H$^+$);

N-(1-cyanomethylcarbamoyl-3-methylbutyl)-4-dimethylaminobenzamide (Compound 36); $^1$H NMR (DMSO-d$_6$, ppm): δ0.89 (d, 6 H), δ1.51 (m, 3 H), δ4.11 (s, 2 H), δ4.72 (m, 1 H), δ6.81 (d, 2 H), δ7.81 (d, 2 H), δ8.31 (s, 1 H), δ9.2 (s, 1 H); ES-Ms: 317.3 (M+H$^+$);

N-(1-cyanomethylcarbamoyl-3-methylbutyl)-3-dimethylaminobenzamide (Compound 37); $^1$H NMR (DMSO-d$_6$, ppm): δ0.86 (d, 6 H), δ1.45 (m, 3 H), δ4.22 (s, 2 H), δ4.85 (m, 1 H), δ7.11 (m, 1 H), δ7.41 (m, 3H), δ8.31 (s, 1 H), δ8.81 (s, 1 H); S-Ms: 317.3 (M+H$^+$);

N-(1-cyanomethylcarbamoyl-3-methylbutyl) benzodioxole-5-carboxamide (Compound 38); $^1$H NMR (DMSO-d$_6$, ppm): δ0.86 (d, 6 H), δ1.45 (m, 3 H), δ4.21 (s, 2 H), δ4.81 (m, 1 H), δ6.03 (s, 2 H), δ7.01 (d, 1 H), δ7.41 (m, 3 H), δ8.41 (s, 1 H), δ8.81 (s, 1 H); ES-Ms: 318.3 (M+H$^+$);

N-(1-cyanomethylcarbamoyl-3-methylbutyl)pyridine-4-carboxamide (Compound 39); $^1$H NMR (DMSO-d$_6$, ppm): δ0.86 (d, 6 H), δ1.42 (m, 3 H), δ4.01 (s, 2 H), δ4.81 (m, 1 H), δ6.03 (s, 2 H), δ8.01 (d, 2 H), δ8.41 (s, 1 H), δ8.81 (m, 3 H), δ9.03 (s, 1 H); ES-Ms: 275.3 (M+H$^+$);

N-(1-cyanomethylcarbamoyl-3-methylbutyl)-N'-benzothazol-6-ylureido (Compound 40); $^1$H NMR (DMSO-d$_6$, ppm): δ0.81 (d, 6 H), δ1.48 (m, 3 H), δ4.26 (s, 2 H), δ4.31 (m, 1 H), δ7.23 (d, 1 H), δ7.91 (dd, 2 H), δ8.13 (s, 1 H), δ8.81 (s, 2 H), δ9.11 (s, 1 H); ES–Ms: 346.1 (M+H$^+$);

N-(1-cyanomethylcarbamoyl-3-methylbutyl)-N'-pyrid-4-ylmethylureido (Compound 41); $^1$H NMR (DMSO-d$_6$, ppm): δ0.86 (d, 6 H), δ1.42 (m, 3 H), δ4.21 (s, 2 H), δ4.31 (m, 1 H), δ7.81 (d, 2 H), δ7.91 (dd, 2 H), δ8.81 (d, 2 H), δ8.91 (s, 2 H), δ9.11 (s, 1 H); MS (electrospray): mH$^+$ 304.1;

N-(1-cyanomethylcarbamoyl-3-methylbutyl)-4-methylpiperazine-1-carboxamide (Compound 42); $^1$H NMR (DMSO-d$_6$, ppm): δ0.86 (d, 6 H), δ1.42 (m, 3 H), δ3.01 (m, 4 H), δ3.72 (m, 4 H), δ4.21 (s, 2 H), δ4.31 (m, 1 H), δ7.81 (d, 1 H), 7.91 (d, 1 H), δ8.81 (d, 1 H); MS (electrospray): mH$^+$ 296.0;

N-(1-cyanomethylcarbamoyl-3-methybutyl)-N'-pyrid-3-ylureido (Compound 43); $^1$H NMR (DMSO-d$_6$, ppm): δ0.86 (d, 6 H), δ1.42 (m, 3 H), δ4.21 (s, 2 H), δ4.31 (m, 1 H), δ7.81 (m, 2 H), δ7.11 (m, 1 H), δ8.19 (m, 1 H), δ9.13 (m, 3 H); MS (electrospray): mH$^+$ 290.0;

N-(1-cyanomethylcarbamoyl-3-methybutyl)-N'-methyl-N'-(1-benzylpyrrolidin-3-yl)ureido (Compound 44); Proton NMR (300 MH, DMSO-d$_6$): δ8.77 (bt, 1H), δ8.44 (m, 3H), δ7.63 (bd, 1H), δ7.30 (m, 1H), δ4.25 (m, 1H), δ4.11 (m, 2H), δ3.50 (ABq, 2H), δ1.40–1.60 (m, 3H); δ0.81 (m, 6H); MS (electrospray): mH$^+$ 289 (100%); and 4-benzyl-N-(1-cyanomethylcarbamoyl-3-methylbutyl) piperazine-1-carboxyamide (Compound 45); $^1$H NMR (DMSO-d$_6$, ppm): δ0.86 (d, 6 H), δ1.42 (m, 3 H), δ2.01 (m, 2 H), δ2.21 (m, 1 H), δ3.01 (m, 2 H), δ2.81 (s, 3 H), δ3.01 (m, 1 H), δ3.21 (m, 2 H), δ3.72 (m, 6 H), δ4.21 (s, 2 H), δ4.31 (m, 1 H), δ7.27 (m, 5 H), δ8.81 (m, 1 H); MS (electrospray): mH$^+$ 386.2.

Example 6

Benzyl 1S-(1-cyano-1-methylethylcarbamoyl)-3-methylbutylcarbamate

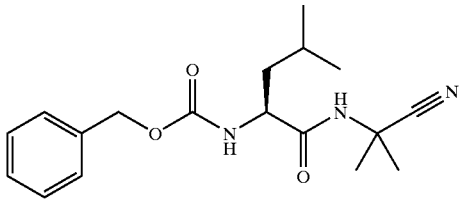

(Compound 46)

A solution comprised of methyl 2-(1S-benzyloxycarbonylamino-3-methylvalerylamino)-2-methylpropionate (0.911 g, 2.5 mmol) in anhydrous methanol (10 mL) was cooled to between 0 and 5° C. and then ammonia gas was introduced until the volume of the solution had increased by approximately 3 mL. The reaction vessel was sealed and the solution was allowed to sit at ambient temperature for 168 hours. The solution than was concentrated and product was purified from the residue by silica chromatography using 5% methanol in dichloromethane to provide benzyl 1S-carbamoylmethylcarbamoyl-3-methylbutylcarbamate (514 mg, 1.48 mmol) as a white solid, m.p. 93–94° C. Proton NMR (300 MHz, DMSO-d$_6$): δ7.99 (s, 1H), δ7.51 (d, J=7 Hz, 1H), δ7.32 (bs, 5H), δ6.92 (bs, 2H), δ4.99 (s, 2H), δ3.97 (m, 1H), δ1.58 (m, 1H), δ1.39 (m, 2H), δ1.33 (s, 3H), δ1.31 (s, 3H), δ0.83 (apparent t, J=7 Hz, 6H).

A mixture comprised of benzyl 1S-carbamoylmethylcarbamoyl-3-methylbutylcarbamate (0.175 g, 0.5 mmol) and triethylamine (141 µL, 1.5 mmol) in anhydrous tetrahydrofuran (15 mL) was cooled to between 0 and 5° C. and trifluoroacetic anhydride (210 µL, 1 mmol) was added. The mixture was kept at between 0 and 5° C. for 1 hour and then isopropanol (3 drops) was added. The mixture was concentrated and product was purified from the residue by silica chromatography using 2% methanol in dichloromethane to provide benzyl 1S-(1-cyano-1-methylethylcarbamoyl)-3-methylbutylcarbamate (106 mg, 0.32 mmol) as a white foam. Proton NMR (300 MHz, DMSO-d$_6$): δ8.48 (s, 1H), δ7.43 (d, J=7 Hz, 1H), 7.32 (bs, 5H), δ4.99 (s, 2H), δ4.02 (m, 1H), δ1.53 (s, 3H), δ1.51 (s, 3H), δ1.20–1.60 (m, 3H), δ0.83 (t, J=6 Hz, 6H). MS (electrospray): mH$^+$ 332 (100%).

Proceeding as in Example 6 provided the following compounds of Formula I:

benzyl 1S-(1S-cyano-3-phenylpropylcarbamoyl)-3-methylbutylcarbamate (Compound 47); Proton NMR (300 MHz, CDCl3): δ7.05–7.30 (m, 10H), δ5.29 (m, 1H), δ5.08 (m, 2H), δ4.76 (apparent q, J=7.5 Hz, 1H), δ4.17 (m, 1H), δ2.74 (m, 3H), δ2.03 (m, 2H), δ1.42–1.68 (m, 3H), δ0.90 (bs, 6H). 13C NMR (67.9 MHz, CDCl3): δ171.8, 156.6, 139.2, 135.9, 128.9, 128.5, 126.8, 118.3, 67.6, 53.3, 41.0, 40.2, 34.5, 31.6, 24.7, 22.9, 22.0; MS (electrospray): mH$^+$ 408 (100%);

3-aminomethyl-N-(1S-cyanomethylcarbamoyl-3-methybutyl)benzamide (Compound 48); $^{13}$C NMR (67.9 MHz, D2O): δ175.5, 170.6, 134.0, 133.4, 132.8, 129.7, 128.1, 128.0, 116.9, 53.3, 42.8, 39.7, 27.7, 24.6, 22.2, 20.8; MS (electrospray): mH$^+$ 303 (100%);

benzyl 2S-cyanomethylcarbamoylpyrrolidine-1-carboxylate (Compound 49); m.p. 136–137° C.; Proton NMR (300 MHz, DMSO-d₆): δ8.77 (m, 1H), δ7.30 (m, 5H), δ5.00 (m, 2H), δ4.19, m (1H), δ4.10 (t, J=6 Hz, 2H), δ3.39 (m, 2H), δ2.08 (m, 1H), δ1.79 (m, 3H); MS (electrospray): mH⁺ 288 (100%);

benzyl 2R-cyanomethylcarbamoylpyrrolidine-1-carboxylate (Compound 50); m.p. 135–136° C.; Proton NMR (300 MHz, DMSO-d₆): δ8.77 (m, 1H), δ7.30 (m, 5H), δ5.00 (m, 2H), δ4.19, m (1H), δ4.10 (t, J=6 Hz, 2H), δ3.39 (m, 2H), δ2.08 (m, 1H), δ1.79 (m, 3H); MS (electrospray): mH⁺ 288 (100%);

N-(1S-cyanomethylcarbonyl-3-methylbutyl)pyridine-3-carboxamide ((Compound 51); m.p. 173–174° C.; Proton NMR (300 MHz, DMSO-d₆): δ9.04 (d, J=2 Hz, 1H), δ8.70 (m, 3H), δ8.20 (m, 1H), δ7.49 (m, 1H), δ4.49 (m, 1H), δ4.11 (d, J=6 Hz, 2H), δ1.45–1.78 (m, 3H), δ0.87 (dd, 6H); MS (electrospray): mH⁺ 275 (100%);

benzyl 1S-(1-cyanocyclopropylcarbamoyl)-3-methylbutylcarbamate (Compound 52); Proton NMR (300 MHz, CD3OD): δ7.33 (m, 6H), δ5.07 (s, 2H), δ4.06 (m, 1H), δ1.65 (m, 1H), δ1.47 (m, 4H), δ1.86 (m, 2H), δ0.93 (t, J=6 Hz, 6H); MS (electrospray): mH⁺330 (100%);

N-(1S-cyanomethylcarbamoylmethylbutylindole)-5-carboxamide (Compound 53); m.p. 225–226° C.; Proton NMR (300 MHz, DMSO-d₆): δ11.31 (s, 1H), δ8.63 (t, J=6 Hz, 1H), δ8.35 (d, J=7 Hz, 1H), δ8.20 (s, 1H), δ7.66 (d, J=8 Hz, 1H), δ7.41 (m, 2H), δ6.52 (s, 1H), δ4.50 (m, 1H), δ4.10 (d, J=6 Hz, 2H), δ1.48–1.79 (m, 3H), δ0.86 (m, 6H); MS (electrospray): mH⁺ 313 (100%);

N-(1S-cyanomethylcarbamoylmethylbutyl-2,3-dihydroindole)-5-carboxamide (Compound 54); Proton NMR (300 MHz, DMSO-d₆): δ8.59 (7, J=6 Hz, 1H), δ8.11 (d, J=7 Hz, 1H), δ7.65 (s, 1H), δ7.58 (d, J=7 Hz, 1H), δ6.57 (d, J=7 Hz, 1H), δ4.44 (m, 1H), δ4.08 (d, J=6 Hz, 2H), δ3.51 (t, J=8 Hz, 2H), δ2.97 (t, J=8 Hz, 2H), δ1.58 (m, 3H), δ0.87 (m, 6H); MS (electrospray): mH⁺ 315 (100%);

benzyl 1R-cyanomethylcarbamoyl-3-methylbutylcarbamate (Compound 55); m.p. 120–121° C.; Proton NMR (300 Mz, DMSO-d₆): δ8.68 (t, J=6 Hz, 1H), δ7.54 (d, J=7 Hz, 1H), δ7.33 (bs, 5H), δ4.99 (ABq, 2H), δ4.09 (d, J=5 Hz, 2H), δ4.00 (m, 1H), δ1.28–1.65 (m, 3H), δ0.83 (apparent t, J =7 Hz, 6H); MS (electrospray): mH⁺ 304 (100%);

benzyl 1S-(1S-cyanoethylcarbamoyl)-3-methylbutylcarbamate (Compound 56); Proton NMR (300 MHz, DMSO-d₆): δ8.76 (d, J=7 Hz, 1H), δ7.51 (d, J=5 Hz, 1H), δ7.34 (bs, 5H), δ5.01 (ABq, 2H), δ4.74 (m, 1H), δ4.01 (m, 1H), δ1.23–1.65 (m, 6H), δ0.86 (apparent t, J=6 Hz, 6H); ¹³C NMR (67.9 MHz, DMSO-d₆): 173.0, 137.5, 128.9, 128.4, 128.2, 120.8, 66.0, 53.1, 39.7, 24.7, 23.5, 21.9, 18.6; MS (electrospray): mH⁺ 318 (100%);

benzyl 1S-(2S-cyanopyrrolidin-1-ylcarbonyl)-3-methylbutylcarbamate (Compound 57); Proton NMR (300 MHz, CD₃OD): δ7.32 (bs, 5H), δ5.06 (s, 2H), δ4.75 (m, 1H), δ4.40 (m, 1H), δ3.70 (m, 2H), δ2.05–2.17 (m, 4H), δ1.39–1.83 (m, 3H), δ0.96 (m, 6H); ¹³C NMR (67.9 MHz, CD₃OD): δ172.7, 157.5, 137.0, 128.2, 127.7, 127.5, 118.2, 66.4, 51.3, 47.4, 46.4, 39.8, 29.5, 25.0, 24.6, 22.3, 20.5; MS (electrospray): mH⁺ 344 (100%);

tert-butyl 3-(1S-cyanomethylcarbamoyl-3-methylbutylcarbamoyl)benzylcarbamate (Compound 58); Proton NMR (300 MHz, DMSO-d₆): δ8.71 (bt, 1H), δ8.54 (d, J=8.54 (d, J=8 Hz, 1H), δ7.77 (bs, 2H), δ7.39 (m, 3H), δ4.52 (m, 1H), δ4.16 (d, J=6 Hz, 2H), δ4.11 (d, J=6 Hz, 2H), δ1.43–1.78 (m, 2H), δ1.38 (bs, 10H), δ0.87 (dd, 6H);

2S-(1S-benzyloxycarbonylamino-3-methylbutylcarbonylamino)-2-cyanoethyl acetate (Compound 59); Proton NMR (300 MH, DMSO-d₆): δ8.89 (d, J=7 Hz, 1H), δ7.52 (d, J=8 Hz, 1M), δ7.32 (bs, 5H), δ5.00 (m, 3H), δ4.20 (d, J=6 Hz, 2H), δ4.03 (m, 1H), δ2.03 (s, 3H), δ1.28–1.66 (m, 3H), δ0.84 (apparent t, 6H). MS (electrospray): mH⁺ 376 (100%);

2-(2-acetylaminoacetylamino)-N-cyanomethyl-4-methylpentanamide (Compound 61); Proton NMR (300 Mz, DMSO-d₆): δ8.66 (bt, 1H), δ8.08 (m, 2H), δ4.27 (m, 1H), δ4.10 (d, J=6 Hz, 2H), δ3.70 (d, J=6 Hz, 2H), δ1.83 (s, 3H), δ1.38–1.64 (m, 3H), δ0.85 (dd, 6H); MS (electrospray): mH⁺ 269 (100%);.

benzyl 1S-(1S-cyano-3-methylbutylcarbamoyl)-3-methylbutylcarbamate (Compound 62); Proton NMR (300 MHz, DMSO-d₆): δ8.71 (d, J=7 Hz, 1H), δ7.51 (d, J=8 Hz, 1H), δ7.32 (s, 5H), δ4.99 (s, 2H), δ4.68 (m, 1H), δ3.98 (m, 1H), δ1.30–1.74 (m, 6H), δ0.83 (m, 12H); MS (electrospray): mH⁺ 360;

N-(1S-cyanomethylcarbamoyl-3-methylbutyl)-2,3,4-trihydro-1H-quinolinecarboxamide (Compound 63); Proton NMR (300 MHz, DMSO-d₆): δ8.58 (bt, 1H), δ7.96 (d, J=7 Hz, 1H), δ7.45 (m, 2H), δ6.38 (d, J=7 Hz, 1H), δ4.44 (m, 1H), δ4.07 (d, J=6 Hz, 2H), δ3.60 (t, J=7 Hz, 2H), δ2.95–3.16 (m, 4H), δ1.41–1.80 (m, 3H), δ0.84 (m, 6H); MS (electrospray): mH⁺ 329;

N-(1S-cyanomethylcarbamoyl-3-methylbutyl)-4-aminosulfonylbenzamide (Compound 64); m.p. 191–194 ° C.; Proton NMR (300 MHz, DMSO-d₆): δ8.77 (m, 2H), δ8.04 (d, J=6 Hz, 2H), δ7.88 (d, J=6 Hz, 2H), δ7.50 (s, 2H), δ4.49 (m, 1H), δ4.12 (m, 2H), δ1.50–1.74 (m, 3H), δ0.86 (m, 6H); MS (electrospray): mH⁺ 353 (100%);

N-(1S-cyanomethylcarbamoyl-3-methylbutyl)-4-phenylbutyramide (Compound 65); Proton NMR (300 MHz, DMSO-d₆): δ8.64 (bt, 1H), δ8.04 (d, J=8 Hz, 1H), δ7.10–7.28 (m, 5H), δ4.26 (m, 1H), δ4.08 (m, 2H), δ2.52 (t, J=7 Hz, 2H), δ2.12 (t, J=7 Hz, 2H), δ1.78 (m, 2H), δ1.32–1.60 (m, 3H), δ0.83 (m, 6H); MS (electrospray): mH⁺ 316 (100%);

N-(1S-cyanomethylcarbamoyl-3-methylbutyl)-3-methylthiophene-2-carboxamide (Compound 66); m.p. 132–134° C.; Proton NMR (300 MHz, DMSO-d₆): δ8.72 (bt, 1H), δ8.04 (d, J=8 Hz, 1H), δ7.55 (d, J=5 Hz, 1H), δ6.95 (d, J=5 Hz, 1H), δ4.41 (m, 1H), δ4.12 (m, 2H), δ2.39 (s, 3H), δ1.42–1.75 (m, 3H), δ0.86 (m, 6H). MS (electrospray): mH⁺ 294 (100%);

N-[1-cyanomethylcarbamoyl-3-methylbutyl-4-(2-guanidinothiazol-4-yl)]benzamide (Compound 67); ¹H NMR (DMSO-d₆, ppm): δ0.96 (m, 6 H), δ1.65 (m, 3 H), δ4.01 (m, 2 H), 4.17 (m, 1H), δ8.03 (m, 5H), δ8.31 (m, 2H), δ8.73 (d, 1H), δ8.91 (d, 1 H); MS (electrospray): mH⁺ 414.1;

N-[1S-cyanomethylcarbamoyl-3-methylbutyl-3-pyrid-3-ylacrylamide (Compound 68); ¹H NMR (DMSO-d₆, ppm): δ0.96 (m, 6 H), δ1.55 (m, 3 H), δ4.01 (m, 2 H), δ4.17 (m, 1 H), δ6.85 (d, 1 H), δ7.54 (d, 1 H), δ7.66 (d, 1 H), δ8.22 (d, 1 H), δ8.81 (d, 1 H), δ8.84 (m, 1 H); MS (electrospray): mH⁺ 301.0;

N-[1S-cyanomethylcarbamoyl-3-methylbutyl-3-(1H-imidazol-4-yl)acrylamide (Compound 69); ¹H NMR (DMSO-d₆, ppm): δ0.96 (m, 6 H), δ1.55 (m, 3H), δ4.01 (m, 2 H), δ4.17 (m, 1 H), δ6.71 (d, 2 H), δ7.33 (d, 1 H), δ7.95 (s, 1 H), δ8.81 (d, 1 H), δ9.01 (m, 1 H); MS (electrospray): mH⁺ 290.1;

N-(1S-cyanomethylcarbamoyl-3-methylbutyl)-4-N',N'-dimethylaminobenzamide N'-oxide (Compound 70); Proton NMR (300 MHz, CD₃OD): δ8.10 (m, 4H), δ4.65 (m, 4H), δ4.65 (m, 1H), δ4.17 (s, 2H), δ3.97 (s, 6H), δ1.58–1.90 (m, 3H), δ0.98 (m, 6H); MS (electrospray): mH⁺ 333 (100%);

N-(1S-cyanomethylcarbamoyl-3-methylbutyl)-4-(1H-imidazol-2-yl)benzamide (Compound 71); m.p. 246–247° C.; Proton NMR (300 MHz, DMSO-d₆): δ12.66 (s, 1H), δ8.70 (bb, 1H), δ8.57 (d, J=7 Hz, 1H), δ7.98 (bs, 4H), δ4.49 (m, 1H), δ4.10 (m, 2H), δ1.50–1.75 (m, 3H), δ0.87 (m, 6H); MS (electrospray): mH⁺ 340 (100%);

N-(1S-cyanomethylcarbamoyl-4-methylpentyl)-4-diethylaminobenzamide (Compound 72); ¹H NMR (DMSO-d₆, ppm): δ0.96 (mt, 6 H), δ1.11 (m, 6 H), δ1.85 (m, 3 H), δ3.3 (m, 4 H), δ4.01 (m, 2 H), δ4.17 (m, 1 H), δ6.71 (m, 2 H), δ7.53 (m, 2 H), δ8.05 (s, 1 H), δ8.81 (d, 1 H); MS (electrospray): mH⁺ 359.0;

N-(1S-cyanomethylcarbamoyl-3-methylbutyl)-4-morpholin-4-ylbenzamide (Compound 73); ¹H NMR (DMSO-d₆, ppm): δ0.96 (m, 6 H), δ1.65 (m, 3 H), δ3.31 (m, 4H), δ3.72 (m, 4 H), δ4.01 (m, 2 H), 4.17 (m, 1 H), δ7.01 (d, 2H), δ7.63 (d, 2 H), δ8.81 (d, 1 H), δ9.01 (m, 1 H); MS (electrospray): mH⁺ 359.1;

N-(1S-cyanomethylcarbamoyl-3-methylbutyl)-4(4-methylpiperazin-1-yl)benzamide (Compound 74); ¹H NMR (DMSO-d₆, ppm): δ0.96 (m, 6 H), δ1.65 (m, 3 H), δ2.81 (s, 3 H), δ3.31 (m, 4 H), δ3.81 (m, 4 H), δ4.01 (m,2 H), δ4.17 (m, 1 H), δ7.01 (d, 2H), δ7.73 (d, 2 H), δ8.41 (d, 1 H), δ9.01 (m, 1 H); MS (electrospray): mH⁺ 372.1;

N-(1S-cyanomethylcarbamoyl-3-methylbutyl)-3-(1H-imidazol-2-yl)benzamide (Compound 75); Proton NMR (300 MHz, DMSO-d₆): δ8.83 (bt, 1H), δ8.76 (d, J=8 Hz, 1H), δ8.50 (s, 1H), δ8.13 (m, 2H), δ7.78 (m, 3H), δ4.52 (m, 1H), δ4.13 (d, J=6 Hz, 2H), δ1.50–1.74 (m, 3H), δ0.88 (m, 6H); MS (electrospray): mH⁺ 340 (100%);

N-(1S-cyanomethylcarbamoyl-3-methylbutyl)-4-pyrrol-1-ylbenzamide (Compound 76); ¹H NMR (DMSO-d₆, ppm): δ0.96 (m, 6H), δ1.65 (m, 3 H), δ2.81 (s, 3 H), δ3.31 (m, 4 H), δ3.81 (m, 4 H), δ4.01 (m, 2 H), δ4.17 (m, 1 H), δ6.03 (s, 2 H), δ7.31 (d, 2 H), δ7.73 (d, 2 H), δ8.01 (d, 2 H), δ8.81 (d, 1 H), δ9.01 (m, 1 H); MS (electrospray): mH⁺ 338.1;

benzyl 1-cyanomethylcarbamoyl-4-guanidinobutyl)carbamate (Compound 77); ¹H NMR (DMSO-d₆, ppm): δ1.65 (m, 4 H), δ2.91 (m, 2 H), δ4.01 (m, 2 H), δ4.17 (m, 1 H), δ5.03 (s, 2 H), δ7.31 (s, 5 H), δ7.73 (d, 1 H), δ8.01 (d, 2 H), δ8.81 (d, 1 H), δ9.01 (m, 1 H); MS (electrospray): mH⁺ 347.1;

N-cyanomethyl-2-(1H-indol-3-ylacetylamino)-4-methylpentanamide (Compound 78); Proton NMR (300 MHz, DMSO-d₆): δ10.74 (bs, 1H), δ8.63 (bt, 1H), δ8.11 (d, J=8 Hz, 1H), δ7.41 (d, J=8 Hz, 1H), δ7.21 (d, J=8 Hz, 1H), 7.06(s, 1H) δ6.94 (t, J=7 Hz, 1H), δ6.84 (t, J=7 Hz, 1H), δ4.18 (m, 1H), δ4.00 (m, 2H), δ3.44 (ABq, 2H), δ1.25–1.53 (m, 3H), δ0.67 (m, 6H). MS (electrospray): mH⁺ 327 (100%);

N-cyanomethyl-4-methyl-2-(3-pyrid-2-ylmethylureido)pentanamide (Compound 79); ¹H NMR (DMSO-d₆, ppm): δ0.86 (d, 6 H), δ1.42 (m, 3 H), δ4.21 (s, 2 H), δ4.31 (m, 1 H), δ6.81 (m, 2 H), δ7.81 (m, 2 H), δ8.21 (m, 1 H), δ8.81 (m, 2 H); MS (electrospray): mH⁺ 304.0;

N-(1-cyanomethylcarbamoyl-3-methylbuty)-[1,4']bipiperidinyl-1'-carboxamide (Compound 80); ¹H NMR (DMSO-d₆, ppm): δ0.86 (d, 6 H), δ1.42 (m, 3 H), δ3.01 (m, 2 H), δ3.72 (m, 6 H), δ4.21 (s, 2 H), δ4.31 (m, 1 H), δ7.27 (s, 5 H), δ8.81 (m, 1 H); MS (electrospray): mH⁺ 364.2;

N-(1-cyanomethylcarbamoyl-3-methylbutyl)-4-diethylaminobenzamide (Compound 81); ¹H NMR (DMSO-d₆, ppm): δ0.86 (d, 6 H), δ1.61 (m, 6 H), δ6 H), δ1.42 (m, 3 H), δ3.78 (m, 4 H), δ4.21 (s, 2 H), δ4.81 (m, 1 H), δ6.81 (d, 2 H), δ7.81 (d, 2H), δ8.31 (s, 1 H), δ9.2 (s, 1 H); MS (electrospray): mH⁺ 345.3;

N-(1-cyanoethylcarbamoyl-3-methylbutyl)-4-fluorobenzamide (Compound 82); ¹H NMR (DMSO-d₆, ppm): δ0.86 (d, 6 H), δ1.62 (m, 6 H), δ4.21 (s, 2 H), δ4.81 (m, 1 H), δ6.81 (d, 2 H), δ7.81 (d, 2 H), δ8.31 (s, 1 H), δ9.2 (s, 1 H); MS (electrospray): mH⁺ 292.0;

N-(1-cyanomethylcarbamoyl-3-methylbutyl)-4-hydroxybenzamide (Compound 83); ¹H NMR DMSO-d₆, ppm): δ0.86 (d, 6 H), δ1.62 (m, 3 H), δ4.21 (s, 2 H), δ4.81 (m, 1 H), δ6.81 (d, 2 H), δ7.81 (d, 2 H), δ8.31 (s, 1 H), δ9.2 (s, 1 H); MS (electrospray): mH⁺ 292.0;

N-(1-cyanomethylcarbamoyl-3-methylbutyl)-3-hydroxybenzamide (Compound 84); ¹H NMR (DMSO-d₆, ppm): δ0.86 (d, 6 H), δ1.62 (m, 6 H), δ4.21 (s, 2 H), δ4.81 (m, 1 H), δ6.81 (m, 1 H), δ7.21 (m, 4 H), δ8.31 (s, 1 H), δ9.2 (s, 1 H); MS (electrospray): mH⁺ 290.0;

N-(1-cyanomethylcarbamoyl-3-methylbutyl)-4-guanidinobenzamide (Compound 85); ¹H NMR (DMSO-d₆, ppm): δ0.86 (d, 6 H), δ1.62 (m, 6 H), δ3.30 (m, 2 H), δ4.21 (s, 2 H), δ4.81 (m, 1H), δ7.3 (d, 2 H), δ7.62 (m, 1 H), δ7.91 (d,2 H), δ8.31 (s, 1 H), δ9.2 (s, 1 H); MS (electrospray): mH⁺ 331.0;

N-(1-cyanomethylcarbamoyl-3-methylbutyl)-2-pyrid-4-ylthiazole-5-carboxamide (Compound 86); ¹H NMR (DMSO-d₆, ppm): δ0.86 (d, 6 H), δ1.1 (m, 6 H), δ4.21 (s, 2 H), δ4.81 (m, 1H), δ7.81 (m, 1 H), δ8.31 (m, 2 H), δ8.81 (m, 2 H), δ9.2 (s, 1 H); MS (electrospray): mH⁺ 358.0;

N-(1-cyanomethylcarbamoyl-3-methylbutyl)-2-pyrid-3-ythiazole-5-carboxamide (Compound 87); ¹H NMR (DMSO-d₆, ppm): δ0.86 (d, 6 H), δ1.1 (m, 6 H), δ4.21 (s, 2 H), δ4.81 (m, 1 H), δ8.21 (m, 2 H), δ8.51 (m, 1 ), δ8.81 (m, 2 H), 2 H), δ9.2 (s, 1 H); MS (electrospray): mH⁺ 358.0;

6-amino-N-(1-cyanomethylcarbamoyl-3-methylbutyl)nicotinamide (Compound 88); ¹H NMR (DMSO-d₆, ppm): δ0.86 (d, 6 H), δ1.62 (m, 6 H), δ4.21 (s, 2 H), δ4.81 (m, 1 H), δ6.81 (m, 1 H), δ7.21 (m, 4 H), δ8.31 (s, 1 H), δ9.2 (s, 1 H); MS (electrospray): mH⁺ 290.0;

benzyl 1-cyanomethylcarbamoyl-4,4,4-trifluoro-3-methylbutylcarbamate (Compound 89); ¹H NMR (DMSO-d₆, ppm): δ1.01 (m, 3 H), δ3.02 (m, 3 H), δ4.21 (s, 2 H), δ5.01 (s, 2 H), δ5.12 (m, 1 H), δ7.21 (m, 5 H), δ8.01 (s, 1 H), δ9.21 (s, 1 H); MS (electrospray): mH⁺ 358.2;

benzyl 1-cyanomethylcarbamoyl-1,3-dimethylbutylcarbamate (Compound 90); ¹H NMR (DMSO-d₆, ppm): δ0.86 (m, 6H), δ1.81 (m, 2 H), δ4.01 (m, 3 H), δ5.01 (s, 2 H), δ7.21 (m, 5 H), δ8.01 (s, 1 H), δ9.21 (s, 1 H); MS (electrospray): mH+ 318.2;

benzyl 1-cyanomethylcarbamoyl-2,2-dimethylpropylcarbamate (Compound 91); ¹H NMR (DMSO-d₆, ppm): δ0.96 (s, 9 H), δ3.88 (m, 1 H), δ4.01 (s, 2 H), δ5.01 (s, 2 H), δ7.21 (m, 5 H), δ8.01 (s, 1 H), δ9.21 (s, 1 H); MS (electrospray): mH⁺ 304.2;

benzyl 1-cyanomethylcarbamoyl-3,3-dimethylbutylcarbamate (Compound 92); ¹H NMR (DMSO-d₆, ppm): δ0.96 (s, 9 H), δ1.55 (m, 2 H), δ4.01 (m, 3 H), δ5.01 (m, 2 H), δ7.27 (m, 5 H), δ8.01 (s, 1 H), δ9.21 (s, 1 H); MS (electrospray): mH⁺ 318.2;

benzyl (cyanomethylcarbamoyl)(phenyl)methylcarbamate (Compound 93); ¹H NMR (DMSO-d₆, ppm): δ0.96 (s, 9 H), δ1.55 (m, 2 H), δ4.01 (m, 3 H), δ5.01 (m, 2 H), δ7.27 (m, 5 H), δ8.01 (s, 1 H), δ9.21 (s, 1 H); MS (electrospray): mH⁺ 324.2;

N-(1S-cyanomethylcarbamoyl-3-methylbutyl)-4-dimethylaminonaphthalene-1-carboxamide (Compound 94); m.p. 161–162° C.; Proton NMR (300 MHz, DMSO-d$_6$): δ8.88 (bt, 1H), δ8.74 (d, J=8 Hz, 1H), δ8.24–8.37 (m, 2H), δ7.60–7.71 (m, 3H), δ7.20 (d, J=8 Hz, 1H), δ4.64 (m, 1H), δ4.29 (m, 2H), δ2.94 (s, 6H), δ1.57–1.83 (m, 3H), δ1.02 (apparent t, 6H); MS (electrospray): mH$^+$ 367 (100%); and N-(1S-cyanomethylcarbamoyl-3-methylbutyl)-4-dimethylamino-2-hydroxybenzamide (Compound 95); m.p. 171–173° C.; Proton NMR (300 MHz, DMSO-d$_6$): δ12.57 (bs, 1H), δ8.73 (bt, 1H), δ8.40 (d, J=7 Hz, 1H), δ7.76 (d, J=8 Hz, 1H), δ6.24 (dd, J=2, 8 Hz, 1H), δ6.01 (d, J=2 Hz, 1H), δ4.47 (m, 1H), δ4.10 (m, 2H), δ2.92 (s, 6H), δ1.47–1.72 (m, 3H), δ0.87 (m, 6H); MS (electrospray): mH$^+$ 333 (100%).

Proceeding in a fashion analogous to the procedures exemplified above provided the following compounds of Formula I:

benzyl 1-[1-(1-cyanomethylcarbamoyl-2-phenylethylcarbamoyl-3-methylbutylcarbamoyl]-2-methylpropylcarbamate (Compound 96);

N-benzyl-N-(1S-cyanomethylcarbamoyl)-3-methylbutylureido (Compound 97); Proton NMR (270 MHz, DMSO-d$_6$): δ_8.78 (t, 1H), 7.2–7.40 (m, 5H), 6.46 (t, 1H), 6.23 (d, 1H), 4.11–4.29 (m, 5H), 1.35–1.67 (m, 3H), 0.88 (apparent t, 6H). LCMS (electrospray) mH$^+$ 303 (100%);

benzyl 1S-[(cyano)(phenyl)methylcarbamoyl]-3-methylbutylcarbamate (Compound 98); Proton NMR (300 MHz, DMSO-d$_6$): δ_9.42_(2d, 1H), 7.57 (m, 1H), 7.35–7.50 (m, 10H), 6.15 (2d, 1H), 5.02 (ABq, 2H), 4.08 (m, 1H), 1.32–1.61 (m, 3H), 0.90 (m, 6H);

benzyl (S)-N-(1-cyanomethylcarbamoyl-3-methylbutyl)-N-methylcarbamate (Compound 99); Proton NMR (300 MHz, DMSO-d$_6$): δ8.78 (bt, 1H), 7.4 (bs, 5H), _5.05 (m, 2H), 4.56_(m, 1H), 4.10 (d, 2H), 2.75 (s, 3H), 1.3–1.72 (m, 3H), 0.86 (m, 6H).MS (CI): mH$^+$ 318;

benzyl 2S-cyanomethylcarbamoyl-4-oxopyrrolidine-1-carboxylate (Compound 100); Proton NMR (270 MHz, DMSO-d$_6$): δ_8.99_(t, 1H), 7.34 (m, 5H), 5.12 (ABq, 2H), 4.68 (apparent t, 1H), 4.15 (m, 2H), 3.79–4.02 (m, 2H), 3.15 (m, 1H), 2.39 (m, 1H);

N-(1S-cyanomethylcarbamoylpentyl)benzenesulfonamide (Compound 101) Proton NMR (270 Mz, DMSO-d$_6$): δ_8.66, 8.60 (2t's, 1H), 8.10, 8.14 (2d's, 1H), 7.51–7.91 (m, 5H), 4.11, 3.98 (2d's, 2H), 3.73, 3.62 (2m's, 1H), 0.71–1.50 (m, 9H). APT 13C NMR (67 MHz, DMSO-d$_6$): δ_172.6, 172.1, 171.2, 141.7, 141.4, 132.9, 129.5, 129.3, 127.0, 118.0, 117.8, 56.4, 52.6, 33.0, 32.5, 32.1, 27.6, 27.5, 22.2, 22.0, 14.4, 14.2;

benzyl 2S-cyanomethylcabamoyl-4-ethylpyrrole-1-carboxylate (Compound 102); Proton NMR (300 MHz, DMSO-d$_6$): δ_8.78 (m, 1H), 7.37 (m, 5H), 5.04 (m, 2H), 3.95–4.40 (m, 3H), 3.74 (apparent t, 1H), 2.94 (m, 1H), 2.40 (m, 1H), 2.03 (m, 1H), 1.4 (m, 3H), 0.78 (m, 3H). APT 13C NMR (67 MHz, DMSO-d$_6$): δ_173.7, 173.3, 129.0, 128.9, 128.4, 128.2, 127.7, 118.1, 66.6, 60.7, 60.3, 53.1, 52.6, 39.5, 37.6, 27.6, 25.6, 12.9;

N-(1S-cyanomethylcarbamoylmethylbutyl-1-methylindole)-4-carboxamide (Compound 103); Proton NMR (300 Mz, DMSO-d$_6$): δ_8.74 (t, 1H), 8.44 (d, 1H), 8.20 (s, 1H), 7.75 (d, 1H), 7.48 (d, 1H), 7.43 (d, 1H), 6.56 (d, 1H), 4.53 (m, 1H), 4.16 (d, 2H), 3.84 (s, 3H), 1.47–1.77 (m, 3H), 0.88 (m, 6H);

N-1-(N-cyanomethyl-N-methylcarbamoyl)-3-methylbutyl-4-methylsulfonamide (Compound 104);

benzyl 1S-cyanomethylcarbamoyl-4-hydroxy-4-methylpyrrolidine-1-carboxylate (Compound 105); Proton NMR (300 MHz, DMSO-d$_6$): δ_8.65_(m, 1H), 7.36 (m, 5H), 5.03 (m, 2H), 4.2 (m, 1H), 4.09 (m, 2H), 3.35 (m, 2H), 2.1 (m, 1H), 1.91 (m, 1H), 1.22 (s, 3H). LCMS (electrospray) mH$^+$ 302 (100%);

benzyl 2S-cyanomethylcarbonyl-4-methylenepyrrolidine-1-carboxylate (Compound 106); Proton NMR (300 MHz, DMSO-d$_6$): δ_8.80 (m, 1H), 7.42 (m, 5H), 5.04 (m, 4H), 4.45 (m, 1H), 4.09 (m, 4H), 2.96 (m, 1H), 2.45 (m, 1H);

N-(1-cyanomethylcarbamoyl-2-methylpropylbenzamide (Compound 107); Proton NMR (300 MHz, DMSO-d$_6$): δ_8.82 (t, 1H), 8.47 (d, 1H), 7.9 (d, 2H), 7.46 (m, 3H), 4.2 (m, 3H), 2.12 (m, 1H), 0.92 (apparent t, 6H);

N-(1-cyanomethylcarbamoylpentyl)benzamide (Compound 108); Proton NMR (300 MHz, DMSO-d$_6$): δ_8.7 (t, 1H), 8.55 (d, 1H), 7.84 (d, 2H), 7.0 (m, 3H), 4.43 (m, 1H), 4.12 (d, 2H), 1.35–1.9 (m, 6H), 0.89 (t, 3H);

benzyl 1S-cyanomethylcabamoyl-2-hydroxypropylcarbamate (Compound 109); Proton NMR (300 MHz, DMSOd$_6$): δ_8.55 (t, 1H), 7.42 (m, 5H), 7.08 (d, 1H), 5.03 (ABq, 2H), 4.18 (m, 2H), 3.95 (d, 1H), 1.04 (d, 3H). MS (APCI): mH$^+$ 292;

benzyl 1S-(N-cyanomethyl-N-methylcarbamoyl-2-methylbutylcarbamate (Compound 112); Proton NMR (270 MHz, CDCl$_3$): δ7.31 (m, 5H), 5.51 (bd, 1H), 5.07 (ABq, 2H), 4.55 (m, 2H), 4.06 (d, 1H), 3.23 (s, 3H), 1.40–1.77 (m, 2H), 1.04–1.27 (m, 1H), 0.88 (m, 6H);

benzyl 1S-(N-cyanomethyl-N-methylcarbamoylpentylcarbamate (Compound 113); Proton NMR (270 MHz, CDCl$_3$): δ7.33 (s, 5H), 5.51 (bd, 1H), 5.08 (ABq, 2H), 4.65 (m, 1H), 4.51 (d, 1H), 4.14 (d, 1H), 3.21 (s, 3H), 1.51–1.77 (m, 2H), 1.32 (m, 4H), 0.88 (t, 3H);

(S)-N-(1-cyanomethylcarbamoyl-3-methylbutyl) acetamide (Compound 114); Proton NMR (270 MHz, DMSO-d$_6$): δ8.69 (t, 1H), 8.10 (d, 1H), 4.24 (apparent q, 1H), 4.10 (d, 2H), 1.84 (s, 3H), 1.40–1.50 (m, 3H), 0.84 (m, 6H). LCMS (electrospray): mH$^+$ 212;

N-(1S-cyanomethylcarbamoyl-3-methylbutyl)-guinoline-6-carboxamide (Compound 115);

4-amino-N-(1S-cyanomethylcarbamoyl-3-methylbutyl) benzamide (Compound 116);

pyrid-3-ylmethyl 1S-cyanomethylcarbamoyl-3-methybutylcarbamate (Compound 117); Proton NMR (300 MHz, DMSO-d$_6$): 8.77 (bb, 1H), 8.44 (m, 3H), 7.63 (m, 1H), 7.32 (m, 1H), 4.25 (m, 1H), 4.11 (m, 2H), 3.50 (ABq, 2H), 1.40–1.60 (m, 3H), 0.84 (dd, 6H); MS (electrospray): mH$^+$ 289 (100%);

N-(1S-cyanomethylcarbamoyl)-3-methylbutyl4-(1H-imidazol-4-yl)benzamide (Compound 118); $^1$H NMR (DMSO): δ0.85–0.91 ppm (d,d, 6 H), 1.45–1.8 ppm (m. 3 H), 2.99–3.02 ppm (m, 1 H), 4.12–4.14 ppm (d, 2 H), 4.5–4.6 ppm (m, 1 H), 7.89–7.92 ppm (d, 2 H), 8.02–8.05 ppm (d, 2H), 8.22 ppm (s, 1 H), 8.62–8.65 ppm (d, 1 H), 8.72–8.77 ppm (t, 1 H), 9.07 ppm (s, 1 H); LC/MS (339.9 M+H$^+$);

N-(1S-cyanomethylcarbamoyl-3-methylbutyl)-4-imidazol-1-ylbenzamide (Compound 119);

N-(1-cyanomethylcarbamoyl-2-methylpropyl)-4-(2-guanidinothiazol-4-yl)benzamide (Compound 120); $^1$H NMR (DMSO-d$_6$): 1.04 (m, 6H), 1.95 (m, 1H), 4.11 (m, 2H), 4.17 (m, 1H), 8.03 (m, 5H), 8.31 (m, 2H), 8.73 (d, 1H), 8.91 (d, 1H); ES-Ms: 400.1 (M+H$^+$);

N-(1-cyanomethylcarbamoyl-2-phenylethyl)-4-(2-guanidinothiazol-4-yl)benzamide (Compound 121); $^1$H NMR (DMSO-d$_6$): 1.04 3.01 (m, 1H), 4.01 (m, 2H), 4.17 (m, 1H), 7.12 (m, 5H), 8.03 (m, 5H), 8.31 (m, 2H), 8.73 (d, 1H), 8.91 (d, 1H); ES-Ms: 448.3 (M+H$^+$);

N-(1-cyanomethylcarbamoyl-2-methylbutyl)-4-(4-methylpiperazin-1-yl)benzamide (Compound 122); $^1$H NMR (DMSO-d$_6$): 1.04 0.95 (m, 6H), 1.15–1.35 (m, 3H), 2.81 (s, 3H), 3.31 (m, 4H), 3.81 (m, 4H), 4.01 (m, 2H), 4.17 (m, 1H), 7.01 (d, 2H), 7.73 (d, 2H), 8.41 (d, 1H), 9.01 (m, 1H); ES–Ms: 372.3 (M+H$^+$);

N-(1-cyanomethylcarbamoyl-2-phenylethyl)-4-(4-methylpiperazin-1-yl)benzamide (Compound 123); $^1$H NMR (DMSO): δ2.22 ppm (s, 3 H), δ2.43 ppm (m, 4 H), δ3.15–3.25 ppm (m, 4 H), δ4.12–4.13 ppm (d, 2 H), δ4.55–4.7 (m, 1 H), δ6.9–6.93 ppm (d, 2 H), δ7.1–7.3 ppm (m, 5 H), δ7.67–7.71 ppm (d, 2 H), δ8.35–8.38 ppm (d, 1 H), δ8.7–8.8 (t, 1 H); LC/MS (406 M+H$^+$);

N-(1-cyanomethylcarbamoyl-2-methylpropyl)-4-(4-methylpiperazin-1-yl)benzamide (Compound 124); $^1$H NMR (DMSO): δ0.86–0.91 ppm (t, 6 H), δ1.79–1.85 ppm (m. 31H), δ2.3 ppm (s, 3 H), δ2.5–2.7 ppm (m, 4 H), δ3.12–3.16 ppm (m, 4 H), δ4.12–4.14 ppm (d, 2 H), δ4.2–4.3 (m, 2 H), δ6.93–6.96 ppm (d, 2 H), δ7.77–7.8 ppm (d, 2 H), δ8.06–8.10 ppm (d, 1 H), δ8.74–8.76 ppm (t, 1 H); LC/MS (358 M+H$^+$);

N-(1-cyanomethylcarbamoyl)-3-methylbutyl)-4-(2-dimethylaminothiazol-4-yl)benzamide (Compound 125); $^1$H NMR (DMSO-d$_6$): 1.04): 0.96 (m, 6H), 1.85 (m, 3H), 3.32 (s, 6H), 4.01 (m, 2H), 4.37 (m, 2H), 7.02 (m, 1H), 7.51 (d, 2H), 8.03 (d, 2H), 8.83 (d, 2H), 10.11 (m, 1H); ES-Ms: 400.1 (M+H$^+$);

4-(2-aminothiazol-4-yl)-N-(1-cyanomethylcarbamoyl-3-methylbutyl)benzamide (Compound 126); $^1$H NMR (DMSO-d$_6$): 1.04 ): 0.91 (m, 6H), 1.78 (m, 3H), 4.01 (m, 2H), 4.27 (m, 2H), 7.02 (m, 1H), 7.31 (d, 2H), 7.83 (d, 2H), 8.53 (d, 2H), 9.81 (m, 2H); ES–Ms: 372.1 (M+H$^+$);

N-(1-cyanomethylcarbamoyl-3-methylbutyl)-3dimethylaminomethyl-1H-indole-5-carboxamide (Compound 127);

[1-S-(Cyanomethylcabamoyl)-3-methyl-butyl]-carbamic acid isobutyl ester (Compound 128);

N-[1-S-(Cyanomethyl-carbamoyl)-2-methyl-butyl]-4-dimethylamino-benzamide (Compound 129);

[1-S-(Cyanomethyl-carbamoyl)-3-methyl-butyl]-carbamic acid pyridin-4-ylmethyl ester (Compound 130); HNMR (Cl$_3$CD): 8.55 (2H, m), 7.22 (3H, m), 5.53 (1H, d), 5.09 (2H, m), 4.15 (1H, m), 4.12 (2H, m), 1.65 (3H, m), 0.89 (6H, m);

[1-S-(Cyanomethyl-carbamoyl)-3-methyl-butyl]-carbamic acid pyridin-3-ylmethyl ester (Compound 131); HNMR (Cl$_3$CD): 8.54 (2H, m), 7.65 (1H, d), 7.28 (2H, m), 5.61 (1H, d), 5.09 (2H, s), 4.15 (1H, m), 4.10 (2H, d), 1.52 (3H, m), 0.89 (6H, m)

[1-S-(Cyanomethyl-carbamoyl)-3-methyl-butyl]-carbamic acid pyridin-2-ylmethyl ester (Compound 132); HNMR (Cl$_3$CD): 8.56 (1H, m), 7.67 (1H, t), 7.28 (4H, m), 5.20 (2H, m), 4.21 (1H, m), 4.13 (2H, m), 1.57 (3H, m), 0.91 (6H, m);

[1-S-(Cyanomethyl-carbamoyl)-3-methyl-butyl]carbamic acid 4-fluoro-benzyl ester (Compound 133); H (Cl$_3$CD): 7.27 (2H, m), 7.06 (2H, t), 6.90 (1H, bs), 5.18 (1H, m), 5.05 (2H, m), 4.18 (1H, m), 4.12 (2H, d), 1.60 (3H, m), 0.91 (6H, t);

1-S-[1-(Cyanomethyl-carbamoyl)-3-methyl-butyl]-4-(2-pyridin-4-yl-ethylamino)-benzamide (Compound 134); $^1$H NMR (DMSO): δ0.81–0.94 ppm (d,d, 6 H), δ1.45–1.8 ppm (m. 3 H), δ3.12–3.19 ppm (t, 2H), δ3.4–3.51 ppm (t,m, 2 H), δ4.08–4.09 ppm (d, 2 H), δ4.45–4.51 ppm (m, 1 H), δ6.58–6.61 ppm (d, 2 H), δ7.69–7.72 ppm (d, 2 H), δ7.94–7.96 ppm (d, 2 H), δ8.6–8.7 ppm (t,m, 1 H), δ8.80–8.82 ppm (d, 2 H); LC/MS (394 M+H$^+$);

1-S-[1-(Cyanomethyl-carbamoyl)-3-methyl-butyl]-4-phenylamino-benzamide (Compound 135); $^1$H NMR (DMSO): δ0.79–0.94 ppm (m, 6 H), δ1.45–1.8 ppm (m. 3 H), δ4.08–4.12 ppm (m, 2 H), δ4.4–4.51 ppm (m, 1 H), δ7.2–7.33 ppm (m, 2 H), δ7.79–8.0 ppm (m, 2 H), δ8.55–8.6 ppm (m, 1 H), δ8.6–8.72 ppm (m, 1 H);

1-S-[1-(Cyanomethyl-carbamoyl)-3-methyl-butyl]-4-[(pyridin-3-ylmethyl)amino]-benzamide (Compound 136);

1-S-[1-(Cyanomethyl-carbamoyl)-3-methyl-butyl]-4-[(pyridin-2-ylmethyl)-amino]-benzamide (Compound 137); $^1$H NMR (DMSO): δ0.75–0.94 ppm (d,d, 6 H), δ1.45–1.8 ppm (m. 3 H), δ4.08–4.09 ppm (s, 2 H), δ4.42–4.47 ppm (m, 1 H), δ4.61 ppm (s, 2 H), δ6.60–6.63 ppm (d, 2 H), δ7.66–7.71 ppm (m, 4 H), δ8.15–8.24 ppm (m, 2 H), δ8.71–8.73 ppm (d, 1 H). LC/MS (380.1 M+H$^+$);

But-2-enedioic acid [1-S-(cyanomethyl-carbamoyl)-3-methyl-butyl]-amide phenylamide (Compound 138);

4-Methyl-piperazine-1-carboxylic acid {4-[1-S-(cyanomethyl-carbamoyl)-3-methyl-butylcarbamoyl]-phenyl}-amide (Compound 139);

[1-S-(Cyanomethyl-carbamoyl)-3-methyl-butyl]-carbamic acid 2-(4-methyl-thiazol-5-yl)-ethyl ester (Compound 140);

1-S-[1-(Cyanomethyl-carbamoyl)-3-methyl-butyl]-4-(1H-[1,2,4]triazol-3-ylamino)-benzamide (Compound 141); $^1$H NMR (DMSO): δ0.8–1.0 ppm (m, 6 H), δ1.10–1.2 ppm (m. 1 H), δ1.5–1.7 ppm (m, 3 H), δ4.12–4.2 ppm (m, 2 H), δ4.4–4.50 ppm (m, 1 H), δ7.6–7.68 ppm (m, 1 H), δ7.72–7.8 ppm (m 1 H), δ7.9–8.1 ppm (m, 2 H), δ8.7–8.8 ppm (m, 1 H); LC/MS (356 M+H$^+$);

1-[1-S-(Cyanomethyl-carbamoyl)-3-methyl-butyl]-4-(pyridin-4-ylmethoxy)-benzamide (Compound 142); $^1$H NMR (DMSO): δ0.83–0.88 ppm (m, 6 H), δ1.45–1.74 ppm (m. 3 H), δ4.09–4.10 ppm (m, 2 H), δ4.44–4.48 ppm (m, 1 H), δ5.46 ppm (s, 2 H), δ7.10–7.13 ppm (m, 2 H), δ7.84–7.95 ppm (m, 4 H), δ8.78–8.84 ppm (m 2 H); LC/MS (380.91 M+H$^+$);

1-[1-(Cyanomethyl-carbamoyl)-3-methyl-butyl]-2-nitro-benzamide (Compound 143); $^1$H-NMR (DMSO-d6): δ9.2 (d, 1H) δ8.9 (t, 1H) δ8.2 (d, 1H) δ7.9 (m, 3H) δ4.4 (d, 2H) δ1.6–2.0 (m, 3H), δ1.1 (m, J=10 Hz, 6H); MS (electrospray): mH+ 318.8 (100%);

[1-R-(Cyanomethyl-carbamoyl)-3-methyl-butyl] carbamic acid 1-methyl-piperidin-2-ylmethyl ester (Compound 144);

N-[1-(Cyanomethyl-carbamoyl)-3-methyl-butyl]-4-methoxy-benzamide (Compound 145); $^1$H NMR (DMSO-d$_6$, ppm): 0.86 (m, 6 H), 1.56–1.89 (m, 3 H), 3.81 (s, 3 H), 4.17 (m, 2 H), 4.47 (m, 1 H), 7.28 (m, 2 H), 8.11 (d, 2 H), 8.51 9m, 1 H), 8.89 (m, 1 H). ES–Ms: 303.1 (M+H$^+$);

[1-R-(Cyanomethyl-carbamoyl)-3-methyl-butyl]-carbamic acid furan-2-ylmethyl ester (Compound 146); HNMR (Cl$_3$CD): 7.55 (1H, m), 7.38 (1H, m), 6.37 (1H, m), 6.33 (1H, m), 5.66 (1H, d), 5.00 (2H, dd), 4.25 (1H, m), 4.10 (2H, d), 1.60 (3H, m), 0.90 (6H, m);

N-[1-S-(Cyanomethyl-carbamoyl)-3-methyl-butyl]-4-(3-pyridin-4-yl-propoxy)-benzamide (Compound 147);

N-[1-S-(Cyanomethyl-carbamoyl)-3-methyl-butyl]-3-(4-methyl-piperazine-1-sulfonyl)-benzamide (Compound 148);

N-[1-S-(Cyanomethyl-carbamoyl)-3-methyl-butyl]-4-(4-methyl-piperazin-1-ylmethyl)-benzamide (Compound 149);

N-[1-S-(Cyanomethyl-carbamoyl)-3-methyl-butyl]-4-[1-(4-methyl-piperazin-1-yl)-ethyl]-benzamide (Compound -150);

2-Amino-N-[1-(cyanomethyl-carbamoyl)-3-methyl-butyl-benzamide (Compound 151); ¹H-NMR (DMSO-d6): δ8.7 (t, 1H) δ8.3 (d, 1H) δ7.7 (d, 1H) δ7.2 (t, 1H) δ_6.8 (d, 1H) δ6.6 (t, 1H) δ4.2 (d, 2H) δ1.6–1.8 (m, 3H) δ0.9 (q, 6H); MS (electrospray) mH+ 288.7 (100%);

[1-S-(Cyanomethyl-carbamoyl)-3-methyl-butyl]-carbamic acid thiophen-3-ylmethyl ester (Compound 152); HNMR (Cl₃CD): 7.17 (2H, m), 7.05 (1H, m), 5.44 (1H, d), 5.08 (2H, m), 4.20 (1H, m), 4.08 (2H, d), 1.60 (3H, m), 0.91 (6H, m);

N-[1-S-(Cyanomethyl-carbamoyl)-3-methyl-butyl]-3-(4-methyl-piperazine-1-carbonyl)-benzamide (Compound 153);

N-{4-[1-S-(Cyanomethyl-carbamoyl-3-methyl-butylcarbamoyl]-phenyl}-isonicotinamide (Compound 154); ¹H NMR (DMSO-d₆, ppm): 0.86 (m, 6 H), 1.56–1.89 (m, 3 H), 4.17–4.33 (m, 3 H), 7.89–8.13 (m, 6 H), 8.81 (m, 2 H), 8.51 (m, 1 H), 9.01 (m, 1 H), 11.10 (m, 1 H). ES–Ms: 394.1 (M+H⁺);

N-[1-S-(Cyanomethyl-carbamoyl)-3-methyl-butyl]-4-(2-pyridin-3-yl-acetylamino)-benzamide (Compound 155); ¹H NMR (DMSO-d₆, ppm): 0.86 (m, 6 H), 1.56–1.89 (m, 3 H), 4.11 (s, 2 H), 4.17 (s, 2 H), 4.43 (m, 1H), 7.89–8.13 (m, 4 H), 8.61 (m, 2 H), 8.81 (m, 3 H), 11.10 (m, 1 H). ES–Ms: 408.1 (M+H⁺);

[1-S-(Cyanomethyl-carbamoyl)-2-methyl-butyl]-carbamic acid tert-butyl ester (Compound 156);

[1-R-(Cyanomethyl-carbamoyl)-3-methyl-butyl]-carbamic acid thiophen-2-ylmethyl ester (Compound 157); HNMR (Cl₃CD): 7.32 (1H, m), 7.07 (1H, m), 6.98 (1H, m), 5.26 (2H, s), 5.10 (1H, m), 4.14 (2H, m), 1.66 (3H, m), 0.91 (6H, m);

N-[1-S-(Cyanomethyl-carbamoyl)-3-methyl-butyl]-4-(4-methyl-piperazine-1-sulfonyl)-benzamide (Compound 158);

N-[1-S-(Cyanomethyl-carbamoyl)-3-methyl-butyl]-4-(4-methyl-piperazine-1-carbonyl)-benzamide (Compound 159);

N-[1-S-(Cyanomethyl-carbamoyl)-3-methyl-butyl]-4-(3-pyridin-4-ylmethyl-ureido)-benzamide (Compound 160); ¹H NMR (DMSO-d₆, ppm): 0.86 (m, 6 H), 1.56–1.89 (m, 3 H), 4.11 (s, 2 H), 4.13 (m, 1 H), 4.17 (s, 2 H), 7.89–8.13 (m, 4 H), 8.41 (m, 2 H), 8.81 (m, 3 H), 9.10 (m, 2 H), 10.15 (m, 1 H). ES-Ms: 408.1 (M+H⁺);

[1-S-(Cyanomethyl-carbamoyl)-3-methyl-butyl]-carbamic acid 3-pyridin-4-yl-propyl ester (Compound 161); HNMR (Cl₃CD): 8.50 (2H, d), 7.15 (2H, d), 7.08 (1H, m), 5.14 (1H, d), 4.16 (2H, d), 4.10 (2H, t), 2.69 (2H, t), 1.96 (2H, m), 1.60 (3H, m), 0.92 (6H, m);

[1-S-(Cyanomethyl-carbamoyl)-3-methyl-butyl]-carbamic acid 3-pyridin-3-yl-propyl ester (Compound 162); H¹MR (dmso-d₆): 8.65 (1H, t), 8.41 (1H, d), 7.63 (1H, d), 7.40 (1H, d), 7.31 (1H, m), 4.11 (2H, d), 4.00 (1H, m), 3.94 (2H, t), 2.65 (2H, t), 1.86 (2H, m), 1.50 (3H, m), 0.87 (6H, m);

[1-S-(Cyanomethyl-carbamoyl)-3-methyl-butyl-carbamic acid 2-((pyridine-4-carbonyl)-amino]-ethyl ester (Compound 163); ¹HNMR (dmso-d₆): 9.00 (1H, t), 8.84 (2H, m), 8.65 (1H, t), 7.91 (2H, d), 7.42 (1H, d), 4.12 (4H, m), 4.0 (1H, m), 3.50 (2H, m), 1.60 (1H, m), 1.43 (2H, m), 0.83 (6H, m);

4-Amino-N-[1-R-(cyanomethyl-carbamoyl)-3-methyl-butyl]-benzamide (Compound 164);

N-[1-(Cyanomethyl-carbamoyl)-2-methyl-butyl]-4-(2-pyridin-4-yl-ethylamino)-benzamide (Compound 166);

Cyclopropanecarboxylic acid [1-S-(cyanomethyl-carbamoyl)-2-methyl-butyl]-amide (Compound 167);

Cyclopropanecarboxylic acid [1-S-(cyanomethyl-carbamoyl)-3-methyl-butyl]-amide (Compound 168);

4-Amino-N-[1-(cyanomethyl-carbamoyl)-2-methyl-butyl]-benzamide (Compound 169);

N-[1-S-(Cyanomethyl-carbamoyl)-3-methyl-butyl]-4-(3-pyridin-3-yl-propoxy)-benzamide (Compound 170); ¹H NMR (DMSO): δ0.84–0.91 ppm (d,d, 6 H), δ1.49–1.8 ppm (m. 3 H), δ1.98–2.11 ppm (m, 2 H), δ2.72–2.8 ppm (m, 2 H), δ2.88 ppm (s, 1 H) δ3.98–4.09 ppm (m, 2 H), δ4.10–4.12 ppm (d, 2 H), δ4.47–4.54 (m, 1 H), δ6.97–7.01 ppm (d, 2 H), δ7.29–7.33 ppm (m, 1 H), δ7.65–7.68 ppm (d, m 1 H), δ7.86–7.90 ppm (d, 2 H), δ8.35–8.41 ppm (m, 2 H), δ8.45–8.46 ppm (m, 1 H), δ8.64–8.68 ppm (t, 1 H); LC/MS (409.4 M+H⁺);

3-Amino-N-[1-(cyanomethyl-carbamoyl)-3-methyl-butyl]-benzamide (Compound 171);

1,3-bis-{4-[1-(Cyanomethyl-carbamoyl)-3-methyl-butylcarbamoyl]-phenyl}-urea (Compound 172);

N-[1-S-(Cyanomethyl-carbamoyl)-2-methyl-butyl]-4-(pyridin-4-ylmethoxy)-benzamide (Compound 173);

N-[1-S-(Cyanomethyl-carbamoyl)-3-methyl-butyl]-4-(pyridin-2-ylmethoxy)-benzamide (Compound 174); ¹H NMR (DMSO): δ0.84–0.91 ppm (d,d, 6 H), δ1.49–1.8 ppm (m. 3 H), δ4.10–4.12 ppm (d, 2 H), δ4.4–4.52 (m, 1 H), δ5.25 ppm (s, 2 H), δ7.08–7.11 ppm (d, 2 H), δ7.34–7.37 ppm (m, 1 H), δ7.50–7.53 ppm (d, 1 H), δ7.8–7.90 ppm (m, 3 H), δ8.38–8.41 ppm (d, 1 H), δ8.55–8.60 ppm (d,m, 1 H), δ8.64–8.68 ppm (t, 1 H); LC/MS (381.02 M+H⁺);

5-Chloro-N-[1-S-(cyanomethyl-carbamoyl)-3-methyl-butyl]-2-nitro-benzamide (Compound 175); ¹H-NMR (DMSO-d6): δ9.3 (d, 1H) δ9.0 (m, 1H) δ8.3 (d 1H) δ8.0 (m, 2H) δ4.4 (d, 2H) δ1.6–2.0 (m, 3H) δ1.1 (m, 6H); MS (electrospray): mH+ 353.8 (100%);

N-[1-S-(Cyanomethyl-carbamoyl)-3-methyl-butyl-4-(2-pyridin-2-yl-ethoxy)-benzamide (Compound 176);

N-[1-S-(Cyanomethyl-carbamoyl)-3-methyl-butyl]-4-(2-pyrrolidin-1-yl-ethoxy)-benzamide (Compound 177); ¹H NMR (DMSO): δ0.84–0.94 ppm (d,d, 6 H), δ1.4–1.8 ppm (m. 3 H), δ1.8–1.91 ppm (m, 2H), δ1.98–2.10 ppm (m, 2 H), δ3.01–3.2 ppm (m, 2 H), δ4.11–4.13 ppm (d, 2 H), δ4.34–4.36 (d, 2 H), δ4.45–4.6 ppm (m, 1 H), δ7.05–7.09 ppm (d, 2 H), δ7.91–7.95 ppm (d, 2 H), δ8.42–8.45 ppm (d, 1 H), δ8.69–8.75 ppm (t, 1 H); LC/MS (386.6 M+H⁺);

N-[1-S-(Cyanomethyl-carbamoyl)-3-methyl-butyl]-4-(pyridin-3-ylmethoxy)-benzamide (Compound 178); ¹H NMR (DMSO): δ0.84–0.91 ppm (d,d, 6 H), δ1.5–1.8 ppm (m. 3 H), δ4.1–4.12 ppm (d, 2 H), δ4.44–4.55 ppm (m, 1 H), δ5.23 (s, 2 H), δ7.09–7.12 ppm (d, 2 H), δ7.42–7.45 ppm (m, 1 H), δ7.87–7.94 ppm (m, 3 H), δ8.39–8.42 ppm (d, 1 H), δ8.54–8.56 ppm (m, 1H), δ8.65–8.70 ppm (m, 2 H); LC/MS (380.4 M+H⁺);

[1-S-(Cyanomethyl-carbamoyl)-3-methyl-butyl]-carbamic acid 4-(3-pyridin-4-yl-propoxy)-benzyl ester (Compound 179); ¹HNMR (dmso-d₆): 8.67 (1H, t), 8.45 (2H, m), 7.48 (2H, d), 7.26 (4H, m), 6.90 (2H, d), 4.93 (2H, dd), 4.11 (2H, d), 4.00 (3H, m), 2.75 (2H, t), 2.01 (2H, m), 1.50 (3H, m), 0.85 (6H, m);

[1-S-(Cyanomethyl-carbamoyl)-3-methyy-butyl]-carbamic acid 4-(pyridin-4-ylmethoxy)-benzyl ester (Compound 180); ¹HNMR (dmso-d₆): 8.68 (1H, t), 8.56 (2H, m), 7.48 (1H, d), 7.42 (2H, d), 7.30 (2H, d), 7.01 (2H, d), 5.19 (2H, s), 4.94 (2H, dd), 4.11 (2H, d), 4.01 (1H, m), 1.50 (3H, m), 0.84 (6H, m);

N-[1-S-(Cyanomethyl-carbamoyl)-3-methyl-butyl]-3-nitro-benzamide (Compound 181);

N-[1-S-(Cyanomethyl-carbamoyl)-2-methyl-butyl]-3-nitro-benzamide (Compound 182);

N-[1-S-(Cyanomethyl-carbamoyl)-3-methyl-butyl]-4-pyridin-3-yl-benzamide (Compound 183); $^1$H NMR (DMSO-d$_6$, ppm): 0.86 (m, 6 H), 1.56–1.89 (m, 3 H), 4.13 (m, 2 H), 4.17 (m, 1 H), 7.76–7.81 (m, 6 H), 8.51 (m, 1 H), 8.86 (m, 3 H), 9.18 (m, 1 H). ES-Ms: 351.3 (M+H$^+$);

N-[1-S-(Cyanomethyl-carbamoyl)-3-methyl-butyl]-4-(3-pyridin-2-yl-propoxy)-benzamide (Compound 184); $^1$H NMR (DMSO): δ0.81–0.94 ppm (d,d, 6 H), δ1.5–1.8 ppm (m. 3 H), δ2.1–2.2 ppm (m, 2H), δ2.85–2.95 ppm (t, 2 H), δ4.07–4.19 ppm (m, 4 H), δ4.47–4.51 ppm (m, 1 H), δ6.96–7.00 ppm (d, 2 H), δ7.15–7.24 ppm (m, 1 H), δ7.25–7.3 ppm (d, 1 H), δ7.66–7.74 ppm (t,d, 1 H), δ7.84–7.9 ppm (d, 2 H), δ8.37–8.40 ppm (d, 1 H), δ8.48–8.51 ppm (d,m, 1 H), δ8.63–8.70 ppm (t, 1 H); LC/MS (408.4 M+H$^+$);

N-[1-(Cyanomethyl-carbamoyl)-3-methyl-butyl]-3-(pyridine-3-sulfonylamino)-benzamide (Compound 185); $^1$H-NMR (DMSO-d$_6$): δ10.6 (s, 1H) d 9.0–8.6 (m, 3H) δ8.5 (s, 1H) δ8.2 (d, 1H) δ7.6 (m, 3H) δ7.3 (m, 2H) δ4.1 (d, 2H) δ1.4–1.7 (m, 3H) δ0.9 (m, 6H); MS (electrospray): mH+ 429.5 (100%);

[1-S-(Cyanomethyl-carbamoyl)-3-methyl-butyl]-carbamic acid 1-methyl-pyridin-4-ylmethyl ester iodide salt (Compound 186); $^1$HNMR (dmso-d$_6$): 8.96 (2H, d), 8.77 (1H, t), 7.98 (2H, d), 7.92 (1H, d), 5.35 (2H, m), 4.31 (3H, s), 4.13 (2H, d), 4.04 (1H, m), 1.50 (3H, m), 0.88 (6H, m);

[1-S-(Cyanomethyl-carbamoyl)-3-methyl-butyl-carbamic acid 3-(1-methyl-pyridin-3-yl)-propyl ester iodide salt (Compound 187); $^1$HNMR (dmso-d$_6$): 8.92 (1H, s), 8.84 (1H, d), 8.69 (1H, t), 8.44 (1H, d), 8.05 (1H, m), 7.37 (1H, d), 4.31 (3H,s), 4.12 (2H, d), 4.00 (3H, m), 2.85 (2H, t), 1.95 (2H, m), 1.50 (3H, m), 0.86 (6H, m);

[1-S-(Cyanomethyl-carbamoyl)-3-methyl-butyl]-carbamic acid 3-(1-cyanomethyl-pyridin-3-yl)-propyl ester iodide salt (Compound 188); $^1$HNMR (dmso-d$_6$): 9.12 (1H, s), 9.05 (1H, d), 8.70 (1H, t), 8.62 (1H, d), 8.18 (1H, m), 7.37 (1H, d), 5.93 (2H, s), 4.12 (2H, d), 4.00 (3H, m), 2.89 (2H, m), 1.96 (2H, m), 1.50 (3H, m), 0.86 (6H, m);

[1-S-(Cyanomethyl-carbamoyl)-3-methyl-butyl]-carbamic acid 4-(pyridin-3-yloxy)-benzyl ester (Compound 189); $^1$HNMR (dmso-d$_6$): 8.69 (1H, t), 8.37 (2H, m), 7.55 (1H, d), 7.42 (4H, m), 7.07 (2H, d), 5.01 (2H, dd), 4.11 (2H, d), 4.02 (1H, m), 1.50 3H, m), 0.85 (6H, m);

N-[1-S-(Cyanomethyl-carbamoyl)-3-methyl-butyl]-3-(4-methoxy-benzenesulfonylamino)-benzamide (Compound 190); $^1$H-NMR (DMSO-d$_6$): δ10.3 (s, 1H) δ8.7 (t, 1H) δ8.5 (d, 1H) δ7.0–7.7 (m, 8H) δ4.4 (m, 1H) δ4.2 (d, 2H) δ1.5–1.7 (m, 3H) δ0.9 (m, 6H); MS (electrospray) mH+ 459.4 (100%);

N-{3-[1-S-(Cyanomethyl-carbamoyl)-3-methyl-butylcarbamoyl]-phenyl}-succinamic acid methyl ester (Compound 191);

N-{3-[1-S-(Cyanomethyl-carbamoyl)-3-methyl-butylcarbamoyl]-phenyl}-succinamic acid (Compound 192);

5-Pyridin-2-yl-thiophene-2-carboxylic acid [1-S-(cyanomethyl-carbamoyl)-3-methyl-butyl]-amide (Compound 193);

N-{3-[1-S-(Cyanomethyl-carbamoyl)-3-methyl-butylcarbamoyl]-phenyl}-succinamic acid (Compound 194);

1.3-bis-{3-[1-(Cyanomethyl-carbamoyl)-3-methyl-butylcarbamoyl]-phenyl}-urea (Compound 195);

N-[1-(Cyanomethyl-carbamoyl)-3-methyl-butyl]-3-(naphthalene-1-sulfonylamino)-benzamide (Compound 196); $^1$H-NMR (DMSO-d$_6$): δ10.6 (s, 1H) δ8.7 (t, 1H) δ8.6 (d, 1H) δ8.46 (s, 1H) δ8.1 (m, 3H) δ7.8 (m, 1H) δ7.5–7.8 (m, 4H) δ7.45 (m, 1H) δ7.25 (m 2H) δ4.4 (m, 1H) δ4.1 (d, 2H) δ1.4–1.7 (m, 3H) δ0.8 (q, J=11 Hz, 6H); MS (electrospray) mH+ 479.2 (100%);

N-[1-(Cyanomethyl-carbamoyl)-3-methyl-butyl]-3-(4-fluoro-benzenesulfonylamino)-benzamide (Compound 197); $^1$H-NMR (DMSO-d6): δ10.5 (s, 1H) δ8.7 (t, 1H) δ8.5 (d, 1H) δ7.8 (m, 2 H) δ7.6 (m, 2H) δ7.2–7.5 (m (br) 4 H), δ4.2 (m, 1H) δ4.1 (d, 2H) δ1.4–1.7 (m, 3H) δ0.9 (q, J=12 Hz, 6H); MS (electrospray) mH+ 447.4 (100%);

N-[1-S-(Cyanomethyl-carbamoyl)-3-methyl-butyl]-3-methoxy-benzamide (Compound 198); $^1$H NMR (DMSO): δ0.81–0.94 ppm (m, 6 H), δ1.44–1.80 ppm (m, 3 H), δ3.8 ppm (s, 3 H), δ4.10–4.14 ppm (d, 2 H), δ4.47–4.55 ppm (m, 1 H), δ7.01–7.13 ppm (d,d, 1 H), δ7.27–7.52 ppm (m, 4 H), δ8.47–8.6 ppm (d, 1. H), δ8.6–8.74 ppm (t, 1 H); LC/MS (303.4 M+H$^+$);

{4-[1-S-(Cyanomethyl-carbamoyl)-3-methyl-butylcarbamoyl]-phenyl}-carbamic acid 2-pyrrolidin-1-yl-ethyl ester (Compound 199); $^1$H NMR (DMSO-d$_6$, ppm): 0.86 (m, 6 H), 1.26–1.89 (m, 7 H), 3.31 (m, 2 H), 3.56–3.71 (m, 6 H), 4.09 (s, 2 H), 4.13 (m, 2 H), 4.17 (m, 1 H), 7.76 (m, 2 H), 7.81 (m, 2 H), 8.51 (m, 1 H), 8.86 (m, 1 H), 9.88 (m, 1 H), 10.15 (m, 1 H). ES-Ms: 430.3 (M+H$^+$);

{4-[1-S-(Cyanomethyl-carbamoyl)-3-methyl-butylcarbamoyl]-phenyl}-carbamic acid 3-pyridin-4-yl-propyl ester (Compound 200); $^1$H NMR (DMSO-d$_6$, ppm): 0.86 (m, 6 H), 1.26–1.89 (m, 3 H), 2.01 (m, 2 H), 3.01 (m, 2 H), 4.17 (m, 4 H), 4.57 (m, 1 H), 7.56 (m, 2 H), 7.81 (m, 4 H), 8.51 (m, 1 H), 8.86 (m, 3 H), 9.88 (m, 1 H). ES-Ms: 452.1 (M+H$^+$);

{4-[1-S-(Cyanomethyl-carbamoyl)-3-methyl-butylcarbamoyl]-phenyl}-carbamic acid 3-pyridin-3-yl-propyl ester (Compound 201); $^1$H NMR (DMSO-d$_6$, ppm): 0.86 (m, 6 H), 1.26–1.89 (m, 3 H), 2.01 (m, 2 H), 3.01 (m, 2 H), 4.17 (m, 4 H), 4.57 (m, 1 H), 7.66 (m, 2 H), 7.91 (m, 4 H), 8.31 (m, 1 H), 8.51 (m, 1 H), 8.86 (m, 3 H), 9.98 (m, 1 H). ES-Ms: 452.1 (M+H$^+$);

{4-[1-S-(Cyanomethyl-carbamoyl)-3-methyl-butylcarbamoyl]-phenyl}-carbamic acid 3-pyridin-2-yl-propyl ester (Compound 202); $^1$H NMR (DMSO-d$_6$, ppm): 0.86 (m, 6 H), 1.26–1.89 (m, 3 H), 2.01 (m, 2 H), 3.01 (m, 2 H), 4.17 (m, 4 H), 4.57 (m, 1 H), 7.56–7.91 (m, 6 H), 8.31 (m, 1 H), 8.51 (m, 1 H), 8.86 (m, 2 H), 9.98 (m, 1 H). ES-Ms: 452.1 (M+H$^+$);

{4-[1-S-(Cyanomethyl-carbamoyl)-3-methyl-butylcarbamoyl]-phenyl}-carbamic acid 1-methyl-piperidin-3-yl-methyl ester (Compound 203); $^1$H NMR (DMSO-d$_6$, ppm): 0.86 (m, 6 H), 1.26–1.89 (m, 8 H), 2.01 (m, 2 H), 3.51 (m, 7 H), 3.71 (m, 2 H), 4.17 (m, 4 H), 4.57 (m, 1 H), 7.66 (m, 2 H), 7.91 (m, 2 H), 8.11 (m, 1 H), 8.31 (m, 1 H) 9.16 (m, 1 H), 9.98 (m, 1 H). ES-Ms: 453.9 (M+H$^+$);

{4-[1-S-(Cyanomethyl-carbamoyl)-3-methyl-butylcarbamoyl]-phenyl}-carbamic acid 1-methyl-piperidin-2-yl-methyl ester (Compound 204); $^1$H NMR (DMSO-d$_6$, ppm): 0.86(m,6 H), 1.26–1.89 (m, 9 H), 2.01 (m, 2 H), 3.51 (m, 6 H), 3.71 (m, 2H), 4.17 (m, 4 H), 4.57 (m, 1 H), 7.56 (m, 2 H), 7.91 (m, 2 H), 8.21 (m, 1 H), 8.31 (m, 1 H), 9.36 (m, 1 H), 9.98 (m, 1 H). ES-Ms: 453.9 (M+H$^+$);

{4-[1-S-(Cyanomethyl-carbamoyl)-3-methyl-butylcarbamoyl]-phenyl}-carbamic acid pyridin-2-ylmethyl ester (Compound 205); ¹H NMR (DMSO-d₆, ppm): 0.86 (m, 6 H), 1.26–1.89 (m, 3 H), 4.17 (m, 2 H), 4.57 (m, 1 H), 5.12 (s, 2 H), 7.56–8.01 (m, 6 H), 8.51 (m, 1 H), 8.81 (m, 2 H), 9.98 (m, 1 H). ES-Ms: 424.1 (M+H⁺);

N-[1-S-(Cyanomethyl-carbamoyl)-3-methyl-butyl]-4-(pyridin-3-yloxy)-benzamide (Compound 206); ¹H NMR (DMSO): δ0.86–0.94 ppm (m, 6 H), δ1.42–1.8 ppm (m. 3 H), δ4.1 ppm (m, 2 H), δ4.5 ppm (m, 1 H), δ7.09–7.15 ppm (m, 2 H), δ7.44–7.6 ppm (m, 2 H), δ7.95–8.0 ppm (d,m 2 H), δ8.4 ppm (m, 1 H), δ8.5 ppm (m, 1 H), δ8.7 ppm (m, 1 H). LC/MS (366.2 M+H⁺);

{4-[1-S-(Cyanomethyl-carbamoyl)-3-methyl-butylcarbamoyl]-phenyl}-carbamic acid 2-pyridin-2-yl-ethyl ester (Compound 207); ES-Ms: 438.4 (M+H⁺);

[1-S-(Cyanomethyl-carbamoyl)-3-methyl-butyl]-carbamic acid 1-methyl-pyridin-3-ylmethy ester iodide salt (Compound 208); ¹HNMR (dmso-d₆): 8.98 (1H, s), 8.92 (1H, m), 8.76 (1H, m), 8.48 (1H, d), 8.15 (1H, m), 7.76 (1H, m), 5.20 (2H, m), 4.32 (3H, s), 4.11 (2H, m), 4.08 1H, m), 1.50 (3H, m), 0.90 (6H, m);

[1-S-(Cyanomethyl-carbamoyl)-3-methyl-butyl]-carbamic acid 1-carbonylmethyl-pyridin-3-ylmethyl ester bromide salt (Compound 209); ¹HNMR (dmso-d₆): 9.03 (0.5 H, s), 8.97 (0.5 H, d), 8.89 (1H, m), 8.59 (1H, d), 8.20 (1H, m), 8.12 (1H, s), 7.68 (1H, m), 7.65 (1H, bs), 7.30 (1H, bs), 5.40 (1H, s), 5.13 (1H), 4.15 2H, d), 4.00 (1H, m), 3.80 (2H, s), 1.50 (3H, m), 0.95 (6H, m);

N-[1-(Cyanomethyl-carbamoyl)-3-methyl-butyl]-4-(3-piperidin-4-yl-ureido)-benzamide (Compound 210);

[1-S-(Cyanomethyl-carbamoyl)-3-methyl-butyl]-carbamic acid 5-pyridin-2-yl-thiophen-2-ylmethyl ester (Compound 211); HNMR (Cl₃CD): 8.51 (1H, m), 7.85 (2H, m), 7.42(1H, m), 7.34 (1H, s), 7.20 (1H, m), 7.10 (2H, m), 5.22 (2H, m), 4.30 (3H, m), 1.70 (3H, m), 0.90 (6H, m);

4-Pyridin-4-yl-piperazine-1-carboxylic acid [1-S-(cyanomethyl-carbamoyl)-3-methyl-butyl]-amide (Compound 212);

2-(2-Nitro-phenyl)-thiazole-4-carboxylic acid [1-R-(cyanomethyl-carbamoyl)-2-naphthalen-2-yl-ethyl]-amide (Compound 213);

Morpholine-4-carboxylic acid [1-S-(cyanomethyl-carbamoyl)-2-naphthalen-2-yl-ethyl]-amide (Compound 214);

Benzofuran-2-carboxylic acid [1-(cyanomethyl-carbamoyl)-3-methyl-butyl]-amide (Compound 215); ¹HNMR (dmso-d₆): 8.80 1H, m), 7.79 (1H, d), 7.67 (3H, m), 7.48 (1H, m), 7.35 (1H, t), 4.53 (1H, m), 4.14 (2H, m), 1.65 (3H, m), 0.90 (6H, m);

Morpholine-4-carboxylic acid {4-[1-(cyanomethyl-carbamoyl)-3-methyl-butylcarbamoyl]-phenyl}-amide (Compound 216);

N-[1-(Cyanomethyl-carbamoyl)-3-methyl-butyl]-4-[3-(3-morpholin-4-yl-propyl)-ureido-benzamide (Compound 217);

N-[1-(Cyanomethyl-carbamoyl)-3-methyl-butyl]-4-(3-pyridin-3-ylmethyl-ureido)-benzamide (Compound 218);

N-[1-(Cyanomethyl-carbamoyl)-3-methyl-butyl]-4-[3-(1H-[1,2,4]triazol-3-yl)-ureido-benzamide (Compound 219);

N-[1-(Cyanomethyl-carbamoyl)-3-methyl-butyl]-4-(3,3dimethyl-ureido)-benzamide (Compound 220);

N-[1-(Cyanomethyl-carbamoyl)-3-methyl-butyl]-4-(3-pyridin-2-yl-ureido)-benzamide (Compound 221);

N-[1-(Cyanomethyl-carbamoyl)-3-methyl-butyl]-4-(3-pyridin-3-yl-ureido)-benzamide (Compound 222);

Quinoline-2-carboxylic acid [1-R-(cyanomethyl-carbamoyl)-3-methyl-butyl]-amide (Compound 223); ¹HNMR (dmso-d₆): 8.88 (2H, m), 8.60 (1H, d), 8.15 (3H, m), 8.09 (1H, m), 7.74 (1H, m), 4.66 (1H, m), 4.17 (2H, d), 1.80 (1H, m), 1.65 (2H, m), 0.92 (6H, m);

Quinoline-4-carboxylic acid [1-R-(cyanomethyl-carbamoyl)-3-methyl-butyl]-amide (Compound 224); ¹HNMR (dmso-d₆): 9.06 (1H, d), 9.01 (1H, d), 8.87 (1H, t), 8.16 (1H, d), 8.08 (1H, d), 7.81 (1H, m), 7.67 (1H, m), 7.58 (1H, d), 4.61 (1H, m), 4.22 (2H, d), 1.60 (3H, m), 0.94 (6H, m);

N-[1-S-(Cyanomethyl-carbamoyl)-2-naphthalen-2-yl-ethyl]-4-morpholin-4-yl-benzamide (Compound 225);

N-[1-(Cyanomethyl-carbamoyl)-3-methyl-butyl]-4-(3-[1,3,4]thiadiazol-2-yl-ureido)-benzamide (Compound 226);

N-[1-(Cyanomethyl-carbamoyl)-3-methyl-butyl]-4-(3-thiazol-2-yl-ureido)-benzamide (Compound 227);

N-[1-(Cyanomethyl-carbamoyl)-3-methyl-butyl]-4-(3-furan-2-ylmethyl-ureido)-benzamide (Compound 228);

N-[1-(Cyanomethyl-carbamoyl)-3-methyl-butyl]-4-{3-[2-(1H-indol-3-yl)-ethyl]-ureido}-benzamide (Compound 229);

N-[1-(Cyanomethyl-carbamoyl)-3-methyl-butyl]-4-(3-pyridin-2-ylmethyl-ureido)-benzamide (Compound 230);

Thiomorpholine-4-carboxylic acid {4-[1-(cyanomethyl-carbamoyl)-3-methyl-butylcarbamoyl]-phenyl}-amide (Compound 231);

N-[1-(Cyanomethyl-carbamoyl)-3-methyl-butyl]-4-ureido-benzamide (Compound 232);

{4-[1-(Cyanomethyl-carbamoyl)-3-methyl-butylcarbamoyl]-phenyl}-carbamic acid methyl ester (Compound 233);

N-[1-(Cyanomethyl-carbamoyl)-3-methyl-butyl]-3-ureido-benzamide (Compound 234);

N-[1-(Cyanomethyl-carbamoyl)-3-methyl-butyl]-3-(3,3dimethyl-ureido)-benzamide (Compound 235);

Morpholine-4-carboxylic acid {3-[1-(cyanomethyl-carbamoyl)-3-methyl-butylcarbamoyl]-phenyl}-amide (Compound 236);

Thiomorpholine-4-carboxylic acid {3-[1-(cyanomethyl-carbamoyl)-3-methyl-butylcarbamoyl]-phenyl}-amide (Compound 237);

N-[1-(Cyanomethyl-carbamoyl)-3-methyl-butyl]-3-[3-(3-morpholin-4-yl-propyl)-ureido]-benzamide (Compound 238);

N-[1-(Cyanomethyl-carbamoyl)-3-methyl-butyl]-3-(3-pyridin-2-yl-ureido)-benzamide (Compound 239);

N-[1-(Cyanomethyl-carbamoyl)-3-methyl-butyl]-3-(3-pyridin-3-yl-ureido)-benzamide (Compound 240);

N-[1-(Cyanomethyl-carbamoyl)-3-methyl-butyl]-3-(3-pyridin-4-ylmethyl-ureido)-benzamide (Compound 241);

N-[1-(Cyanomethyl-carbamoyl)-3-methyl-butyl]-3-(3-furan-2-ylmethyl-ureido)-benzamide (Compound 242);

N-[1-(Cyanomethyl-carbamoyl)-3-methyl-butyl]-3-{3-[2-(1H-indol-3-yl)-ethyl]-ureido}-benzamide (Compound 243);

N-[1-(Cyanomethyl-carbamoyl)-3-methyl-butyl]-3-{3-[2-(1H-imidazol-4-yl)-ethyl]-ureido}-benzamide (Compound 244);

N-[1-(Cyanomethyl-carbamoyl)-3-methyl-butyl]-4-{3-[2-(3H-imidazol-4-y)-ethyl]-ureido}-benzamide (Compound 245);

N-[1-(Cyanomethyl-carbamoyl)-3-methyl-butyl]-4-[3-(5-methyl-pyrazin-2-ylmethyl)-ureido]-benzamide (Compound 246);

4-Dimethylamino-piperidine-1-carboxylic acid {3-[1-(cyanomethyl-carbamoyl)-3-methyl-butylcarbamoyl]-phenyl}-amide (Compound 247);

N-[1-(Cyanomethyl-carbamoyl)-3-methyl-butyl]-3-(3-pyridin-2-ylmethyl-ureido)-benzamide (Compound 248);

N-[1-(Cyanomethyl-carbamoyl)-3-methyl-butyl]-3-(3-pyridin-3-ylmethyl-ureido)-benzamide (Compound 249);

4-(1-Aza-bicyclo[2.2.2]oct-1-ylmethyl)-N-[1-S-(cyanomethyl-carbamoyl)-3-methyl-butyl]-benzamide bromide salt (Compound 250); $^1$HNMR (dmso-d$_6$): 8.78 (1H, t), 8.69 (1H, d), 8.05 (2H, d), 7.61 (2H, d), 4.57 (1H, m), 4.48 (2H, s), 4.14 (2H, d), 3.47 (6H, m), 2.04 (1H, bs), 1.85 (6H, m), 1.60 (3H, m), 0.89 (6H, m);

N-[1-S-(Cyanomethyl-carbamoyl)-3-methyl-butyl]-4-(3-hydroxymethyl-pyridin-1-ylmethyl)-benzamide bromide salt (Compound 251); $^1$HNMR (dmso-d$_6$): 9.16 (1H, s), 8.70 (1H, d), 8.54 (1H, d), 8.16 (1H, t), 7.99 (2H, d), 7.65 (2H, d), 5.95 (2H, s), 4.72 (2H, s), 4.50 (1H, m), 4.12 (2H, d), 1.60 (3H, m), 0.88 (6H, m);

N-[1-S-(Cyanomethyl-carbamoyl)-3-methyl-butyl]-4-(4-methyl-morpholin-4-ylmethyl)-benzamide bromide salt (Compound 252); $^1$HNMR (dmso-d$_6$): 9.30 (1H, m), 9.20 (1H, m), 8.14 (2H, d), 7.66 (2H, d), 4.74 (2H, bs), 4.57 (1H, m), 4.11 (2H, bs), 3.97 (2H, bs), 3.56 (2H, bs), 3.38 (4H, s), 3.07 (3H, bs), 1.80 (1H, m), 1.56 (2H, m), 0.88 (6H, m);

N-[1-S-(Cyanomethyl-carbamoyl)-3-methyl-butyl]-4-(3-dimethylamino-phenoxy)-benzamide (Compound 253); $^1$H NMR (DMSO): δ0.81–0.89 ppm (d,d, 6 H), δ1.46–1.73 ppm (m. 3 H), δ2.85 ppm (s, 6 H), δ4.08–4.1 ppm (d, 2 H), δ4.42–4.5 (m, 1 H), δ6.24–6.27 ppm (d, 1 H), δ6.275 ppm (s, 1 H), δ6.5–6.53 ppm (d, 1 H), δ6.97–7.00 ppm (d, 2 H), δ7.14–7.17 ppm (t, 1 H), δ7.88–7.91 ppm (d, 2 H), δ8.43–8.48 ppm (d, 1 H), δ8.65–8.68 ppm (t, 1 H); LC/MS (408.2 M+H$^+$);

N-[1-S-(Cyanomethyl-carbamoyl)-3-methyl-butyl]-3-(3-pyridin-3-yl-propoxy)-benzamide (Compound 254); $^1$H NMR (DMSO): δ0.84–0.89 ppm (d,d, 6 H), δ1.46–1.74 ppm (m. 3 H), δ1.95–2.07 ppm (m, 2 H), δ2.73–2.78 ppm (t, 2 H), δ3.97–4.03 ppm (m, 2 H), δ4.08–4.10 ppm (d, 2 H), δ4.43–4.5 (m, 1 H), δ7.06–7.08 ppm (d, 1 H), δ7.26–7.37 ppm (m, 2 H), 7.63–7.66 ppm (m, 1 H), δ8.36–8.38 ppm (m, 1 H), δ8.43 ppm (s, 1 H), δ8.52–8.55 ppm (d, 1 H), δ8.66–8.69 ppm (m, 1 H); LC/MS (408.4 M+H$^+$);

Isoquinoline-1-carboxylic acid [1-S-(cyanomethyl-carbamoyl)-3-methyl-butyl]-amide (Compound 255); $^1$HNMR (dmso-d$_6$): 8.96 (1H, d), 8.88 (1H, t), 8.07 (2H, m), 7.84 (1H, t), 7.74 (1H, t), 4.64 (1H, m), 4.21 (2H, m), 1.65 (3H, m), 0.93 (6H, m);

N-[1-S-(Cyanomethyl-carbamoyl)-3-methyl-butyl]-4-pyridin-1-ylmethyl-benzamide iodide salt (Compound 256); $^1$HNMR (dmso-d$_6$): 9.20 (2H, d), 8.65 (1H, t), 8.20 (2H, t), 7.98 (2H, d), 7.62 (2H, d), 5.92 (2H, s), 4.50 (1H, m), 4.12 (2H, s), 1.50 (3H, m), 0.89 (6H, m);

Isoquinoline-3-carboxylic acid [1-S-(cyanomethyl-carbamoyl)-3-methyl-butyl]-amide (Compound 257); $^1$HNMR (dmso-d$_6$): 9.42 (1H, s), 8.85 (2H, m), 8.58 (1H, s), 8.27 (1H, d), 8.22 (1H, d), 7.86 (2H, m), 4.67 (1H, m), 4.17 (2H, d), 1.77 (1H, m), 1.61 (2H, m), 0.92 (6H, m);

4-Dimethylamino-piperidine-1-carboxylic acid {4-[1-(cyanomethyl-carbamoyl)-3-methyl-butylcarbamoyl]-phenyl}-amide (Compound 258);

N-[1-S-(Cyanomethyl-carbamoyl)-3-methyl-but-3-enyl]-4-fluoro-benzamide (Compound 259);

5-(3-Trifluoromethyl-phenyl)-furan-2-carboxylic acid [1-S-(cyanomethyl-carbamoyl)-3-methyl-butyl]-amide (Compound 260); $^1$H NMR (DMSO): δ0.8–1.0 ppm (m, 6 H), δ1.55–1.85 ppm (m. 3 H), δ4.14–4.16 ppm (d, 2 H), δ4.5–4.6 ppm (m, 1 H), δ7.3–7.4 ppm (d,d, 2 H), 7.7–7.8 ppm (m, 2 H), δ8.25–8.34 ppm (m, 2 H), δ8.7–8.9 ppm (m, 2 H);

N-[1-S-(Cyanomethyl-carbamoyl)-3-methyl-butyl]-3-phenoxy-benzamide (Compound 261); $^1$H NMR (DMSO): δ0.0.86–0.96 ppm (m, 6 H), δ1.42–1.8 ppm (m. 3 H), δ4.0–4.17 ppm (m, 2 H), δ4.5 ppm (m, 1 H), δ6.97–7.04 ppm (m, 2 H), δ7.12–7.19 ppm (m, 2 H), δ7.39–7.58 ppm (m 4 H), δ7.61–7.73 ppm (m, 1 H), δ8.56–8.73 ppm (m, 1 H); LC/MS (366 M+H$^+$);

N-[1-(Cyanomethy-carbamoyl)-3-methyl-but-3-enyl]-4-morpholin-4-yl-benzamide (Compound 262);

2-(2-Nitro-phenyl)-thiazole-4-carboxylic acid [1-S-(cyanomethyl-carbamoyl)-3-methyl-butyl]-amide (Compound 263); $^1$H NMR (DMSO): δ0.86–0.88 ppm (m, 6 H), δ1.5–1.7 ppm (m. 3 H), δ4.09–4.20 ppm (m, 2 H), δ4.39–4.55 ppm (m, 1 H), δ7.73–7.88 ppm (m, 2 H), δ7.87–7.99 ppm (m, 1 H), δ7.98–8.12 ppm (m 2 H), δ8.75–8.87 ppm (m, 1 H); LC/MS (402 M+H$^+$);

2-Benzo[1,3]dioxol-5-yl-oxazole-4-carboxylic acid [1-S-(cyanomethyl-carbamoyl)-3-methyl-butyl]-amide (Compound 264); $^1$HNMR (dmso-d$_6$): 8.81 (1H, t), 8.69 (1H, s), 8.22 (1H, d), 7.61 (1H, d), 7.53 (1H, s), 7.12 (1H, d), 6.16 (2H, s), 4.57 (1H, m,), 4.15 (2H, d), 1.60 (3H, m), 0.90 (6H, m);

Pyridine-2-carboxylic acid [1-S-(cyanomethyl-carbamoyl)-3-methyl-butyl]-amide (Compound 265); $^1$HNMR (dmso-d$_6$): 8.83 (1H, t), 8.70 (2H, m), 8.02 (2H, m), 7.66 (1H, m), 4.59 (1H, m), 4.15 (2H, d), 1.74 (1H, m), 1.58 (2H, m), 0.90 (6H, m);

{4-[1-S-(Cyanomethyl-carbamoyl)-3-methyl-butylcarbamoyl]-phenyl}-carbamic acid 2-morpholin-4-yl-ethyl ester (Compound 266); ES–Ms: 446.4 (M+H$^+$);

4-Methyl-2-S-[3-(4-phenyl-thiazol-2-yl)-ureido]-pentanoic acid cyanomethyl-amide (Compound 267); $^1$H NMR (DMSO-d$_6$, ppm): 0.86 (m, 6 H), 1.26–1.89 (m, 3 H), 4.17 (m, 2 H), 4.57 (m, 1 H), 5.12 (s, 2 H), 7.36–7.61 (m, 6 H), 7.81 (m, 2 H). ES-Ms: 372.1 (M+H$^+$);

2-(3-Nitrophenyl)-thiazole-4-carboxylic acid [1-S-(cyanomethyl-carbamoyl)-3-methyl-butyl]-amide (Compound 268); $^1$H NMR (DMSO): δ0.86–0.91 ppm (m, 6 H), δ1.56–1.64 ppm (m. 2 H), δ1.74–1.80 ppm (m, 1 H), δ4.11–4.4 ppm (d, 2 H), δ4.5–4.6 ppm (m, 1 H), δ7.79–7.85 ppm (m, 1 H), δ8.28–8.39 ppm (m, 1 H), δ8.41–8.52 ppm (m 2 H), δ8.57–8.68 ppm (m, 1 H), δ8.7–8.9 ppm (m, 2 H); LC/MS (423.8 M+Na$^+$);

4-Hydroxy-quinoline-2-carboxylic acid [1-R-(cyanomethyl-carbamoyl)-3-methyl-butyl]-amide (Compound 269);

6-Hydroxy-pyridine-2-carboxylic acid [1-R-(cyanomethyl-carbamoyl)-3-methyl-butyl]-amide (Compound 270); $^1$HNMR (dmso-d$_6$): 11.00 (1H, s), 8.95 (1H, bs), 7.79 (1H, bs), 6.84 (1H, bs), 4.55 (1H, bs), 4.16 (2H, m), 1.58 (3H, m), 0.90 (6H, m);

Quinoxaline-2-carboxylic acid [1-R-(cyanomethyl-carbamoyl)-3-methyl-butyl]-amide (Compound 271); $^1$HNMR (dmso-d$_6$): 9.48 (1H, s), 9.00 (1H, d), 8.85 (1H, t), 8.25 (2H, m), 8/02 (2H, m), 4.66 (1H, m), 4.17 (2H, m), 1.84 (1H, m), 1.65 (2H, m), 0.93 (6H, m);

3-Hydroxy-pyridine-2-carboxylic acid [1-R-(cyanomethyl-carbamoyl)-3-methyl-butyl]-amide (Compound 272); $^1$HNMR (dmso-d$_6$): 9.03 (1H, d), 8.84 (1H, t), 8.21 (1H, d), 7.56 (1H, dd), 7.45 (1H, d), 4.57 (1H, m), 4.16 (2H, d), 1.78 (1H, m), 1.60 (2H, m), 0.90(6H, m);

8-Hydroxy-quinoline-2-carboxylic acid 1-R-(cyanomethyl-carbamoyl)-3-methyl-butyl]-amide (Compound 273); $^1$HNMR (dmso-d$_6$): 9.68 (1H, d), 8.52 (1H, d), 8.15 (1H, d), 7.54 (2H, m), 7.20 (1H, d), 4.65 (1H, m), 4.15 (2H, s), 1.71 (3H, m), 0.92 (6H, m);

N-[1-S-(Cyanomethyl-carbamoyl)-3-methyl-butyl]-3-(2-dimethylamino-thiazol-5-yl)-benzamide (Compound 274);

4'-Trifluoromethyl-biphenyl-2-carboxylic acid [1-S-(cyanomethyl-carbamoyl)-3-methyl-butyl]-amide (Compound 275); $^1$H NMR (DMSO): δ0.66–0.74 ppm (m, 6 H), δ1.06–1.28 ppm (m. 2 H), δ1.35–1.45 (m, 1 H), δ2.75 (m, 1H), δ4.09–4.12 ppm (m, 2 H), δ4.17–4.25 ppm (m, 1 H), δ7.32–7.61 ppm (m, 8 H), δ7.7–7.76 ppm (m, 2 H), δ7.78 ppm (m 1 H), δ8.48–8.51 ppm (m, 1 H), δ8.6–8.65 ppm (m, 1 H); LC/MS (440.2 M+Na$^+$);

{4-[1-S-(Cyanomethyl-carbamoyl)-3-methyl-butylcarbamoyl]-phenyl}-carbamic acid 1-methyl-pyrrolidin-2-ylmethyl ester (Compound 276); ES-Ms: 429.4 (M+H$^+$);

{4-[1-S-(Cyanomethyl-carbamoyl)-3-methyl-butylcarbamoyl]-phenyl}-carbamic acid 2-(1-methyl-pyrrolidin-2-yl)-ethyl ester (Compound 277); $^1$H NMR (DMSO-d$_6$, ppm): 0.86 (m, 6 H), 1.26–1.89 (m, 9 H), 2.01 (m, 2 H), 3.51 (m, 6 H), 4.17 (m, 2 H), 4.57 (m, 1 H), 7.56 (m, 2 H), 7.91 (m, 2 H), 8.21 (m, 1 H), 8.31 (m, 1 H). ES–Ms: 443.9 (M+H$^+$);

2-(Pyridin-4-ylamino)-thiazole-4-carboxylic acid [1-S-(cyanomethyl-carbamoyl)-3-methyl-butyl]-amide (Compound 278);

N-[1-S-(Dicyanomethyl-carbamoyl)-3-methyl-butyl]-4-morpholin-4-yl-benzamide (Compound 279);

2-(3-Amino-phenyl)-thiazole-4-carboxylic acid [1-S-(cyanomethyl-carbamoyl)-3-methyl-butyl]-amide (Compound 280); $^1$H NMR (DMSO): δ0.78–0.94 ppm (m, 6 H), δ1.5–1.75 ppm (m. 3 H), δ4.12–4.14 ppm (d, 2 H), δ4.51–4.59 ppm (m, 1 H), δ5.37 ppm (m, 1 H), δ6.67–6.69 ppm (m, 1 H), δ7.11–7.20 ppm (m, 2 H), δ8.24–8.28 ppm (m, 1 H), δ8.8–8.85 ppm (m, 1 H); LC/MS (371.6 M+H$^+$);

2-(2-Amino-phenyl)-thiazole-4-carboxylic acid [1-S-(cyanomethyl-carbamoyl)-3-methyl-butyl]-amide (Compound 281); $^1$H NMR (DMSO): δ0.81–0.94 ppm (m, 6 H), δ1.52–1.65 ppm (m. 2 H), δ1.74–1.82 ppm (m, 1H), δ4.10–4.14 ppm (m, 2 H), δ4.47–4.55 ppm (m, 1 H), δ6.55–6.6 ppm (t, 1 H), δ6.83–6.86 ppm (m, 1 H), δ7.11–7.17 ppm (t,m 1 H), δ7.51–7.56 ppm (d, 1 H), δ8.2 ppm (m, 1 H), δ8.66–8.71 ppm (m, 2 H); LC/MS (372.2 M+H$^+$);

2-Pyridin-3-yl-benzooxazole-6-carboxylic acid [1-S-(cyanomethyl-carbamoyl)-3-methyl-butyl]-amide (Compound 282); $^1$HNMR (dmso-d$_6$): 9.40 (1H, d), 8.85 (1H, m), 0.75 (2H, m), 0.58 (1H, m), 8.40 (1H, s), 8.05 (1H, d), 7.94 (1H, d), 7.70 (1H, m), 4.56 (1H, m), 4.15 (2H, d), 1.70 (3H, m), 0.92 (6H, m);

2(1-Methyl-pyridin-3-yl)-benzooxazole-6-carboxylic acid [1-S-(cyanomethyl-carbamoyl-3-methyl-butyl]-amide iodide salt (Compound 283); $^1$HNMR (dmso-d$_6$): 9.91 (1H, s), 9.25 (1H, d), 9.19 (1H, d), 8.82 (2H, m), 8.42 (1H, s), 8.37 (1H, m), 8.13 (1H, d), 8.05 (1H, d), 4.57 (1H, m), 4.51 (3H, s), 4.16 (2H, m), 1.70 (3H, m), 0.92 (6H, m);

4-Methyl-2-S-[4-(4-nitro-phenyl)-thiazol-2-ylamino-pentanoic acid cyanomethyl-amide (Compound 284);

4-Methyl-2-S-(4-phenyl-thiazol-2-ylamino)-pentanoic acid cyanomethyl-amide (Compound 285);

4-Methyl-2-S-(4-pyridin-3-yl-thiazol-2-ylamino)-pentanoic acid cyanomethyl-amide (Compound 286);

4-Methyl-2-S-(4-pyridin-4-yl-thiazol-2-ylamino)-pentanoic acid cyanomethyl-amide (Compound 287);

[1-(Cyanomethyl-carbamoyl)-cyclopropyl]-carbamic acid benzyl ester (Compound 288);

[1-(Cyanomethyl-carbamoyl)-cyclopentyl-carbamic acid benzyl ester (Compound 289);

[1-(Cyanomethyl-carbamoyl)-cyclohexyl]-carbamic acid benzyl ester (Compound 290);

4-Methyl-2-S-[4-(3-nitro-phenyl)-thiazol-2-ylamino]-pentanoic acid cyanomethyl-amide (Compound 291);

2-S-[4-(3-Amino-phenyl)-thiazol-2-ylamino]-4-methyl-pentanoic acid cyanomethyl-amide (Compound 292);

Acetic acid 2-[1-S-(cyanomethyl-carbamoyl)-3-methyl-butylamino]-thiazol-4-ylmethyl ester (Compound 293);

N-[1-(Cyanomethyl-carbamoyl)-cyclopropyl]-4-morpholin-4-yl-benzamide (Compound 294); $^1$H NMR (DMSO-d6), δ8.71 (s, 1H), δ8.44 (s, 1H), δ7.77 (d, 2H), δ6.93 (d, 2H), δ4.02 (d, 2H), δ3.70 (s, br, 4H), δ3.17 (s, br, 4H), δ1.33 (s, br, 2H), δ0.98 (s, br, 2H);

[1-(Cyanomethyl-carbamoyl)-cyclohexyl]-carbamic acid tert-butyl ester (Compound 295); $^1$H NMR (DMSO-d6) δ8.09 (s, 1H), δ6.76 (s, 1H), δ4.00 (d, 2H), δ1.88–1.07 (m, 19H); MS: M+H$^+$282.0;

2-[4-S-(2,5-Dichloro-thiophen-3-yl)-thiazol-2-ylamino]-4-methyl-pentanoic acid cyanomethyl-amide (Compound 296);

{2-[1-S-(Cyanomethyl-carbamoyl)-3-methyl-butylamino]-thiazol-4-yl}-acetic acid ethyl ester (Compound 297);

N-[1-(Cyanomethyl-carbamoyl)-cyclohexyl]-4-morpholin-4-yl-benzamide (Compound 298); $^1$H NMR (DMSO-d6), δ8.11 (s, 1H), δ7.76(d, 2H), δ7.65 (s, 1H), δ6.93 (d, 2H), δ4.02 (d, 2H), δ3.70 (s, br, 4H), δ3.17 (s, br, 4H), δ2.15–1.04 (m, 10H); MS: M+H$^+$=370.6;

N-[1-S-(1-Cyano-2-oxo-propylcarbamoyl)-3-methyl-butyl]-4-morpholin-4-yl-benzamide (Compound 299);

Biphenyl-3-carboxylic acid [1-(1-cyano-2-oxo-propylcarbamoyl)-3-methyl-butyl]-amide (Compound 300);

[1-S-(1-Cyano-2-oxo-propylcarbamoyl)-3-methyl-butyl]-carbamic acid benzyl ester (Compound 301);

(3-{2-[1-S-(Cyanomethyl-carbamoyl)-3-methyl-butylamino]-thiazol-4-yl}-phenyl)-carbamic acid allyl ester (Compound 302);

{2-[1-S-(Cyanomethyl-carbamoyl-3-methyl-butylamino]-thiazol-4-yl}-acetic acid (Compound 303);

N-1-(Cyanomethyl-carbamoyl)-cyclohexyl]-4-dimethylamino-benzamide (Compound 304); $^1$H NMR (DMSO-d6), δ8.13 (s, 1H), δ7.73 (d, 2H), δ7.57 (s, 1H), δ6.68 (d, 2H), δ4.23–4.05 (s,br, 6H), δ4.02 (s, 2H), δ2.93 (s, br, 6H), δ2.17–1.03 (m, 10H); MS: M+H$^+$=329.4;

1-(3-Phenyl-propionylamino)-cyclohexanecarboxylic acid cyanomethyl-amide (Compound 305); $^1$H NMR (DMSO-d6), δ8.04 (s, 1H), δ7.65 (s, 1H), δ7.20 (m, 5H), δ4.00 (d, 2H), δ4.02 (s, 2H), δ2.77 (t, 2H), δ2.45 (s,br, 2H), δ1.95–1.07 (m, 10H); MS: M+H$^+$=314.0;

N-[1-(Cyanomethyl-carbamoyl)-cyclohexyl]-4-(4-methyl-piperazin-1-yl)-benzamide (Compound 306); $^1$H NMR (DMSO-d6), δ8.14(s, 1H), δ7.80 (d, 2H), δ7.73 (s, 1H), δ7.01 (d, 2H), δ4.08–3.80 (m, 4H), δ3.76–3.32 (m, 2H), δ3.20–2.91 (m, 4H), δ2.84 (s, 3H), δ2.17–1.09 (m, 10H); MS: M+H$^+$=384.2;

3-Bromo-N-[1-(cyanomethyl-carbamoyl)-cyclohexyl]-benzamide (Compound 307); $^1$H NMR (DMSO-d6), δ8.27–8.14 (m, 2H), δ8.08 (s, 1H), δ7.82 (d, 1H), δ7.71 (d, 1H), δ7.40 (t, 1H), δ4.02 (d, 2H), δ2.15–1.10 (m, 10H); MS: M+H$^+$=364.0 and 366.2;

N-[1-S-(1-Cyano-cyclopropylcarbamoyl)-3-methyl-butyl]-4-(4-methyl-piperazin-1-yl)-benzamide (Compound 308);

Biphenyl-3-carboxylic acid [1-(cyanomethyl-carbamoyl)-cyclohexyl]-amide (Compound 309); $^1$H NMR (DMSO-d6), δ8.22 (s,br, 1H), δ8.14 (d, 2H), δ7.81 (t, 2H), δ7.72 (d, 2H), δ7.58–7.33 (m, 4H), δ4.01 (d, 2H), δ2.17–1.13 (m, 10H): MS: M+H$^+$=362.0;

[1-S-(1-Cyano-cyclobutylcarbamoyl)-3-methyl-butyl-carbamic acid benzyl ester (Compound 310);

[1-S-(1-Cyano-cyclobutylcarbamoyl)-3-methyl-butyl-carbamic acid tert-butyl ester (Compound 311);

N-[1-S-(4-Cyano-tetrahydro-pyran-4-ylcarbamoyl)-3-methyl-butyl]-4-morpholin-4-yl-benzamide (Compound 312); $^1$H NMR (DMSO-d$_6$, ppm): 0.86 (m, 6 H), 1.26–1.89 (m, 7 H), 2.61 (m, 4 H), 3.51 (m, 8 H), 4.57 (m, 1 H), 7.56 (m, 2 H), 7.91 (m, 2 H), 8.41 (m, 1 H). ES–Ms: 428.9 (M+H$^+$);

N-[1-(1-Cyano-cyclopropylcarbamoyl)-cyclohexyl]-4-morpholin-4-yl-benzamide (Compound 313); $^1$H NMR (DMSO-d6), δ8.35(s, 1H), δ7.72 (d, 2H), δ7.55 (s, 1H), δ6.92 (d, 2H), δ3.93 (s, br, 7H), δ3.70 (s, br , 4H), δ3.17 (s, br, 4H), δ2.00–0.9 (m, 14H); MS: M+H$^+$=397.0;

4-Amino-N-[1-(cyanomethyl-carbamoyl)-cyclohexyl]-benzamide (Compound 314);

N-[1-(Cyanomethyl-carbamoyl)-cyclohexyl]-4-(4-methyl-piperazine-1-sulfonyl)-benzamide (Compound 315);

N-[1-(Cyanomethyl-carbamoyl)-cyclohexyl]-4-(4-methyl-piperazine-1-carbonyl)-benzamide (Compound 316);

4-Methyl-piperazine-1-carboxylic acid {4-]1-(cyanomethyl-carbamoyl)-cyclohexylcarbamoyl]-phenyl}-amide (Compound 317);

N-[1-S-(1-Cyano-cyclobutylcarbamoyl)-3-methyl-butyl]-4-morpholin-4-yl-benzamide (Compound 318);

4-[4-(4-Methyl-piperazin-1-yl)-benzoylamino]-tetrahydro-pyran-4-carboxylic acid cyanomethyl-amide (Compound 319); $^1$H NMR (DMSO-d$_6$, ppm): 1.76–1.89 (m, 4 H), 2.81 (s, 3 H), 2.91–3.31 (m, 4 H), 3.47–3.66 (m, 6 H), 4.07 (m, 4 H), 7.16 (m, 2 H), 7.81 (m, 2 H), 8.11 (m, 1 H), 8.41 (m, 1 H). ES-Ms: 386.0 (M+H$^+$);

N-[1-(1-Cyano-cyclopropylcarbamoyl)-cyclohexyl]-6-(4-methyl-piperazin-1-yl)-nicotinamide (Compound 320); $^1$H NMR (DMSO-d6), δ8.63(s, 1H), δ8.41 (s, 1H), δ8.03 (d, 1H), δ7.80 (s, 1H), δ6.95 (d, 2H), δ4.49 (d, 2H), δ4.20–3.71 (s, br,, 2H), δ3.49 (d, 2H), δ3.24–2.94 (m, 4H), δ2.56 (s, 3H), δ2.00–0.90 (m, 14H); MS: M+H=411.2;

N-[1-S-(1-Cyano-cyclobutylcarbamoyl)-3-methyl-butyl]-4-(4-methyl-piperazin-1-yl)-benzamide (Compound 321);

[1-(1-Cyano-cyclopropylcarbamoyl)-cyclohexyl]-carbamic acid tert-butyl ester (Compound 322); $^1$H NMR (DMSO-d6), δ8.37(s, 1H), δ6.64 (s, 1H), δ1.81–0.90 (m, 23H); MS: M+H=380.0;

[1-S-(4-Cyano-tetrahydro-thiopyran-4-ylcarbamoyl)-3-methyl-butyl]-carbamic acid benzyl ester (Compound 323); $^1$H NMR (DMSO-d6), δ8.48(s, 1H), δ7.48 (d, 1H), δ7.31 (s, 5H), δ4.99 (s, 2H), δ4.05 (m, 1H), δ2.78–2.57 (m, 4H), δ2.39 (m, 2H), δ1.95 (m, 2H), δ1.67–1.18 (m, 3H), δ0.94–0.074 (m, 6H); MS: M+H=390.2;

[1-S-(1-Cyano-4-methyl-cyclohexylcarbamoyl)-3-methyl-butyl]-carbamic acid benzyl ester (Compound 324); $^1$H NMR (DMSO-d6), δ8.44 and δ8.16 (s, 1H), δ7.46 (m, 1H), δ7.31 (s, 5H), δ4.99 (s, 2H), δ4.04(m, 1H), δ2.28 (d, 2H), δ1.80–0.95 (m, 10H), δ0.92–0.71 (m, 9H): MS: M+H= 386.2;

[1-S-(1-Cyano-3-methyl-cyclohexylcarbamoyl)-3-methyl-butyl[-carbamic acid benzyl ester (Compound 325); $^1$H NMR (DMSO-d6), δ8.44 (s, 1H), δ7.44 (d, 1H), δ7.31 (s, br, 5H), δ4.99 (s, 2H), δ4.02(m, 1H), δ2.28 (d, 2H), δ1.78–0.95 (m, 10H), δ0.92–0.71 (m, 9H): MS:M+H$^+$= 386.0;

2-(4-Morpholin-4-yl-benzoylamino)-bicyclo[2.2.1] heptane-2-carboxylic acid cyanomethyl-amide (Compound 326);

[1-S-(4-Cyano-1,1-dioxo-hexahydro-1]$^6$-thiopyran-4-ylcarbamoyl)-3-methyl-butyl]-carbamic acid benzyl ester (Compound 327); $^1$H NMR (DMSO-d6), δ8.69 (s, 1H), δ7.58 (d, 1H), δ7.31 (s, br, 5H), δ4.99 (s, 2H), δ4.02(m, 1H), δ3.21 (s, br, 4H), δ2.69–2.35 (m, 4H), δ1.69–1.17 (m, 3H), δ0.85 (m, 6H); MS: M+H$^+$=421.8;

4-{4-[1-(Cyanomethyl-carbamoyl)-cyclohexylcarbamoyl]-benzenesulfonyl}-piperazine-1-carboxylic acid tert-butyl ester (Compound 328);

{1-S-(4-Cyano-tetrahydro-pyran-4-ylcarbamoyl)-3-methyl-butyl]carbamic acid benzyl ester (Compound 329); and

[1-(4-Cyano-1-methyl-piperidin-4-ylcarbamoyl)-3-methyl-butyl]-carbamic acid benzyl ester (Compound 330).

Reference 7

4-(2-Pyrid-3-ylaminothiazol-4-yl)benzoic acid

A solution of 4-bromoacetylbenzoic acid (2.2 g, 10 mmol) in ethanol (50 mL) was treated with pyrid-3-ylthiourea (1.53 g, 1 mmol) and the mixture was refluxed for 3 hr. Solids were collected by filteration, washed with ether and dried to provide 4-(2-pyrid-3-ylaminothiazol-4-yl)benzoic acid (2.2 g, 74% yield). LC-MS: FAB LC-MS. 298.2 (M+H$^+$).

Proceeding as in Reference 7 provided 4-[2-(4-methylpiperazin-1-yl)thiazol-4-yl]benzoic acid LC-MS: FAB LC-MS 304.2 (M+H$^+$).

Reference 8 tert-Butyl 4-methyl-2S-[4-(2-pyrid-3-ylamino) thiazol-4-yl]benzoylaminopentanoate A mixture of 4-(2-pyrid-3-ylaminothiazol4-yl)benzoic acid (10 gm, 33.6 mmol), provided as in Reference 7, tert-butyl 2S-amino4-methylpentanoate (7.5 gm, 33.3 mmol), HBTU (13.3 gm, 33.3 mmol) and triethylamine (10.0 mL, 67.0 mmol) was stirred for approximately 12 hours and then diluted with sodium bicarbonate (50 mL) and ethyl acetate (300 mnL). The organic layer was separated, sequentially washed with water and brine, dried over anhydrous magnesium sulfate and concentrated under reduced pressure. The residue was dissolved in ethylacetate and hexane and product was recrystallized to provide tert-butyl 4-methyl-2S-[4-(2-pyrid-3-ylamino)thiazol-4-yl]benzoylaminopentanoate (10 gm, 62% yield). LC-MS: 467.1 M+H$^+$.

Reference 9

1-Amino-N-cyanomethylcyclohexanecarboxamide methanesulfonic acid salt

1-Benzyloxycarbonylaminocyclohexanecarboxylic acid (5.0 gm, 21.0 mmol) was taken up in DMF (40 mL). The mixture was cooled in an ice bath and then sequentially treated with aminoacetonitrile hydrochloride (3.8 gm, 42 mmol), HATU (8.25 gm, 21 mmol) and triethylamine (8.0 mL, 63 mmol). The reaction was allowed to proceed for 4 hours and then the mixture was concentrated under vacuum. The residue was treated with saturated NaHCO$_3$ solution (40 mL) and ethyl acetate (150 mL). The organic layer was separated, sequentially washed with water, 1 M hydrochloric acid (20 mL), water and brine and dried over anhydrous MgSO$_4$ and concentrated under reduced pressure. The free base of the product was purified from the residue using a plug of silica with ethyl acetate as an eluant. The free base of the product was taken up in dichlormethane (20 ml) and methanesulfonic acid (3.0 eq) and the mixture stirred for approximately 12 hours. The mixture was concentrated and the residue was triturated with ether (100 ml) and dried under vacuum to provide 1-amino-N-cyanomethylcyclohexanecarboxamide methanesulfonic acid salt (5.5 gm, 100% yield). LC-MS: 182.2, M+H$^+$.

Reference 10

4-[2-(4-tert-butoxycarbonylpiperazin-1-yl)thiazol-4-ylmethoxy]benzoic acid

A solution of tert-butyl 4-thiocarbamoylpiperazine-1-carboxylate (650 mg, 2.65 mmol) and 1,3-dichloroacetone (672 mg, 5.3 mmol) in 1,2-dichloroethane was treated with sodium bicarbonate (22 mg, 2.65 mmol). The reaction mixture was stirred at 70° C. for 18 hours and then diluted with chloroform. The dilution was washed with water and brine, dried over sodium sulfate and concentrated. Product was purified from the residue on a silica gel column, using ethyl acetate/hexanes (3/7) as eluent, to provide tert-butyl 4-(4-chloromethylthiazol-2-yl)piperazine-1-carboxylate (830 mg, 100% yield). HNMR (dmso-d6): 6.92 (1H, s), 4.57 (2H, s), 3.40 (8H, m), 1.42 (9H, s).

A solution of tert-butyl 4-(4-chloromethylthiazol-2-yl)piperazine-1-carboxylate (820 mg, 2.58 mmol) and methyl 4-hydroxybenzoate (395 mg, 2.58 mmol) in DMF was treated with potassium carbonate (360 mg, 2.6 mmol). The mixture was stirred at 70° C. for approximately 12 hours and then concentrated under vacuum. The residue was partitioned between ethyl acetate and water and the or organic phase was separated, washed with brine, dried over sodium sulfate and concentrated. The residue was crystallized from a mixture of ethyl acetate/hexanes to provide tert-butyl 4-[4-(4-methoxycarbonyl-phenoxymethyl)thiazol-2-yl] piperazine-1-carboxylate (830 mg, 74% yield). HNMR (dmso-d6): HNMR (dmso-d6): 7.91 (2H, d), 7.13 (2H, d), 6.91 (1H, s), 5.00 (2H, s), 3.81 (3H, s), 3.41 (8H, m), 1.41 (9H, s).

A solution of tert-butyl 4-(4-(4-methoxycarbonylphenoxymethyl)thiazol-2-yl]piperazine-1-carboxylate (820 mg, 1.89 mmol) in methanol (30 mL) and THF (10 mL) was treated with a solution of sodium hydroxide (226 mg, 5.67 mmol) in water (10 mL). The mixture was stirred at 55 ° C. for 8 hours and then concentrated by evaporation. The aqueous solution was diluted with water (10 mL) and the dilution was acidified with dilute hydrochloric acid. A resulting solid was collected by filtration to provide 4-[2-(4-tert-butoxycarbonylpiperazin-1-yl)thiazol-4-ylmethoxy]benzoic acid (800 mg, 100% yield). HNMR (dmso-d6): 7.88 (2H, d), 7.09 (2H, d), 6.91 (1H, s), 4.99 (2H, s), 3.44 (8H, m), 1.41 (9H, s).

Proceeding as in Reference 10 provided 4-(4-morpholin-4-ylmethylthiazol-2-ylamino)benzoic acid.

Reference 11 tert-Butyl 4-[4-(4-methoxycarbonylpiperidin-1-ylmethyl)thiazol-2-yl]piperazine-1-carboxylate A solution of tert-butyl 4(4-chloromethylthiazol-2-yl) piperazine-1-carboxyate (860 mg, 2.7 mmol) and methyl piperidine-4-carboxylate (539 mg, 3 mmol) in DMF was treated with potassium carbonate (414 mg, 3 mmol). The mixture was stirred at 70° C. for 18 hours and then concentrated under vacuum. Product was purified from the residue by flash chromatography on silica gel to provide tert-butyl 4-[4-(4-methoxycarbonylpiperidin-1-ylmethyl)thiazol-2-yl] piperazine-1-carboxylate (575 mg, 50% yield). HNMR (dmso-d6): 6.58 (1H, s), 3.59 (2H, s), 3.42 (4H, m), 3.34 (4H, m), 3.32 (3H, s), 2.78 (2H, m), 2.28 (1H, m), 2.02 (2H, m), 1.77 (2H, m), 1.57 (2H, m), 1.41 (3H, s).

Proceeding as in Reference 11 provided the following compounds:

tert-butyl 4-[2-(4-methoxycarbonylphenylamino)thiazol-4-ylmethyl]piperazine-1-carboxylate;

HNMR (dmso-d6): 10.6 (1H, s), 7.90 (2H, d), 7.70 (2H, d), 6.78 (1H, s), 3.80 (3H, s), 3.51 (2H, s), 3.32 (4H, m), 2.42 (4H, m), 1.41 (9H, s); and tert-butyl 4-cyanomethyl-piperazine-1-carboxylate; HNMR (dmso-d6): 3.75 (2H, s), 3.34 (4H, t), 2.41 (4H, t), 1.40 (9H, s).

Reference 12

1-[2-(4-tert-Butoxycarbonylpiperazin-1-ylthiazol-4-ylmethyl]piperidine-4-carboxylic acid A solution of tert-butyl 4-[4-(4-methoxycarbonylpiperidin-1-ylmethyl)thiazol-2-yl] piperidine-1-carboxylate (560 mg, 1.31 mmol), provided as in Reference 11, in methanol (30 mL) was treated at room temperature with a solution of sodium hydroxide (79 mg, 1.97 mmol) in water (10 mL). The mixture was heated at 50° C. for 3 hours and concentrated to dryness to provide 1-[2-(4-tert-butoxycarbonylpiperazin-1yl)thiazol-4-ylmethyl]piperidine-4-carboxylic acid.

Proceeding as in Reference 12 provided the following compounds:

4-[2-(1-tert-butoxycarbonylpiperazin-1-yl)methylthiazol-4-ylamino]piperadinecarboxylic acid.

Reference 13 tert-Butyl 4-thiocarbamoylmethylpiperazine-1-carboxylate

A solution of tert-butyl 4-cyanomethylpiperazine-1-carboxylate (4.5 g, 0.020 mol) in a 3:1 mixture of triethylamine/pyridine (40 mL) at room temperature was bubbled with hydrogen sulfide for 30 minutes. The reaction mixture was stirred for 18 hours at room temperature and then concentrated under vacuum. The residue was treated with a mixture 1:4 mixture of ethyl acetate/hexane and the resulting solid was collected by filtration and washed with the ethyl acetate/hexane mixture to provide tert-butyl 4-thiocarbamoylmethyl-piperazine-1-carboxylate (3.93 g, 75%). HNMR (dmso-d6): 9.87 (1H, bs), 9.07 (1H, bs), 3.35 (4H, t), 2.34 (4H, t), 1.29 (9H, s); LC/MS: M+1: 259.6.

Reference 14

4-[2-(1-Ethoxycarbonylpiperidin-4-ylamino)thiazol-4-yl]benzoic acid

A solution of ethyl 4-aminopiperidine-1-carboxylate (4.3 g, 0.025 mol) in dry THF was cooled to 0° C. and then treated with triethylamine (3.83 mL, 27.5 mol) and thiophosgene (2.1 mL, 27.5 mmol). The mixture was stirred for 1.5 hours at room temperature, cooled at 0° C. and then treated with ammonium hydroxide solution (7.7 mL, 28% in water). The mixture was stirred for approximately 12 hours and then concentrated by evaporation. The residue was taken up into ethyl acetate and the mixture was treated with a saturated solution of $NaHCO_3$ and brine. The organic phase was separated, dried over sodium sulfate and then concentrated to dryness. The residue was taken up into diethyl ether and a resulting solid was collected by filtration and washed with diethyl ether to provide ethyl 4-thioureidopiperidine-1-carboxylate (4.18 g, 72% V). HNMR (dmso-d6): 7.57 (1H, d), 6.9 (1H, s), 4.05 (1H, bs), 4.02 (2H, q), 3.86 (2H, d), 2.89 (2H, bs), 1.82 (2H, bs), 1.20 (2H, m), 1.17 (3H, t).

A solution of ethyl 4-thioureidopiperidine-1-carboxylate (3.8 g, 0.0164 mol.) and 4-(2-bromoacetyl)benzoic acid (4 g, 0.0164 mmol) in THF (100 mL) was heated at 70° C. for 2 hours, cooled to room temperature and then diluted with diethyl ether. A resulting solid was collected by filtration and washed with diethyl ether to provide 4-[2-(1-ethoxycarbonylpiperidin-4-ylamino)thiazol-4-yl]benzoic acid (4.32 g, 70% yield) as an off white solid. HNMR (dmso-d6): 7.93 (4H, m), 7.27 (1H, s), 4.05 (2H, q), 3.82 (3H, m), 3.04 (2H, m), 2.02 (2H, m), 1.41 (2H, m), 1.18 (3H, t). LC/MS: M+1: 376.

Proceeding as in Reference 14 provided the following compounds:

methyl 3-(4-pyrid-4-ylthiazol-2-ylamino)benzoic acid; HNMR (dmso-d6): 11.00 (1H, s), 8.89 (2H, d), 8.46 (2H, d), 8.38 (1H,s), 7.99 (2H, AB system, d), 7.88 (2H, AB system, d), 3.83 (3H, s), 3.50 (1H, bs);

4-[2-(4-tert-butoxycarbonylpiperazin-1-yl)thiazol-4-yl] benzoic acid; HNMR (dmso-d6): 7.96 (4H, s), 7.50 (1H, s), 3.48 (8H, s), 1.42 (9H, s); and 4-[2-(4-tert-butoxycarbonylpiperazin-1-ylmethyl)thiazol-4-yl]benzoic acid; HNMR (dmso-d6): 8.47 (1H, s), 8.12 (2H, d), 8.03 (2H, d), 4.00 (2H, bs), 3.51 (4H, t), 3.08 (4H, bs), 1.41 (9H, s); LC/MS (M+1): 404.

Reference 15

4-[2-(1-tert-Butoxycarbonylpiperidin-4-ylamino) thiazol-4-yl]benzoic acid

A solution of 4-[2-(1-ethoxycarbonylpiperidin4ylamino) thiazol-4-yl]benzoic acid (1 g, 2.66 mmol), provided as in Reference 14, in 30% hydrobromic acid in acetic acid was heated in a sealed vessel at 60° C. for approximately 12 hours and then cooled to room temperature. A resulting solid was collected by filtration and washed with diethyl ether to provide 4-(2-piperidin-4-ylamninothiazol-4-yl)benzoic acid hydrobromide (660 mg, 64%). HNMR (dmso-d6): 7.94 (4H, s), 7.31 (1H, s), 4.50 (2H, bs), 3.92 (1H, bs), 3.28 (2H, m), 3.07 (2H, m), 2.15 (2H, m), 1.69 (2H, m). LC/MS: M+1: 304.

A solution of 4-(2-piperidin-4-ylaminothiazol-4-yl) benzoic acid hydrobromide (600 mg, 1.56 mmol) and sodium hydroxide (125 mg, 3.12 mmol) in THF/water (30 mL) was treated with bis(1,1-dimethylethyl) dicarbonate (375 mg, 1.71 mmol). The mixture was stirred for approximately 12 hours at room temperature and then concentrated on a rotavap. The residue was diluted with water and the mixture was acidified to pH 3 with dilute hydrochloric acid and extracted with ethyl acetate. The extract was washed with brine and dried over $Na_2(SO)_4$ to provide 4-[2-(1-tert-butoxycarbonylpiperidin-4-ylamino)thiazol-4-yl]benzoic acid (680 mg, 100% yield). HNMR (dmso-d6): 7.93 (4H, s), 7.73 (1H, d), 7.26 (1H, s), 3.84 (2H, m), 3.76 (1H, m), 2.97 (2H, m), 1.97 (2H, m), 1.46 (9H, s), 1.28 (2H, m).

Reference 16

3-(4-Pyrid-4-ylthiazol-2-ylamino)benzoic acid

A solution of methyl 3-(4-pyrid-4-ylthiazol-2-ylamino) benzoate (500 mg, 1.27 mmol) in a 3/2 mixture of methanol/ THF (100 mL) was treated with an aqueous solution of sodium hydroxide ((240 mg, 6 mmol, 20 mL). The reaction mixture was stirred at 40° C. for approximately 12 hours and then concentrated. The residue was diluted with water (20 mL) and the diluted solution was acidified to pH 5 with dilute hydrochloric acid. A resulting solid was collected by filtration and washed with water to provide 3-(4-pyrid-4-ylthiazol-2-ylamino)benzoic acid (328 mg, 87% yield). HNMR (dmso-d6): 10.80 (1H, s), 8.63 (2H, m), 7.90 (7H, m). LC/MS: M+1: 297.86.

Example 7

N-(1S-Cyanomethyl-carbamoyl-2-methylbutyl)-4-(2-pyrid-3-ylthiazol-4-yl)benzamide (Compound 331)

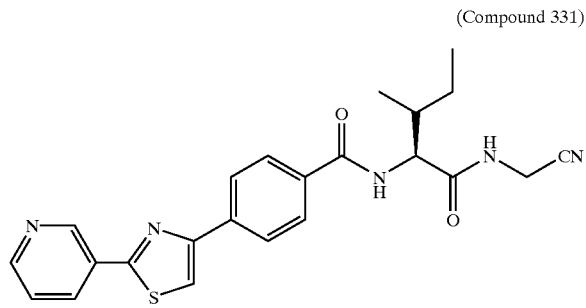

A solution of 4-(2-pyrid-3-ylthiazol-4-yl)benzoic acid (1.7 g, 6.03 mmol), N-cyanomethyl-2S-amino-3-methylpentanamide methanesulfonate (1.60 g, 6.03 mmol), and PyBOP (3.14 g, 6.03 mmol) in DMF (20 mL) was treated with 4-methylmorpholine (2.44 g, 24.14 mmol) and the mixture then was stirred at room temperature for 3 hours. The mixture was treated with 10% aqueous potassium carbonate (50 mL) and stirred for an additional 30 minutes, extracted with ethyl acetate (100 mL), washed with saturated aqueous $NaHCO_3$ (50 mL), dried over $MgSO_4$, filtered, evaporated, and filtered through a short plug of silica gel (50–100% ethyl acetate/dichloromethane). The most pure fractions were further purified by HPLC to provide N-(1S-cyanomethylcarbamoyl-2-methylbutyl)-4-(2-pyrid-3-ylthiazolyl)benzamide (89 mg, 13% yield).

Example 8

N-(1S-Cyanomethylcarbamoyl-3-methylbut-3-enyl)-4-(2-pyrid-3-ylthiazol-4-yl)benzamide (Compound 332)

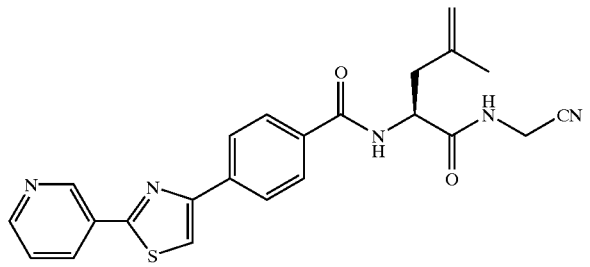

A solution of 4-(2-pyrid-3-ylthiazol-4-yl)benzoic acid (0.381 g, 1.35 mmol), N-cyanomethyl-2S-amino-4-methylpent-4-enamide methanesulfonate (0.355 g, 1.35 mmol) and HBTU (0.511 g, 1.35 mmol) in DMF (10 mL) was treated with 4-methylmorpholine (0.445 mL, 4.04 mmol) and the mixture was stirred at room temperature for approximately 12 hours. The solution was poured into a 4:1:2:3 mixture of ethyl acetate/THF/water/brine (100 mL) and the organic phase was separated, sequentially washed with saturated aqueous $NaHCO_3$ (50 mL) and brine (50 mL), dried over $MgSO_4$, filtered and evaporated to dryness. The residue was purified on a short plug of silica gel using ethyl acetate as the mobile phase to provide N-(1S-cyanomethylcarbamoyl-3-methylbut-3-enyl)-4-(2-pyrid-3-ylthiazol-4yl)benzamide (100 mg, 17% yield). MS (M+1): 432. NMR ($d^6$-DMSO): 1.74 (3H, s); 2.51–2.54 (2H, m*); 4.16 (2H, d, J=5.4 Hz); 4.71 (1H, m*); 4.79 (2H, d, J=9 Hz); 7.61 (1H, dd, J=8,5 Hz); 8.02(2H, d, J=7.7 Hz); 8.19 (2H, d, J=7.7 Hz); 8.46 (2H, s, d*); 8.65 (1H, d, J=7 Hz); 8.72 (1H, d, J=4.7 Hz); 8.79 (1H, t, J=5.4 Hz); 9.26 (1H, s).

Example 9

N-(1S-Cyanomethylcarbamoyl-3-methylbutyl)-4 (2-pyrid-3-ylaminothiazol-4-yl]benzamide (Compound 333)

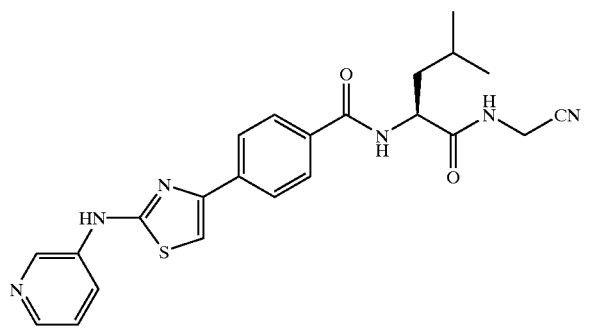

tert-Butyl 4-methyl-2S-[4-(2-pyrid-3-ylamino)thiazol-4-yl]benzoylaminopentanoate (10 gm, 20 mmol), provided as in Example 8, was taken up in HCl/dioxane (4.0 M, 50 mL, 200 mmol) and mixture was stirred overnight. The mixture was diluted with ether and solids were collected by filtration and then dried under vacuum to provide 4-methyl-2S-[4-(2-pyrid-3-ylamino)thiazol-4-yl]benzoylamninopentanoic acid hydrochloride (12 gm, 100% yield). LC-MS: 411.1, M+H.

4-Methyl-2S-[4-(2-pyrid-3-ylamino)thiazol-4-yl] benzoylaminopentanoic acid hydrochloride (5 gm, 10.1 mmol) was taken up in DMF (50 mL) and the resulting solution was treated sequentially with aminoacetonitrile hydrogen chloride (1.8 gm, 20 mmol), PyBop (5.2 gm, 10.1 mmol) and triethylamine (6 mL, 40 mmol). The mixture was stirred for approximately 12 hours and then diluted with sodium bicarbonate (30 mL) and ethyl acetate (200 mL). The organic layer was separated, sequentially washed with water and brine, dried over anhydrous magnesium sulfate and concentrated under reduced pressure. The residue was triturated with acetone and ether to provide N-(1S-cyanomethylcarbamoyl-3-methylbutyl)-4-(2-pyrid-3-ylaminothiazol-4-yl]benzamide (1.5 gm, 30% yield). $^1$H NMR (DMSO-$d_6$, ppm): ): 0.96 (m, 6 H), 1.75 (m, 3 H), 4.31 (m, 1 H), 4.47 (m, 2 H), 7.82–8.03 (m,5 H), 8.31 (m, 2 H), 8.53 (m, 1 H), 8.73 (d, 1 H), 8.91 (d, 1 H), 9.11 (m, 1 H), 11.01 (m, 1 H). ES-Ms: 449.3 (M+H$^+$).

Proceeding as in Example 9 provided the following compounds of Formula I:

N-(1S-cyanomethylcarbamoyl-3-methylbutyl)-4-(2-pyrid-3-ylthiazol-4-yl)benzamide (Compound 334); $^1$H NMR (DMSO-$d_6$, ppm): 0.91 (m, 6 H), 1.75 (m, 3 H), 4.11 (m, 2 H), 4.47 (m, 1 H), 7.51 (m, 1 H), 7.81 (m, 2 H), 8.03 (m, 2 H), 8.33 (d, 2 H), 8.91 (m, 3 H), 9.11 (m, 1 H); ES-Ms: 434.3 (M+H$^+$);

N-(1S-cyanomethylcarbamoyl-3-methylbutyl)-4-(2-pyrid-4-ylamino)thiazol-4-ylbenzamide (Compound 335); $^1$H NMR (DMSO-$d_6$, ppm): ): 0.91 (m, 6 H), 1.65 (m, 3 H), 4.01 (m, 2 H), 4.37 (m, 1 H), 7.82–8.03 (m, 7 H), 8.73 (m, 3 H), 8.91 (m, 1 H); ES-Ms: 448.9 (M+H$^+$);

N-(1S-cyanomethyl-carbamoyl-3-methylbutyl)-4-(2-pyrid-4-ylthiazol-4-yl)benzamide (Compound 336); $^1$H NMR (DMSO-$d_6$, ppm): 0.91 (m, 6 H), 1.55–72 (m, 3 H), 4.17 (m, 2 H), 4.31 (m, 1 H), 8.03–8.63 (m, 7 H), 8.83 (m, 2 H), 8.91 (m, 1 H), 8.98–9.11 (m, 2 H); ES-Ms: 443.9 (M+H$^+$);

N-(1S-cyanomethylcarbamoyl-3-methylbutyl)-4-(2-pyrid-2-ylamino)thiazol-4-ylbenzamide (Compound 337); $^1$H NMR (DMSO-$d_6$, ppm): 0.91 (m, 6 H), 1.65 (m, 3 H), 4.01 (m, 2 H), 4.37 (m, 1 H), 6.91–7.11 (m, 2 H), 7.60 (m, 1 H), 7.11 (m, 1 H), 7.59 (d, 1 H), 7.72 (d, 1 H), 8.03 (m, 4 H), 8.32 (m, 1 H), 8.59 (m, 1 H), 8.73 (m, 1 H); ES-Ms: 448.9 (M+H$^+$);

N-{4-[4-(1S-cyanomethylcarbamoyl-3-methylbutylcarbamoyl)phenyl]thiazol-2-yl}isonicotinamide (Compound 338); $^1$H NMR (DMSO-$d_6$, ppm): 0.95 (m, 6 H), 1.65–1.78 (m, 3 H), 4.17 (m, 3 H), 8.01–8.15 (m, 5 H), 8.60–8.79 (m, 4 H); ES-Ms: 477.2 (M+H$^+$);

N-(1S-cyanomethylcarbamoyl-3-methylbutyl)-4-[4-(2-morpholin-4-ylethyl)piperazin-1-yl]benzamide (Compound 339); $^1$H NMR (DMSO-$d_6$, ppm): 0.95 (m, 6 H), 1.65–1.78 (m, 3 H), 3.11–3.67 (m, 16 H), 3.78–3.85 (m, 4 H), 4.17 (s, 2 H), 4.45 (m, 1 H), 7.01 (d, 2 H), 8.01 (d, 2 H), 8.40 (m, 1 H), 8.79 (m, 1 H); ES-Ms: 471.2 (M+H$^+$);

N-(1S-cyanomethylcarbamoyl-3-methylbutyl)-4-(4-pyrid-4-ylpiperazin-1-yl)benzamide (Compound 340); $^1$H NMR (DMSO-$d_6$, ppm): 0.95 (m, 6 H), 1.65–1.78 (m, 3 H), 3.67–3.87 (m, 8 H), 4.17 (s, 2 H), 4.38 (m, 1 H), 6.81 (d, 2 H), 7.21 (d, 2 H), 7.78 (d, 2 H), 8.20 (d, 2 H), 8.79 (m, 1 H); ES-Ms: 435.2 (M+H$^+$);

N-[1S-(1-cyanocyclopropylcarbamoyl)-3-methylbutyl]-4-[2-(4-methylpiperazin-1-yl)thiazol-4-yl]benzamide (Compound 341); $^1$H NMR (DMSO-$d_6$, ppm): 0.91 (m, 6 H), 1.55–1.72 (m, 3 H), 2.81 (s, 3 H), 3.21–3.87 (m, 8 H), 4.17 (m, 2 H), 4.31 (m, 1 H), 7.51 (s, 1 H), 8.03 (m, 4 H), 8.83 (m, 2 H), 8.61 (m, 1 H), 9.11 (m, 1 H); ES-Ms: 480.9 (M+H$^+$); and N-(1R-cyanomethylcarbamoyl-3-methylbutyl)-4-(2-morpholin-4-ylthiazol-4-yl)benzamide (Compound 342); $^1$H NMR (DMSO-$d_6$, ppm): 0.91 (m, 6 H), 1.55–1.72 (m, 3 H), 3.15–3.27 (m, 4 H), 3.61–3.87 (m, 4 H), 4.17 (m, 2 H), 4.51 (m, 1 H), 7.51 (s, 1 H), 7.72 (m, 1 H), 8.03 (m, 4 H), 8.61 (m, 1 H), 8.81 (m, 1 H); ES-Ms: 441.2 (M+H$^+$).

Example 10

N-(1-Cyanomethylcarbamoylcyclohexyl)-4-[2-(4-methylpiperazin-1-yl)thiazol-4-yl]benzamide Trifluoroacetic Acid Salt (Compound 343)

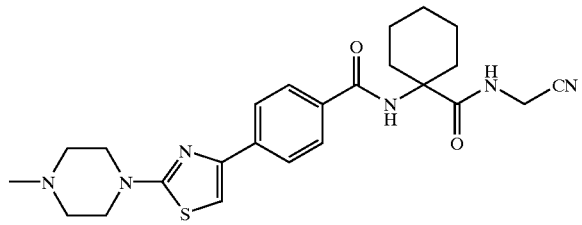

A solution of 4-[2-(4-methylpiperazin-1-yl)thiazol-4-yl] benzoic acid (330 mg, 1 mmol), provided as in Reference 7, in DMF (10 mL) was sequentially treated with trifluoroacetic acid, 1-amino-N-cyanomethylcyclohexanecarboxamide methanesulfonic acid salt (300 mg, 1.0 mmol), provided as in Reference 9, triethylamine (0.5 mL, 3 mmol) and HATU (400 mg, 1 mmol). The solution was stirred for approximately 12 hours and then diluted with ethyl acetate (50 mL) and saturated sodium bicarbonate (20 mL). The ethyl acetate layer was separated and concentrated. Product was purified from the residue by preparative reverse phase HPLC to provide N-(1-cyanomethylcarbamoylcyclohexyl)-4-[2-(4-methylpiperazin-1-yl)thiazol-4-yl]benzamide trifluoroacetic acid salt (200 mg, 40%). $^1$H NMR (DMSO-$d_6$, ppm):): 1.55–1.72 (m, 6 H), 2.11–2.23 (m, 2 H), 2.81 (s, 3 H), 3.21–3.67 (m, 6 H), 4.89–4.13 (m, 5 H), 7.51 (s, 1 H), 8.03 (m, 4 H), 8.13 (m, 1 H). ES-Ms: 466.4 (M+H$^+$).

Proceeding as in Example 10 provided the following compounds of Formula I:

N-[1-(4-cyanotetrahydropyran-4-ylcarbamoyl)cyclohexyl]-4-[2-(4-methylpiperazin-1-yl)thiazol-4-yl]benzamide (Compound 344); $^1$H NMR (DMSO-$d_6$, ppm): 1.25–1.42 (m, 4 H), 1.55–1.91 (m, 6 H), 2.81 (s, 3 H), 3.11–3.87 (m, 10 H), 4.17–4.23 (m, 2 H), 7.51 (s, 1 H), 7.88 (m, 5 H); ES-Ms: 537.1 (M+H$^+$); and N-(1-cyanomethylcarbamoylcyclohexyl)-4-(2-morpholin-4-ylthiazol-4-yl)benzamide (Compound 345); $^1$H NMR (DMSO-$d_6$, ppm): 1.51–1.74 (m, 6 H), 2.11–2.23 (m, 4 H), 3.21–3.67 (m, 8 H), 4.17–4.23 (m, 2 H), 7.51 (s, 1 H), 8.03 (m, 4 H), 8.13 (m, 1 H); ES-Ms: 454.0 (M+H$^+$).

Example 11

N-(1S-Cyanomethylcarbamoyl-3-methylbutyl)-4-[2-(1-methylpyrid-3-yl)thiazol-4-yl]benzamide Iodide Salt (Compound 346)

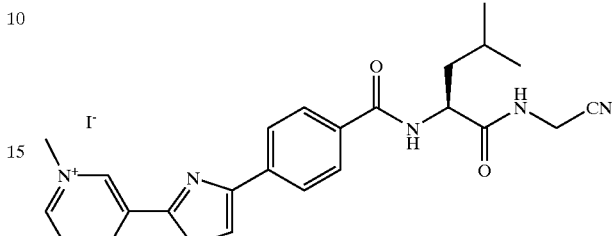

A solution of N-(1S-cyanomethylcarbamoyl-3-methylbutyl)-4-(2-pyrid-3-ylthiazol-4-yl)benzamide (80 mg, 0.184 mmol), provided as in Reference 12, in acetonitrile (1 mL) was treated with methyl iodide (115 µL, 1.84 mmol, 10 eq.) added dropwise. The reaction mixture was stirred for approximately 72 hours and then concentrated to dryness. The residue treated with ethyl ether. The solid was collected by filtration and washed with the same diethyl ether to provide solvent N-(1S-cyanomethylcarbamoyl-3-methylbutyl)-4-[2-(1-methylpyrid-3-yl)thiazol-4-yl]benzamide iodide salt (85 mg, 80% yield). HNMR (dmso-d6): 9.74 (1H, s), 9.15 (1H, d), 9.07 (1H, d), 8.78 (1H, t), 8.68 (1H, d), 8.65 (1H, s), 8.24 (3H, m), 8.07 (2H, d), 4.58 (1H, m), 4.48 (3H, s), 4.15 (2H, d), 1.70 (3H, m), 0.91 (6H, m). M: 448).

Proceeding as in Example 11 provided the following compounds of Formula I:

4-[2-(1-carbamoylmethylpyridin-3-yl)thiazol-4-yl]-N-(1S-cyanomethylcarbamoyl-3-methylbutyl)benzamide bromide salt (Compound 347); HNMR (dmso-d6): 9.78 (1H, s), 9.21 (1H, d), 9.06 (1H, d), 8.78 (1H, t), 8.68 (1H, d), 8.66 (1H, s), 8.33 (1H, dd), 8.24 (2H, d), 8.08 (3H, m), 7.79 (1H, s), 5.55 (2H, s), 4.55 (1H, m), 4.15 (2H, d), 1.70 (3H, m), 0.91 (6H, m). M: 491); LC/MS, M: 491;

N-(1S-cyanomethylcarbamoyl-3-methylbutyl)-4-[2-(1-methylpyridin-4ylamino)thiazol-4-yl]benzamide iodide salt (Compound 348); HNMR (dmso-d6): 8.76 (1H, t), 8.63 (3H, m), 8.10 (3H, m), 8.03 (2H, d), 7.97 (1H, s), 4.57 (1H, m), 4.15 (2H, d), 4.14 (3H, s), 1.70 (3H, m), 0.91 (6H, m);

N-(1S-cyanomethylcarbamoyl-3-methylbutyl)-4-[2-(1-methylpyridin-4-yl)thiazol-4-yl]benzamide iodide salt (Compound 349); HNMR (dmso-d6): 9.09 (2H, d), 8.83 (1H, s), 8.73 (2H, d), 8.25 (2H, d), 8.08 (2H, d), 4.58 (1H, m), 4.52 (3H, s), 4.16 (2H, s), 1.70 (3H, m), 0.92 (6H, m); and N-(1S-cyanomethylcarbamoyl-3-methylbutyl)-4-[2-(1-allylpyrid-4-yl)thiazol-4-yl]benzamide bromide salt (Compound 350).

Example 12

Ethyl 4-{4-[4-(1S-cyanomethylcarbamoyl-3-methylbutylcarbamoyl)phenyl]thiazol-2-ylamino}piperidine-1-carboxylate (Compound 351)

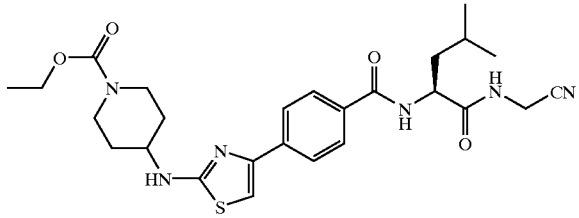

A solution of 4-[2-(1-tert-butoxycarbonylpiperidin-4-ylamino)thiazol-4-yl]benzoic acid (751 mg, 2 mmol), provided as in Reference 15, and methane sulfonate salt of 2S-amino-N-cyanomethyl-4-methylpentanamide (560 mg, 2 mmol) in DMF (10 mL) was treated with PyBOP (1.04 mg, 2 mmol) and diisopropylethylamine (715 µL, 4.1 mmol) at room temperature. The mixture was stirred overnight and then concentrated under vacuum. The residue was dissolved in ethyl acetate and the solution was washed sequentially with saturated NaHCO$_3$ solution and brine, dried on sodium sulfate and concentrated. Product was purified from the residue by silica gel column, using ethyl acetate/hexanes as eluent, to provide ethyl 4-{4-[4-(1S-cyanomethylcarbamoyl-3-methylbutylcarbamoyl)phenyl]thiazol-2-ylamino}piperidine-1-carboxylate (815 mg, 77% yield). HNMR (dmso-d6): 8.71 (1H, t), 8.54 (1H, d), 7.91 (4H, AB system, dd), 7.74 (1H, d), 7.23 (1H, s), 4.52 (1H, m), 4.13 (2H, t), 4.04 (2H, q), 3.90 (2H, m), 3.76 (1H, m), 3.04 (2H, m), 1.98 (2H, m), 1.65 (3H, m), 1.38 (2H, m), 1.18 (3H, t), 0.89 (6H, m). LC/MS: M+1: 527.

Proceeding as in Example 12 provided ethyl 4-{4-[4-(1S-cyanomethylcarbamoyl-3-methylbutylcarbamoyl)phenyl]thiazol-2-ylamino}piperidine-1-carboxylate (Compound 252); HNMR (dmso-d6): 8.71 (1H, t), 8.54 (1H, d), 7.91 (4H, dd), 7.73 (1H, d), 7.23 (1H, s), 4.52 (1H, m), 4.13 (2H, m), 3.85 (2H, m), 3.75 (1H, m), 3.00 (2H, m), 1.95 (2H, m), 1.70 (3H, m), 1.40 (9H, s), 1.37 (2H, m), 0.88 (6H, m); LC/MS: M+1: 555;

N-(1S-cyanomethylcarbamoyl-3-methylbutyl)-4-(4-pyrid-4-ylthiazol-2-ylamino)benzamide (Compound 353); HNMR (dmso-d6): 10.6 (1H, s), 8.67 (1H, t), 8.63 (2H, AB system, d), 8.38 (1H, d), 7.95 (2H, AB system, d), 7.88 (2H, AB system, d), 7.82 (2H, AB system), d), 7.81 (1H, s), 4.49 (1H, m), 4.13 (2H, d), 1.70 (3H, m), 0.89 (6H, m); LC-MS: M+1: 449;

tert-butyl 4-{4-[4-(1S-cyanomethylcarbamoyl-3-methylbutylcarbamoyl)phenyl]thiazol-2-yl}piperazine-1-carboxylate (Compound 354); HNMR (dmso-d6): 8.72 (1H, t), 8.57 (1H, d), 7.94 (4H, s), 7.48 (1H, s), 4.52 (1H, m), 4.13 (2H, d), 3.48 (8H, s), 1.65 (3H, m), 0.89 (6H, m). LC/MS: M+1: 541;

tert-butyl 4-{4-[4-(1S-cyanomethylcarbamoyl-3-methylbutylcarbamoyl)phenoxymethyl]thiazol-2-yl}piperazine-1-carboxylate (Compound 355); HNMR (dmso-d6): 8.66 (1H, t), 8.40 (1H, d), 7.89 (2H, d), 7.08 (2H, d), 6.90 (1H, s), 4.99 (2H, s), 4.48 (1H, m), 4.11 (2H, d), 3.41 (8H, m), 1.65 (3H, m), 0.88 (6H, m);

tert-butyl 4-{4-[4-(1S-cyanomethylcarbamoyl-3-methylbutylcarbamoyl)piperidin-1-ylmethyl]thiazol-2-yl}piperazine-1-carboxylate (Compound 356); HNMR (dmso-d6): 8.71 (1H, t), 8.17 (1H, d), 7.03 (1H, s), 4.26 (1H, m), 4.16 (2H, bs), 4.11 (2H, d), 3.79 (4H, bs), 3.45 (4H, bs), 2.97 (2H, bs), 2.43 (1H, m), 1.85 (3H, m), 1.46 (3H, m), 1.41 (9H, s); LC/MS: M+1: 562.4;

N-(1S-cyanomethylcarbamoyl-3-methylbutyl]-4-(4-morpholin-4-ylmethylthiazol-2-ylamino)benzamide (Compound 357); HNMR (dmso-d6): 10.7 (1H, s), 8.72 (1H, t), 8.39 (1H, d), 7.91 (2H, d), 7.71 (2H, d), 7.19 (1H, s), 4.50 (1H, m), 4.34 (2H, s), 4.12 (2H, m), 3.59 (8H, m), 165 (3H, m), 0.89 (6H, m); LC/MS: M+1: 471;

tert-butyl 4-{2-[4-(1S-cyanomethylcarbamoyl-3-methylbutylcarbamoyl}phenylamino]thiazol-4-ylmethyl}piperazine-1-carboxylate (Compound 358);

tert-butyl 4-(4-{4-[1S-(1-cyanocyclopropylcarbamoyl)-3-methylbutylcarbamoyl]phenyl}thiazol-2-yl)piperazine-1-carboxylate (Compound 359); HNMR (dmso-d6): 8.98 (1H, s), 8.51 (1H, d), 7.92 (4H, m), 7.47 (1H, s), 4.44 (1H, m), 3.48 (8H, s), 1.65 (2H, m), 1.48 (3H, m), 1.43 (9H, s), 1.12 (2H, m), 0.89 (6H, m); LC/MS: M+1: 567.5;

tert-butyl 4-(4-{4-[1S-(N-cyanomethyl-N-methylcarbamoyl)-3-methylbutylcarbamoyl]phenyl}thiazol-2-yl)piperazine-1-carboxylate (Compound 360); HNMR (dmso-d6): 8.70 (1H, d), 7.92 (4H, s), 7.47 (1H, s), 4.93 (1H, m), 4.41 (2H, m), 3.48 (8H, s), 3.20 and 2.91 (3H, s), 1.75 (2H, m), 1.42 (1H, m), 1.42 (9H, s), 0.93 (6H, bs); LC/MS: M+1: 555.5;

N-[1S-(N-cyanomethyl-N-methylcarbamoyl)-3-methylbutyl]-4-[2-(4-methylpiperazin-1-yl)thiazol-4-yl]benzamide (Compound 361); HNMR (dmso-d6):

8.71 (1H, d), 7.98 and 7.95 (4H, m), 7.60 and 7.58 (1H, s), 4.93 (1H, m), 4.42 (2H, m), 4.12 (2H, m), 3.53 (6H, m), 2.87 (3H, s),1.74 (2H, m), 1.45 (1H, m), 0.93 (6H, m); LC/MS: M+1: 468.4; and tert-butyl 4-(4-{4-[1S-(1-cyanocyclopropylcarbamoyl)-3-methylbutylcarbamoyl]phenyl}thiazol-2-ylmethyl)piperazine-1-carboxylate (Compound 362); HNMR (dmso-d6): 8.22 (1H, s), 8.00 (5H, m), 4.45 (1H, m), 3.92 (2H, s), 3.36 (4H, m), 2.50 (4H, m,),), 1.65 (2H, m), 1.48 (3H, m), 1.40 (9H, s), 1.12 (2H, m), 0.89 (6H, m).

Example 13 tert-Butyl 4-{4-[4-(1-cyanomethylcarbamoylcyclohexylcarbamoyl)phenyl]thiazol-2-yl}piperazine-1carboxylate (Compound 363)

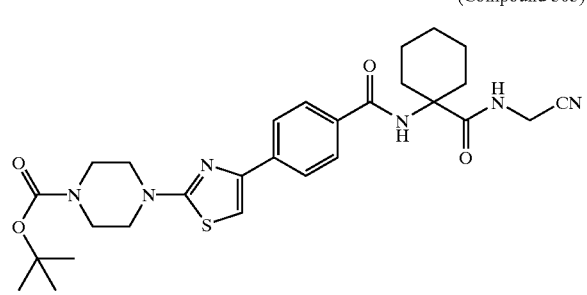

A solution of 1-amino-N-cyanomethylcyclohexanecarboxamide (500 mg, 1.8 mmol), provided as in Reference 9, and 4-[2-(4-tert-butoxycarbonylpiperazin-1-yl)thiazol-4-yl]benzoic acid (702 mg, 1 mmol), provided as in Reference 14, in DMF was treated with diisopropylethylamine (940 μL, 5.4 mmol) and HATU (685 mg, 1.8 mmol). The mixture was stirred for approximately 12 hours at room temperature and then concentrated under vacuum. The residue was dissolved in ethyl acetate and the solution was washed sequentially with saturated solution of $NaHCO_3$, water and brine, dried over $Na_2SO_4$ and concentrated. Product was purified from the residue through silica gel to provide tert-butyl 4-{4-[4-(1-cyanomethylcarbamoylcyclohexylcarbamoyl)phenyl] thiazol-2-yl}piperazine-1-carboxylate (350 mg, 35% yield) as a foam. HNMR (dmso-d6): 8.31 (1H, t), 8.09 (1H, s), 8.02 (4H, dd), 7.57 (1H, s), 4.15 (2H, d), 3.58 (8H, s), 2.13 (2H, m), 1.76 (2H, m), 1.53 (4H, m), 1.43 (9H, s), 1.40 (2H, m). LC/MS: M+1: 553.

Proceeding as in Example 13 provided tert-butyl 4-(4-{4-[1-cyanomethylcarbamoyl)cyclohexylcarbamoyl] phenyl}thiazol-2-ylmethyl)piperazin e-1-carboxylate (Compound 364); HNMR (dmso-d6): 8.22 (1H, m), 8.00 (4H, m), 7.47 (1H, d), 4.04 (2H, m), 3.92 (2H, s), 3.37 (4H, m), 2.50 (4H, m), 2.13 2H, m), 1.75 (2H, m), 1.54 (5H, m), 1.40 (9H, s), 1.40 (2H, m); LC/MS: M+1: 567.4.

Example 14

N-(1S-Cyanomethylcarbamoyl-3-methylbutyl)-4-(2-piperidin-4-ylaminothiazol-4-yl)benzamide Methanesulfonic Acid Salt (Compound 365)

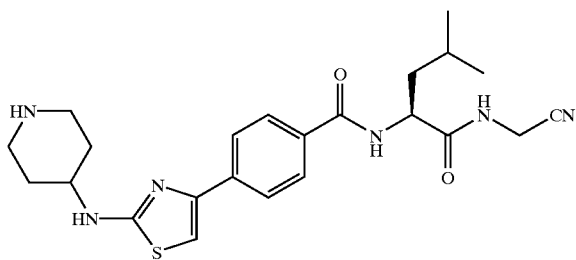

A solution of ethyl 4-{4-[4-(1S-cyanomethylcarbamoyl-3-methylbutylcarbamoyl)phenyl]thiazol-2-ylamino}piperidine-1-carboxylate (290 mg, 0.52 mmol), prepared as in Example 12, in dry THF (5 mL) was treated with methanesulfonic acid (135 μL, 2.08 mmol, 4 eq) at room temperature. The mixture was stirred overnight and then diluted with diethyl ether. The resulting solid was collected by filtration and triturated with several portions of diethyl ether. Product was purified from the crude solid by reversed phase preparative TLC, using a mixture of acetonitrile/water (8/2) as the mobile phase, to provide N-(1S-cyanomethylcarbamoyl-3-methylbutyl)-4-(2-piperidin-4-ylaminothiazol-4-yl)benzamide methanesulfonic acid salt (90 mg, 31% yield). HNMR (dmso-d6): 8.73 (1H, t), 8.54 (1H, d), 7.92 (4H, s), 7.85 (1H, d), 7.27 (1H, s), 4.51 (1H, m), 4.13 (2H, t), 3.88 (1H, m), 3.25 (2H, m), 3.03 (2H, m), 2.30 (3H, s), 2.15 (2,H m), 1.65 (5H, m), 0.89 (6H, m). LC/MS: M+1: 455.

Proceeding as in Example 14 provided the following compounds of Formula I:

N-(1S-cyanomethylcarbamoyl-3-methylbutyl)-4-(2-piperazin-1-ylthiazol-4-yl)benzamide (Compound 366); HNMR (dmso-d6): 8.96 (1H, bs), 8.74 (1H, t), 8.58 (1H, d), 7.95 (4H, s), 7.56 (1H, s), 4.52 (1H, m), 4.13 (2H, d), 3.71 (4H, m), 3.28 (4H, bs), 1.65 (3H, m), 0.89 (6H, m);

N-(1S-cyanomethylcarbamoyl-3-methylbutyl)-4-(2-piperazin-1-ylthiazol-4-ylmethoxy)benzamide (Compound 367); HNMR (dmso-d6): 8.67 (1H, t), 8.40 (1H, d), 7.89 (2H, d), 7.07 (2H, d), 6.99 (1H, s), 4.99 (1H, s), 4.48 (1H, m), 4.11 (2H, d), 3.56 (4H, m), 3.18 (4H, m), 1.65 (3H, m), 0.89 (6H, m); LC/MS: M+1: 471;

N-(1S-cyanomethylcarbamoyl-3-methylbutyl)-1-(2-piperazin-1-ylthiazol-4-ylmethyl)piperidine-4-carboxamide (Compound 368); HNMR (dmso-d6): 9.10 (1H, bs), 8.67 (1H, t), 8.15 (1H, s), 7.09 (1H, s), 4.25 (1H, m), 4.10 (2H, d), 3.63 (2H, bs), 3.35 (4H, bs), 3.24 (4H, m), 2.92 (2H, bs), 2.36 (7H, m)), 1.80 (3H, m), 1.44 (3H, m), 0.83 (6H, m); LC/MS: M+1: 462.3;

N-(1S-cyanomethylcarbamoyl-3-methylbutyl)-4-(4piperazin-1-ylmethylthiazol-2-ylamino)benzamide (Compound 369); HNMR (dmso-d6): 10.4 (1H, s), 8.68 (1H, t), 8.48 (1H, bs), 8.35 (1H, d), 7.88 (2H, d), 7.67 (2H, d), 4.48 (1H, m), 4.12 (2H, d), 3.58 (2H, s), 3.10 (4H, bs), 2.69 (4H, bs), 2.34 (6H, s), 1.65 (3H, m), 0.88 (6H, m);

N-[1S-(1-cyanocyclopropylcarbamoyl)-3-methylbutyl]-4-(2-piperazin-1-yl-thiazol-4-yl)benzamide (Compound 370); HNMR (dmso-d6): 8.99 (1H, s), 8.52 (1H, d), 7.94 (4H, s), 7.53 (1H, s), 4.44 (1H, m), 3.65 (4H, m), 3.20 (4H, m), 1.65 (2H, m), 1.47 (3H, m), 1.11 (2H, m), 0.88 (6H, m); LC/MS: M+1: 467.2;

N!-[1S-(N-cyanomethyl-N-methylcarbamoyl)-3-methylbutyl]-4-(2-piperazin-1-ylthiazol-4-yl)benzamide (Compound 371); HNMR (dmso-d6): 8.69 (1H, d), 7.94 (4H, m), 7.53 (1H, s), 4.93 (1H, m), 4.41 (2H, dd), 3.66 (4H, m), 3.30 (4H, m), 3.20 and 2.90 (3H, s), 1.70 (2H, m), 1.45 (1H, m), 0.93 (6H, m); LC/MS: M+1: 455.1;

N-(1-cyanomethylcarbamoylcyclohexyl)-4-(2-piperazin-1-ylthiazol-4-yl)benzamide (Compound 372); HNMR (dmso-d6): 8.90 (1H, bs), 8.21 (1H, m), 7.94 (5H, m), 7.56 (1H, d), 4.06 (2H, d), 3.71 (4H, m), 3.29 (4H, bs), 2.13 (2H, m), 1.76 (2H, m), 1.54 (5H, m), 1.29 (1H, m). LC/MS: M+1: 453.2; and N-(1-cyanomethylcarbamoylcyclohexyl)-4-(2-piperazin-1-ylmethylthiazol-4-yl)benzamide (Compound 373); HNMR (dmso-d6): 8.26 (1H,s), 8.24 (1H, d), 8.05 (1H, s), 4.06 (2H, d), 4.01 (2H, s), 3.15 (4H, m), 2.77 (4H, m), 2.15 (2H, m), 1.75 (2H, m), 1.54 (5H, m), 1.30 (1H, m). LC/MS: M+1: 467.2.

Example 15

Ethyl 4-{4-[4-(1S-cyanomethylcarbamoyl-3-methylbutylcarbamoyl)phenyl]thiazol-2-yl}piperazine-1-carboxylate (Compound 374)

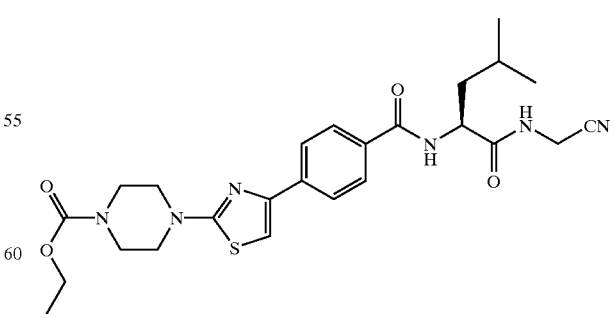

A solution of N-(1S-cyanomethylcarbamoyl-3-methylbutyl)-4-(2-piperazin-1-ylthiazol-4-yl)benzamide (200 mg, 0.35 mmol), provided as in Example 14, in a 5:1 mixture of dry TFF/DMF was treated with diisopropylethylamine (146 μL, 0.84 mmol) and ethyl chloro formate (40 mL, 0.42 mmol). The mixture was stirred for 16 hours at room temperature and then diluted with ethyl acetate. The dilution was acidified with 1 N hydrochloric acid, washed with brine, dried over sodium sulfate and concentrated. Crude product was purified from the residue by preparative TLC to provide ethyl 4-{4-[4-(1S-cyanomethylcarbamoyl-3-methylbutylcarbamoyl)phenyl]thiazol-2-yl}piperazine-1-carboxylate. HNMR (dmso-d6): 8.73 (1H, t), 8.57 (1H, d), 7.94 (4H, s), 7.48 (1H, s), 4.53 (1H, m), 4.13 (2H, d), 4.08 (2H, q), 3.52 (8H, m), 1.65 (3H, m), 1.21 (3H, t) 0.89 (6H, m).

Example 16

N-[4-(1S-cyanomethylcarbamoyl-3-methylbutylcarbamoyl)phenyl]-4-benzylpiperazine-1-carboxamide Trifluoroacetic Acid Salt (Compound 383)

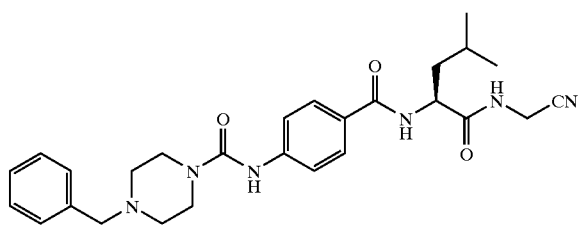

A solution of 4-amino-N-(1S-cyanomethylcarbamoyl-3-methylbutyl)benzamide (1.7 g, 6 mmol) in dichloromethane (120 mL) and acetonitrile (60 mL) was warmed and treated with aqueous sodium bicarbonate solution (100 mL). The mixture was cooled to 0° C. with vigorous stirring and then allowed to settle into two layers briefly. The bottom layer was treated at once with a 20% phosgene solution in toluene (10 mL, 18 mmol). The mixture was stirred vigorously for 10 minutes at 0° C. One twelfth of the mixture was added to a solution of 1-benzylpiperazine (0.17 mL, 10 mmol) in acetonitrile (5 mL) and after stirred for 20 h, the mixture was extracted with dichloromethane. The extract was dried over anhydrous sodium sulfate, filtered, and evaporated. The crude product was purified by reverse phase HPLC on a C-18 column to provide N-[4-(1S-cyanomethylcarbamoyl-3-methylbutylcarbamoyl)phenyl]-4-benzylpiperazine-1-carboxamide trifluoroacetic acid salt (as a white solid (0.14 g, 46% yield). $^1$H NMR (270 MHz, DMSO-$d_6$) δ0.84 (d, 3), 0.88 (d, 3), 1.47–1.75 (m, 3), 3.1–3.4 (m, 6), 4.10 (t, 2), 4.2–4.3 (m, 2), 4.35 (br. s, 2), 4.48 (m, 1), 7.48 (br. s, 5), 7.52 (d, 2), 7.82 (d, 2), 8.36 (d, 1 NH), 8.68 (t, 1 NH), 9.01 (s, 1 NH), 10.1 (br. s, 1); ESI-MS m/z 491.4 (M+1).

Proceeding as in Example 16 provided the following compounds of Formula I:

3-[3-(1-benzylpyrrolidin-3-yl)-3-methylureido]-N-(1S-cyanomethylcarbamoyl)-3-methylbutyl)benzamide (Compound 375); $^1$H NMR (270 MHz, DMSO-$d_6$, mixture of diastereomers) δ0.86 (d, 3), 0.90 (d, 3), 1.47–1.77 (m, 3), 2.0–2.4 (m, 2), 2.95 and 2.97 (s, 3), 3.1–3.7 (m, 4), 4.12 (d, 2), 4.25–4.53 (m, 3), 4.7–4.9 (m, 1), 7.30–7.37 (m, 1), 7.45–7.53 (m, 6), 7.91 (s, 1), 8.47 (d, 1), 8.59 (s, 1), 8.72 (m, 1); ESI-MS m/z 505.2 (M+1);

N-[4-(1S-cyanomethylcarbamoyl-3-methylbutylcarbamoyl)phenyl]-4-(2-morpholin-4-ylethyl)piperazine-1-carboxamide (Compound 376); $^1$H NMR (270 MHz, DMSO-$d_6$) δ0.89 (d, 3), 0.91 (d, 3), 1.48–1.75 (m, 3), 2.9–3.2 (m, 12), 3.6–3.8 (m, 8), 4.12 (d, 2), 4.51 (m, 1), 7.34 (t, 1), 7.54 (d, 1), 7.68 (dd, 1), 7.89 (t, 1), 8.47 (d, 1 NH), 8.71 (t, 1 NH), 8.81 (s, 1 NH); ESI-MS m/z 514.2 (M+1);

N-[3-(1S-cyanomethylcarbamoyl-3-methylbutylcarbamoyl)phenyl]-4-(2-morpholin-4-ylethyl)piperazine-1-carboxamide (Compound 377); $^1$H NMR (270 MHz, DMSO-$d_6$) δ0.87 (d, 3), 0.90 (d, 3), 1.48–1.76 (m, 3), 2.9–3.2 (m, 12), 3.6–3.8 (m, 8), 4.12 (d, 2), 4.48 (m, 1), 7.55 (d, 2), 7.83 (d, 2), 8.36 (d, 1 NH), 8.70 (t, 1 NH), 8.91 (s, 1 NH); ESI-MS m/z 514.2 (M+1);

4-[3-(1-benzylpiperidin-4-yl)ureido]-N-(1S-cyanomethylcarbamoyl-3-methylbutyl)benzamide (Compound 378); $^1$H NMR (270 MHz, DMSO-$d_6$) δ0.82 (d, 3), 0.86 (d, 3), 1.45–1.73 (m, 5), 1.88–2.06 (m, 2), 3.0–3.1 (m, 2), 3.30–3.37 (m, 2), 3.7–3.9 (m, 1), 4.09 (d, 2), 4.2–4.3 (m, 2), 4.44 (m, 1), 6.60 (d, 1 NH), 7.42 (d, 2), 7.46 (m, 5), 7.78 (d,2 ), 8.31 (d, 1), 8.66 (m, 1), 8.73 (m, 1); ESI-MS m/z 505.2 (M+1);

4-[3-(1-benzylpyrrolidin-3S-yl)-3-methylureido]-N-(1S-cyanomethylcarbamoyl-3-methylbutyl)benzamide trifluoroacetic acid salt (Compound 379); $^1$H NMR (270 MHz, DMSO-$d_6$, mixture of rotomers) δ0.87 (d, 3), 0.91 (d, 3), 1.48–1.75 (m, 3), 2.0–2.4 (m, 2), 2.96 and 2.99 (s, 3), 3.1–3.7 (m, 4), 4.13 (d, 2), 4.25–4.53 (m, 3), 4.82–4.92 (m, 1), 7.47–7.58 (m, 7), 7.82–7.86 (m, 2), 8.37 (d, 1 NH), 8.66–8.71 (m, 2), 9.94 (br. s, 1); ESI–MS m/z 505.1 (M+1);

4-[3-(1-benzylpyrrolidin-3R-yl)-3-methylureido]-N-(1S-cyanomethylcarbamoyl-3-methylbutyl)benzamide trifluoroacetic acid salt (Compound 380); $^1$H NMR (270 MHz, DMSO-$d_6$, mixture of rotomers) δ0.87 (d, 3), 0.91 (d, 3), 1.48–1.76 (m, 3), 2.0–2.4 (m, 2), 2.96 and 2.99 (s, 3), 3.1–3.7 (m, 4), 4.13 (d, 2), 4.35–4.53 (m, 3), 4.8–4.9 (m, 1), 7.47–7.57 (m, 7), 7.82–7.86 (m, 2), 8.37 (d, 1 NH), 8.66–8.71 (m, 2), 9.9 (br. s, 1); ESI-MS m/z 505.1 (M+1);

N-[4-(1S-cyanomethylcarbamoyl-3-methylbutylcarbamoyl)phenyl]-4-pyrimidin-2-ylpiperazine-1-carboxamide (Compound 381); $^1$H NMR (270 MHz, DMSO-$d_6$) δ0.87 (d, 3), 0.91 (d, 3), 1.48–1.75 (m, 3), 3.55–3.58 (m, 4), 3.77–3.80 (m, 4), 4.12 (d, 2), 4.48 (m, 1), 6.68 (t, 1), 7.58 (d, 2), 7.84 (d, 2), 8.37 (d, 1 NH), 8.40 (d, 2), 8.68 (t, 1 NH), 8.88 (s, 1 NH); ESI-MS m/z 479 (M+1);

N-[4-(1S-cyanomethylcarbamoyl-3-methylbutylcarbamoyl)phenyl]-4-(2-oxo-2-pyrrolidin-1-ylethyl)piperazine-1-carboxamide (Compound 382); $^1$H NMR (270 MHz, DMSO-$d_6$) δ0.86 (d, 3), 0.91 (d, 3), 1.49–1.98 (m, 7), 3.0–3.6 (m, 8), 4.12 (t, 2), 4.22 (br. s, 4), 4.48 (m, 1), 7.55 (d, 2), 7.86 (d, 2), 8.38 (d, 1 NH), 8.70 (t, 1 NH), 9.04 (s, 1 NH); ESI-MS m/z 512.3 (M+1);

N-[3-(1S-cyanomethylcarbamoyl-3-methylbutylcarbamoyl)phenyl]-4-pyrimidin-2-ylpiperazine-1-carboxamide (Compound 384); $^1$H NMR (270 MHz, DMSO-$d_6$) δ0.86 (d, 3), 0.90 (d, 3), 1.47–1.77 (m, 3), 3.52–3.56 (m, 4), 3.75–3.79 (m, 4), 4.11–4.13 (t, 3), 4.50 (m, 1), 6.66 (t, 1), 7.32 (t, 1), 7.50 (d, 1), 7.69 (d, 1), 7.91 (s, 1), 8.39 (d, 2), 8.45 (d, 1 NH), 8.68 (t, 1 NH), 8.78 (s, 1 NH); ESI-MS n/z 479.3 (M+1);

N-[3-(1S-cyanomethylcarbamoyl-3-methylbutylcarbamoyl)phenyl}-4-(2-oxo-2-pyrrolidin-1-ylethyl)piperazine-1-carboxamide trifluoroacetic acid salt (Compound 385); $^1$H NMR (270 MHz, DMSO-$d_6$) δ0.87 (d, 3), 0.91 (d, 3), 1.49–1.98 (m, 7), 3.0–3.6 (m, 8), 4.13 (d, 2), 4.21 (br. s, 4), 4.50 (m, 1), 7.36 (t, 1), 7.56 (d, 1), 7.69 (d, 1), 7.89 (s, 1), 8.48 (d, 1 NH), 8.72 (t, 1 NH), 8.95 (s, 1 NH), 10.1 (br. s, 1); ESI-MS m/z 512.4 (M+1);

N-[3-(1S-cyanomethylcarbamoyl-3-methylbutylcarbamoyl)phenyl]-4-benzlpiperazine-1- carboxamide trifluoroacetic acid salt (Compound 386); $^1$H NMR (270 MHz, DMSO-d$_6$) δ0.87 (d, 3), 0.91 (d, 3), 1.47–1.78 (m, 3), 3.0–3.2 (m, 4), 3.36–3.40 (m, 2), 4.13 (d, 2), 4.2–4.3 (m, 2), 4.38 (br. s, 2), 4.51 (m, 1), 7.36 (t, 1), 7.51 (br. s, 5), 7.56 (d, 1), 7.69 (d, 1), 7.89 (s, 1), 8.48 (d, 1 NH), 8.72 (t, 1 NH), 8.93 (s, 1 NH), 9.8 (br. s, 1); ESI-MS m/z 491.4 (M+1); and 3-[3-(1-benzylpiperidin-4-yl)ureido]-N-(1S-cyanomethylcarbamoyl-3-methylbutyl)benzamide trifluoro acetic acid salt (Compound 387); $^1$H NMR (270 MHz, DMSO-d$_6$) δ0.87 (d, 3), 0.91 (d, 3), 1.45–1.78 (m, 5), 1.93–2.11 (m, 2), 3.02–3.15 (m, 2), 3.30–3.37 (m, 2), 3.7–3.9 (m, 1), 4.13 (d, 2), 4.29–4.38 (m, 2), 4.48 (m, 1), 6.54 (d, 1 NH), 7.31 (t, 1), 7.46 (d, 1), 7.50 (br. s, 5), 7.59 (d, 1), 7.80 (s, 1), 8.47 (d, 1 NH), 8.59 (s, 1 NH), 8.70 (t, 1 NH), 9.46 (br. s, 1); ESI-MS m/z 505.4 (M+1).

Proceeding in a fashion analogous to the procedures exemplified above provided the following compounds of Formula I:

4-(2-pyrid-3-ylthiazol-4-yl)benzyl 1S-cyanomethylcarbamoyl-3-methylbutylcarbamate (Compound 388);

N-(1S-cyanomethylcarbamoyl-3-methylbutyl)-4-[2-(4-methylpiperazin-1-yl)thiazol-4-yl]benzamide (Compound 389);

N-(1S-cyanomethylcarbamoyl-3-methylbutyl)-4-[N-methyl-N-(4-pyrid-4-ylthiazol-2-yl)amino]benzamide (Compound 390);

tert-butyl 4-{4-[4-(1-cyanomethylcatbamoylcyclohexylcarbamoyl)phenoxymethyl]thiazol-2-yl}piperazine-1-carboxylate (Compound 391); NMR (in DMSO-d6): δ8.14 (m, 1H), δ7.87–7.78 (m, 3H), δ7.1–7.0 (m, 2H), δ6.87 (s, 1H), δ4.95 (s, 1H), δ4.00 (s, br, 2H), δ3.81–3.48 (m, 8H), δ1.71–1.31 (m, 19H); MS: M+H$^+$=583.2;

tert-butyl 4-(4-{4-[1S-(1-cyanocyclopropylcarbamoyl)-3-methylbutylcarbamoyl]phenyl}thiazol-2-ylamino)piperidine-1-carboxylate (Compound 392); $^1$H NMR (DMSO): 8.97 (s, 1H), 8.49 (d, 1H), 7.90 (s, 4H), 7.73 (d, 1H), 7.23 (s, 1H), 4.43 (m, 1H), 3.85 (d, 2H), 3.75 (m, 1H), 2.98 (m, 2H), 1.97 (m, 2H), 1.81 (m, 1H), 1.68 (m, 2H), 1.48 (dd, 2H), 1.41 (br s, 11H), 1.11 (dd, 2H), 0.89 (m, 6H); MS: (m=z) 581.4;

N-[1S-(1-cyanocyclopropylcarbamoyl)-3-methylbutyl]-4-(2-piperidin-4-ylaminothiazol-4-yl)benzamide (Compound 393); $^1$H NMR (DMSO): 8.99 (s, 1H), 8.50 (d, 1H), 7.91 (s, 4H), 7.87 (d, 1H), 7.27 (s, 1H), 4.43 (m, 1H), 3.89 (m, 1H), 3.32 (m, 2H), 3.04 (m, 2H), 2.33 (s, 3H), 2.16 (m, 2H), 1.72 (m, 5H), 1.48 (dd, 2H), 1.11 (dd, 2H), 0.89 (m, 6H); MS: (m=z) 481.0;

tert-butyl 4-{4-[4-(1-cyanomethylcarbamoylcyclohexylcarbamoyl)phenyl]thiazol-2-ylamino}piperidine-1-carboxylate (Compound 394); NMR (in DMSO-d6): δ8.31–7.76 (m, 6H), δ7.2 (s, 1H), δ4.20–3.60 (m, 23H), δ2.94 (s, br, 1H), δ2.12–1.05 (m, 21H); MS: M+H$^+$=567.4;

N-[1-(Cyanomethyl-carbamoyl)-2-methyl-butyl]-4-[2-(pyridin-3-ylamino)-thiazol-4-yl]-benzamide (Compound 395); MS: 449 (M+1); $^1$H NMR (DMSO-d6): 0.9 (6H, t+d), 1.23 (1H, m), 1.52(1H, m), 2.00 (1H, m, 4.2 (2H, br d), 4.3 (1H, t, 7Hz), 7.64 (1H, s), 7.7 (1H, m), 7.95–8.1 (4H, 2xd, J=7 Hz), 8.4–8.6 (3H, m*), 8.86 (1H, t), 9.25 (1H, br s), 11.06 (1H, s);

N-[1-(Cyanomethyl-carbamoyl)-cyclohexyl]-4-[2-(piperidin-4-ylamino)-thiazol-4-yl]-benzamide (Compound 396); NMR (in DMSO-d6): δ8.23–7.76 (m, 6H), δ7.24 (s, 1H), δ4.0 (d, 2H), δ3.82 (s, br, 1H), δ3.6–2.8 (m, 43H), δ2.28 (s, 8H), δ2.2–1.14 (m, 10H); MS: –H$^+$=465.0;

4-(4-{4-[1-(Cyanomethyl-carbamoyl)-cyclohexylcarbamoyl]phenyl}-thiazol-2-ylamino)-piperidine-1-carboxylic acid ethyl ester (Compound 397);

(S)-4-Methyl-2-[4-(4-morpholin-4-yl-phenyl)-thiazol-2-ylamino]-pentanoic acid cyanomethyl-amide (Compound 398);

(S)-4-Methyl-2-[4-(4-pyrrolidin-1-yl-phenyl)-thiazol-2-ylamino]-pentanoic acid cyanomethyl-amide (Compound 399);

(S)-4-Methyl-2-[4-(3-phenylsulfonylureidophenyl) thiazol-2-ylamino)-pentanoic acid cyanomethyl-amide (Compound 400);

(S)-4-Methyl-2-{4-[3-(3-phenyl-ureido)-phenyl]-thiazol-2-ylamino}-pentanoic acid cyanomethyl-amide (Compound 401);

(S)-4-Methyl-2-(4-{3-[3-(4-phenoxy-phenyl)-ureido]-phenyl}-thiazol-2-ylamino)-pentanoic acid cyanomethyl-amide (Compound 402);

(S)-4-Methyl-2-(4-{3-[3-((R)-1-phenyl-ethyl)-ureido]-phenyl}-thiazol-2-ylamino)-pentanoic acid cyanomethyl-amide (Compound 403);

N-[1-(Cyanomethyl-carbamoyl)-cyclohexyl]-4-(2-pyridin-4-yl-thiazol-4-yl)-benzami de (Compound 404); NMR (in DMSO-d6): δ8.78 (d, 2H), δ8.55(s, 1H), δ8.22 (m, 1H), δ8.15(d, 2H), δ8.11–8.05 (m, 3H), δ7.99 (d, 2H), δ4.0–4.06 (m, 2H), δ3.69 (s, br, 3H), δ2.11 (d, 2H), δ1.75 (m, 2H), δ1.52 (s, br, 5H), δ1.26 (s, br, 1H); MS: M+H$^+$= 446.4;

(3-{2-[(S)-1-(Cyanomethyl-carbamoyl)-3-methyl-butylamino]-thiazol-4-yl}-phenyl)-carbamic acid 3,4-dichloro-benzyl ester (Compound 405);

N-[(S)-1-(1-Cyano-cyclopropylcarbamoyl)-3-methyl-butyl]-4-(2-piperazin-1-ylmethyl-thiazol-4-yl)-benzamide (Compound 406);

N-[(S)-1-(Cyanomethyl-carbamoyl)-3-methyl-but-3-enyl]-4-[2-(pyridin-4-ylamino)-thiazol-4-yl]-benzamide (Compound 407);

N-[(S)-1-(Cyanomethyl-carbamoyl)-2-naphthalen-2-yl-ethyl]-4-[2-(pyridin-4-ylami no)-thiazol-5-yl]-benzamide (Compound 408);

N-[(S)-1-(Cyanomethyl-carbamoyl)-2-naphthalen-2-yl-ethyl]-4-[2-(pyridin-4-ylamino)-thiazol-4-yl]-benzamide (Compound 410); and N-[(Cyanomethyl-carbamoyl)-dimethylamino-ethyl]-4-(2-pyridin-4-yl-thiazol-4-yl)-benzamide.

Proceeding by methods analogous to those set forth in this Application compounds of Formula I are provided which are comprised by the elements A, B and C listed in the following Table I.

TABLE 1
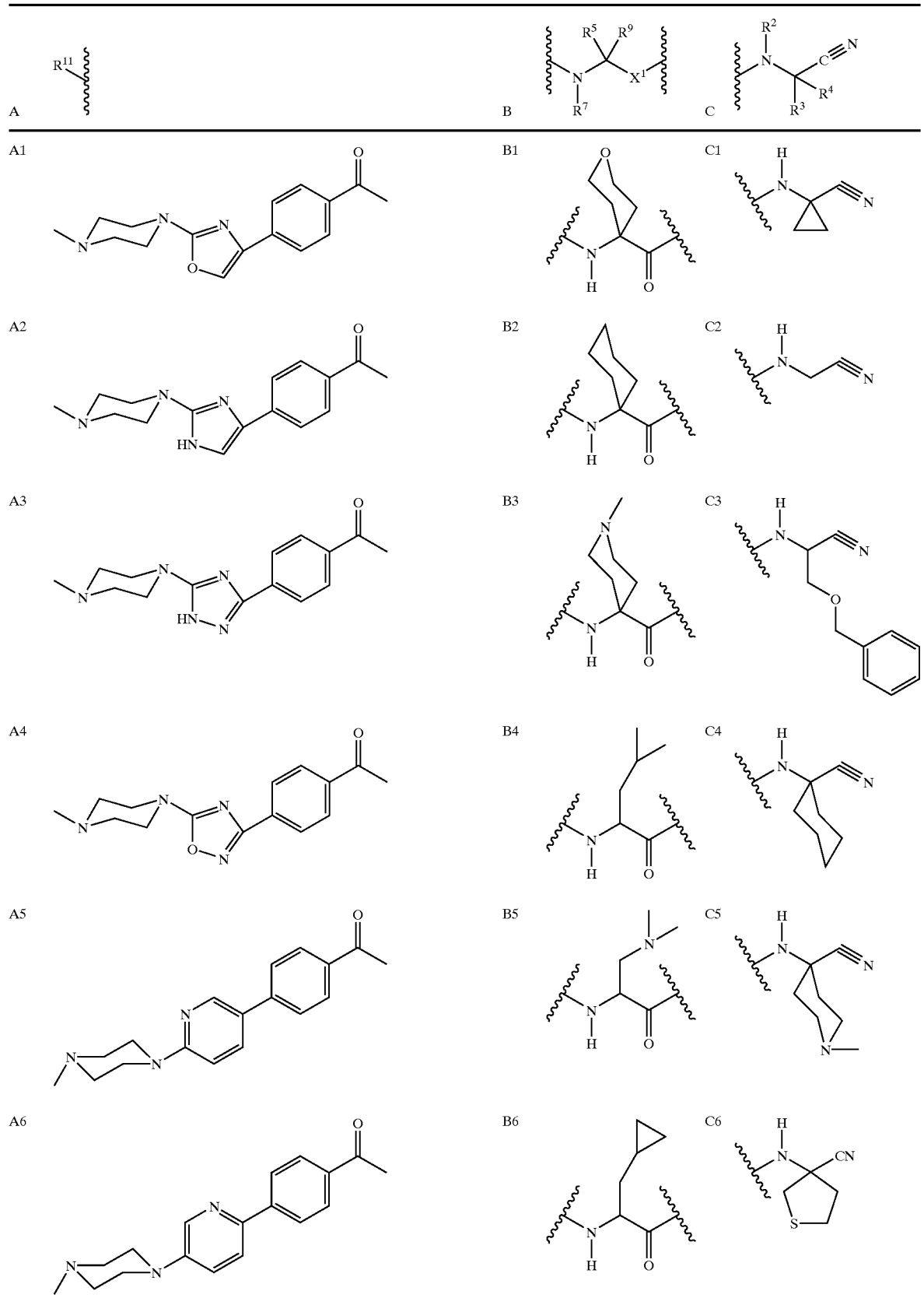

TABLE 1-continued
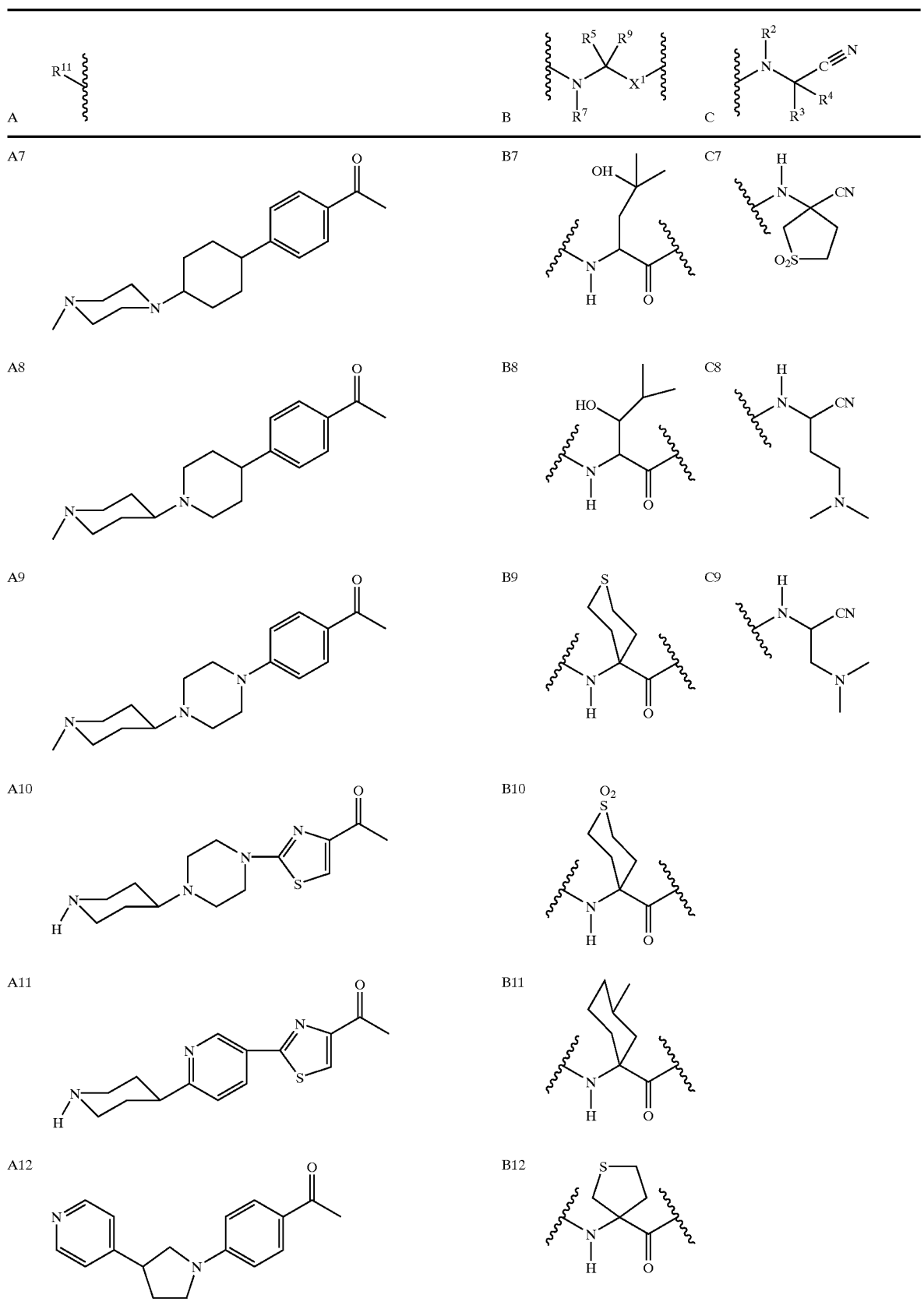

TABLE 1-continued

| A | | B | | C | |
|---|---|---|---|---|---|
| A13 | (4-pyridyl-pyrazol-1-yl)phenyl ketone | B13 | 3-amino-3-(1,1-dioxo-tetrahydrothiophene) linker | | |
| A14 | (4-pyridyl-pyrrol-1-yl)phenyl ketone | | | | |
| A15 | (4-pyridyl-thiazol-2-yl)phenyl ketone | | | | |
| A16 | 4-(2-hydroxyethyl)piperazinyl-thiophenyl ketone | | | | |
| A17 | 4-(2-hydroxyethyl)piperazinyl-furanyl ketone | | | | |
| A18 | 4-(2-hydroxyethyl)piperazinyl-biphenyl ketone | | | | |
| A19 | 1-methylpiperidin-4-yl-piperazinone-phenyl ketone | | | | |

TABLE 1-continued

| A $\overset{R^{11}}{\underset{\xi}{\text{\textbackslash}}}$ | B $\overset{R^5\ R^9}{\underset{R^7}{\text{N}\text{---}\text{X}^1}}$ | C $\overset{R^2}{\underset{R^3}{\text{N}\text{---}\text{C}\equiv\text{N}}}\overset{R^4}{}$ |
|---|---|---|

A20

A21

A22

A23

A24

A25

A26

TABLE 1-continued

| A | B | C |
|---|---|---|
| R11⁓ | ⁓N(R5)(R7)–C(R9)–X1⁓ | ⁓N(R2)–C(R3)(R4)–C≡N |

A27: 2-[4-(2-hydroxyethyl)piperidin-4-yl]-4-(4-acetylphenyl)thiazole

A28: 2-[(4-methylpiperazin-1-yl)methyl]-4-(4-acetylphenyl)thiazole

A29: 2-[2-(4-methylpiperazin-1-yl)ethyl]-4-(4-acetylphenyl)thiazole

A30: 2-(morpholin-4-ylmethyl)-4-(4-acetylphenyl)thiazole

A31: 2-[2-(morpholin-4-yl)ethyl]-4-(4-acetylphenyl)thiazole

A32: 2-(3-aminopyrrolidin-1-yl)-4-(4-acetylphenyl)thiazole

A33: 2-(pyrrolidin-3-yl)-4-(4-acetylphenyl)thiazole

TABLE 1-continued

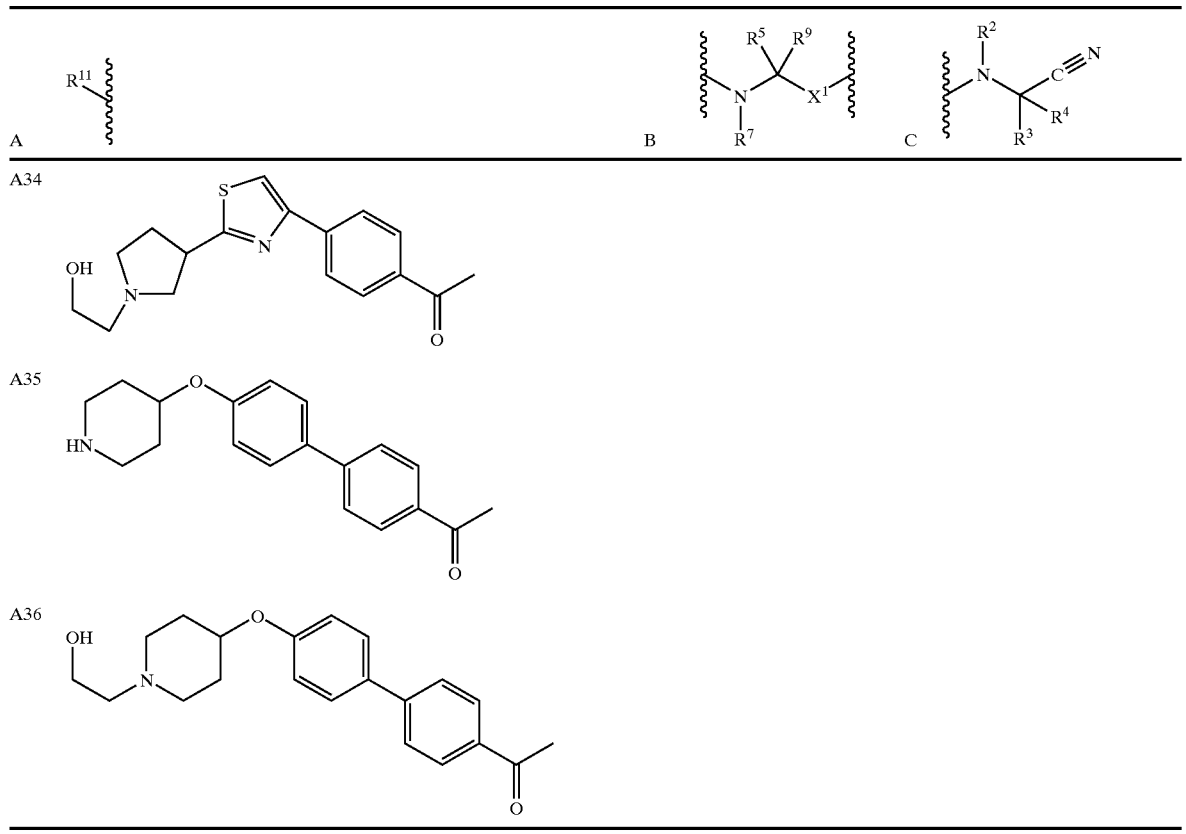

While any combination of the elements A, B and C may comprise the compounds of the Invention, certain combinations are preferred. For example, the following combinations

| | | | |
|---|---|---|---|
| A1-B2-C1 | A9-B2-C1 | A26-B2-C2 | A13-B2-C5 |
| A31-B2-C1 | A10-B2-C1 | A35-B2-C2 | A15-B2-C5 |
| A26-B2-C1 | A13-B2-C1 | A22-B2-C2 | A18-B2-C5 |
| A35-B2-C1 | A15-B2-C1 | A2-B2-C2 | A19-B2-C5 |
| A22-B2-C1 | A18-B2-C1 | A3-B2-C2 | A20-B2-C5 |
| A2-B2-C1 | A19-B2-C1 | A4-B2-C2 | A21-B2-C5 |
| A3-B2-C1 | A20-B2-C1 | A5-B2-C2 | A1-B4-C5 |
| A4-B2-C1 | A21-B2-C1 | A6-B4-C2 | A31-B4-C5 |
| A5-B2-C1 | A1-B4-C2 | A9-B4-C2 | A26-B4-C5 |
| A6-B4-C1 | A31-B4-C2 | A10-B4-C2 | A35-B4-C5 |
| A9-B4-C1 | A26-B4-C2 | A13-B4-C2 | A22-B4-C5 |
| A10-B4-C1 | A35-B4-C2 | A15-B4-C2 | A2-B4-C5 |
| A13-B4-C1 | A22-B4-C2 | A18-B4-C2 | A3-B4-C5 |
| A15-B4-C1 | A2-B4-C2 | A19-B4-C2 | A4-B4-C5 |
| A18-B4-C1 | A3-B4-C2 | A20-B4-C2 | A5-B4-C5 |
| A19-B4-C1 | A4-B4-C2 | A21-B4-C2 | A6-B12-C5 |
| A20-B4-C1 | A5-B4-C2 | A1-B12-C5 | A9-B12-C5 |
| A21-B4-C1 | A6-B12-C2 | A31-B12-C5 | A10-B12-C5 |
| A1-B12-C1 | A9-B12-C2 | A26-B12-C5 | A13-B12-C5 |
| A31-B12-C1 | A10-B12-C2 | A35-B12-C5 | A15-B12-C5 |
| A26-B12-C1 | A13-B12-C2 | A22-B12-C5 | A18-B12-C5 |
| A35-B12-C1 | A15-B12-C2 | A2-B12-C5 | A19-B12-C5 |
| A22-B12-C1 | A18-B12-C2 | A3-B12-C5 | A20-B12-C5 |
| A2-B12-C1 | A19-B12-C2 | A4-B12-C5 | A21-B12-C5 |
| A3-B12-C1 | A20-B12-C2 | A5-B12-C5 | |
| A4-B12-C1 | A21-B12-C2 | A6-B2-C5 | |
| A5-B12-C1 | A1-B2-C2 | A9-B2-C5 | |
| A6-B2-C1 | A31-B2-C2 | A10-B2-C5 | |

Example 17

Cathepsin B Assay

Solutions of test compounds in varying concentrations were prepared in 10 μL of dimethyl sulfoxide (DMSO) and then diluted into assay buffer (40 μL, comprising: N,N-bis(2-hydroxyethyl)-2-aminoethanesulfonic acid (BES), 50 mM (pH 6); polyoxyethylenesorbitan monolaurate, 0.05%; and dithiothreitol (DTT), 2.5 mM). Human cathepsin B (0.025 pMoles in 25 μL of assay buffer) was added to the dilutions. The assay solutions were mixed for 5–10 seconds on a shaker plate, covered and incubated for 30 minutes at room temperature. Z-FR-AMC (20 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Compounds of the invention were tested according to the above-described assay and observed to exhibit cathepsin B inhibitory activity.

Example 18

Cathepsin K Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin K (0.0906 pMoles in 25 μL of assay buffer) was added to the dilutions. The assay solutions were mixed for 5–10 seconds on a shaker plate, covered and incubated for 30 minutes at room temperature. Z-Phe-Arg-AMC (4 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Compounds of the invention were tested according to the above-described assay and observed to exhibit cathepsin K inhibitory activity.

Example 19

Cathepsin L Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin L (0.05 pMoles in 25 μL of assay buffer) was added to the dilutions. The assay solutions were mixed for 5–10 seconds on a shaker plate, covered and incubated for 30 minutes at room temperature. Z-Phe-Arg-AMC (1 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Compounds of the invention were tested according to the above-described assay and observed to exhibit cathepsin L inhibitory activity.

Example 20

Cathepsin S Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM). Human cathepsin S (0.158 pMoles in 25 μL of assay buffer) was added to the dilutions. The assay solutions were mixed for 5–10 seconds on a shaker plate, covered and incubated for 30 minutes at room temperature. Z-Val-Val-Arg-AMC (9 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Compounds of the invention were tested according to the above-described assay and observed to exhibit cathepsin S inhibitory activity.

Example 21

Representative Pharmaceutical Formulations Containing a Compound of Formula I

Oral Formulation

| Compound of Formula I | 10–100 mg |
|---|---|
| Citric Acid Monohydrate | 105 mg |
| Sodium Hydroxide | 18 mg |
| Flavoring | |
| Water | q.s. to 100 mL |

Intravenous Formulation

| Compound of Formula I | 0.1–10 mg |
|---|---|
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

Tablet Formulation

| Compound of Formula I | 1% |
|---|---|
| Microcrystalline Cellulose | 73% |
| Stearic Acid | 25% |
| Colloidal Silica | 1%. |

The resulting tablets are useful for administration in accordance with the methods of this invention for treating or preventing a cathepsin mediated disease state, such as osteoporosis.

We claim:
1. A compound of Formula I:

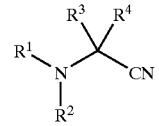

in which:
$R^1$ is a group of Formula (a):

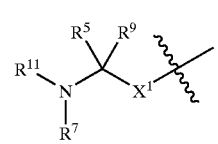

(a)

wherein within Formula (a):
$X^1$ is —C(O)—;
$R^5$ is hydrogen or as defined together with $R^9$;
$R^7$ is hydrogen;
$R^9$ is (i) ($C_{1-6}$)alkyl or
$R^9$ and $R^5$ together with the carbon atom to which both $R^9$ and $R^5$ are attached form ($C_{3-8}$)cycloalkylene or ($C_{3-8}$)heterocycloalkylene; and
$R^{11}$ is —$X^4X^5R^{18}$, wherein $X^4$ is —C(O)—, $X^5$ is a bond, —O— or —$NR^{19}$— where $R^{19}$ is hydrogen or ($C_{1-6}$)alkyl and $R^{18}$ is phenyl, wherein said phenyl ring is substituted by:
(i) —$R^{22}$ where $R^{22}$ is hetero($C_{3-12}$)cycloalkyl($C_{0-6}$)alkyl, or
(ii) —$X^3OR^{22}$, $X^3NR^{22}R^{23}$, —$X^3NR^{23}C(O)R^{22}$, —$X^3NR^{23}C(O)OR^{22}$, —$X^3NR^{23}S(O)_2R^{22}$, —$X^3S(O)_2R^{22}$, —$X^3C(O)R^{22}$ or —$X^3NR^{23}C(O)NR^{22}R^{23}$, wherein $X^3$ is a bond or ($C_{1-6}$)alkylene, $R^{22}$ is hetero($C_{3-12}$)cycloalkyl($C_{0-6}$)alkyl and $R^{23}$ at each occurrence independently is hydrogen or ($C_{1-6}$)alkyl;
wherein within $R^{11}$ any alicyclic or aromatic ring system present may be substituted further by 1 to 5 radicals independently selected from ($C_{1-6}$)alkyl, ($C_{1-6}$)alkylidene, cyano, halo, halo-substituted ($C_{1-4}$)

alkyl, nitro, —$X^3NR^{12}R^{12}$, —$X^3NR^{12}C(O)OR^{12}$, —$X^3NR^{12}C(O)NR^{12}R^{12}$, —$X^3NR^{12}C(NR^{12})NR^{12}R^{12}$, —$X^3OR^{12}$, —$X^3SR^{12}$, —$X^3C(O)OR^{12}$, —$X^3C(O)NR^{12}R^{12}$, —$X^3S(O)_2NR^{12}R^{12}$, —$X^3P(O)(OR^3)OR^{12}$, —$X^3OP(O)(OR^3)OR^{12}$, —$X^3NR^{12}C(O)R^{13}$, —$X^3S(O)R^{13}$, —$X^3S(O)_2R^{13}$ and —$X^3C(O)R^{13}$, wherein $X^3$ is a bond or ($C_{1-6}$)alkylene, $R^{12}$ at each occurrence independently is hydrogen, ($C_{1-6}$)alkyl or halo-substituted ($C_{1-3}$)alkyl and $R^{13}$ is ($C_{1-6}$)alkyl or halo-substituted ($C_{1-3}$)alkyl;

$R^3$ is hydrogen or as defined together with $R^4$; and $R^4$ is (i) hydrogen or $R^4$ and $R^3$ taken together with the carbon atom to which both $R^4$ and $R^3$ are attached form ($C_{3-8}$)cycloalkylene or ($C_{3-8}$)heterocycloalkylene, wherein said ($C_{3-8}$)cycloalkylene or ($C_{3-8}$)heterocycloalkylene optionally is substituted with ($C_{1-6}$)alkyl; or a N-oxide derivative, individual stereoisomer or mixture of stereoisomers, or a pharmaceutically acceptable salt thereof.

2. The compound of claim 1 wherein:

$R^9$ and $R^5$ together with the carbon atom to which both $R^9$ and $R^5$ are attached form ($C_{3-8}$)cycloalkylene or ($C_{3-8}$)heterocycloalkylene.

3. A compound of Formula (I):

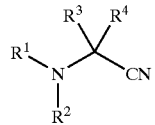

in which:

$R^1$ is a group of Formula (a):

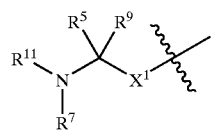

wherein within Formula (a):

$X^1$ is —C(O)—;

$R^5$ is hydrogen or as defined together with $R^9$;

$R^7$ is hydrogen;

$R^9$ is (i) ($C_{1-6}$)alkyl or $R^9$ and $R^5$ together with the carbon atom to which both $R^9$ and $R^5$ are attached form ($C_{3-8}$)cycloalkylene or ($C_{3-8}$)heterocycloalkylene; and $R^{11}$ is —$X^4X^5R^{18}$, wherein $X^4$ is —C(O)—, $X^5$ is a bond, —O— or —$NR^{19}$— where $R^{19}$ is hydrogen or ($C_{1-6}$)alkyl and $R^{18}$ is phenyl, wherein said phenyl ring is substituted by:

(i) —$R^{22}$ where $R^{22}$ is hetero($C_{3-12}$)cycloalkyl($C_{0-6}$)alkyl wherein said heterocycloalkyl is comprised of one or more ring members selected from —N=, —NR—, —O—, —S— or —$S(O)_2$ wherein R is ($C_{1-6}$)alkyl, or (ii) —$X^3OR^{22}$, —$X^3NR^{22}R^{23}$, —$X^3NR^{23}C(O)R^{22}$, —$X^3NR^{23}C(O)OR^{22}$, —$X^3NR^{23}S(O)_2R^{22}$, —$X^3S(O)_2R^{22}$, —$X^3C(O)R^{22}$ or —$X^3NR^{23}C(O)NR^{22}R^{23}$, wherein $X^3$ is ($C_{1-6}$)alkylene, $R^{22}$ is hetero($C_{3-12}$)cycloalkyl($C_{0-6}$)alkyl wherein said heterocycloalkyl is comprised of one or more ring members selected from —N=, —NR—, —O—, —S— or —$S(O)_2$ wherein R is ($C_{1-6}$)alkyl and $R^{23}$ at each occurrence independently is hydrogen or ($C_{1-6}$)alkyl;

wherein within $R^{11}$ any alicyclic or aromatic ring system present may be substituted further by 1 to 5 radicals independently selected from ($C_{1-6}$)alkyl, ($C_{1-6}$)alkylidene, cyano, halo, halo-substituted ($C_{1-4}$)alkyl, nitro, —$X^3NR^{12}R^{12}$, —$X^3NR^{12}C(O)OR^{12}$, —$X^3NR^{12}C(O)NR^{12}R^{12}$, —$X^3NR^{12}C(NR^{12})NR^{12}R^{12}$, —$X^3OR^{12}$, —$X^3SR^{12}$, —$X^3C(O)OR^{12}$, —$X^3C(O)NR^{12}R^{12}$, —$X^3S(O)_2NR^{12}R^{12}$, —$X^3P(O)(OR^3)OR^{12}$, —$X^3OP(O)(OR^3)OR^{12}$, —$X^3NR^{12}C(O)R^{13}$, —$X^3S(O)R^{13}$, —$X^3S(O)_2R^{13}$ and —$X^3C(O)R^{13}$, wherein $X^3$ is ($C_{1-6}$)alkylene, $R^{12}$ at each occurrence independently is hydrogen, ($C_{1-6}$)alkyl or halo-substituted ($C_{1-3}$)alkyl and $R^{13}$ is ($C_{1-6}$)alkyl or halo-substituted ($C_{1-3}$)alkyl;

$R^3$ is hydrogen or as defined together with $R^4$; and $R^4$ is (i) hydrogen or $R^4$ and $R^3$ taken together with the carbon atom to which both $R^4$ and $R^3$ are attached form ($C_{3-8}$)cycloalkylene or ($C_{3-8}$)heterocycloalkylene, wherein said ($C_{3-8}$)cycloalkylene or ($C_{3-8}$)heterocycloalkylene optionally is substituted with ($C_{1-6}$)alkyl; or a N-oxide derivative, individual stereoisomer or mixture of stereoisomers; or a pharmaceutically acceptable salt thereof.

4. The compound of claim 3 wherein:

$R^9$ and $R^5$ together with the carbon atom to which both $R^9$ and $R^5$ are attached form ($C_{3-8}$)cycloalkylene or ($C_{3-8}$)heterocycloalkylene.

5. The compound of claim 4 wherein $R^{18}$ is phenyl wherein said phenyl is substituted with —$R^{22}$ where $R^{22}$ is hetero($C_{3-12}$)cycloalkyl($C_{0-6}$)alkyl wherein said heterocycloalkyl is comprised of one or more ring members selected from —N=, —NR—, —O—, —S— or —$S(O)_2$ wherein R is ($C_{1-6}$)alkyl.

6. The compound of claim 5 wherein said hetero($C_{3-12}$)cycloalkyl($C_{0-6}$)alkyl is selected from the group consisting of [1,4']bipiperidinylyl, dihydrooxazolyl, morpholinyl, 1-morpholin-4-ylpiperidinyl, piperazinyl, piperidyl, pirazolidinyl, pirazolinyl, pyrrolinyl, pyrrolidinyl, and quinuclidinyl wherein the nitrogen atom is substituted with ($C_{1-6}$)alkyl.

7. A compound which is selected from a group consisting of:

N-[1-(cyanomethyl-carbamoyl)-3-methyl-butyl]-3-[3-(3-morpholin-4-yl-propyl)-ureido]-benzamide;

4-dimethylamino-piperidine-1-carboxylic acid {4-[1-(cyanomethyl-carbamoyl)-3-methyl-butylcarbamoyl]-phenyl}-amide; and N-(1S-cyanomethylcarbamoyl-3-methylbutyl)-4-(4-methylpiperazin-1-yl)benzamide; and the N-oxide derivative, individual stereoisomer and mixture of stereoisomers; and the pharmaceutically acceptable salt thereof.

8. A pharmaceutical composition comprising a therapeutically effective amount of a compound of claim 1 or 3 in combination with a pharmaceutically acceptable excipient.

9. A method of treating a disease in an animal in which cysteine protease activity contributes to the pathology and/or symptomatology of the disease, which method comprises administering to the animal a therapeutically effective amount of compound of claim 1 or 3; or a N-oxide derivative, individual stereoisomer or mixture of stereoisomers or a pharmaceutically acceptable salt thereof.

10. The method of claim 9 wherein the disease is osteoporosis.

11. The method of claim 10 wherein the animal is a human.

12. The method of claim 11 wherein the human is a post-menopausal woman.

13. The method of claim 12 wherein the cysteine protease is cathepsin K.

* * * * *